United States Patent
Levner et al.

(10) Patent No.: US 10,273,441 B2
(45) Date of Patent: Apr. 30, 2019

(54) PERFUSION MANIFOLD ASSEMBLY

(71) Applicant: EMULATE, Inc., Boston, MA (US)

(72) Inventors: Daniel Levner, Brookline, MA (US); Josiah Daniel Sliz, Boston, MA (US); Christopher David Hinojosa, Cambridge, MA (US); Guy Robert Thompson, II, Watertown, MA (US); Petrus Wilhelmus Martinus van Ruijven, Glen Waverley (AU); Matthew Daniel Solomon, Hughesdale (AU); Christian Alexander Potzner, Port Melbourne (AU); Patrick Sean Tuohy, St. Kilda (AU); Joshua Gomes, Somerville, MA (US); Norman Wen, West Roxbury, MA (US); Jacob Freake, Somerville, MA (US); Doug Sabin, Woburn, MA (US)

(73) Assignee: EMULATE, Inc., Boston, MA (US)

( * ) Notice: Subject to any disclaimer, the term of this patent is extended or adjusted under 35 U.S.C. 154(b) by 348 days.

(21) Appl. No.: 15/248,633

(22) Filed: Aug. 26, 2016

(65) Prior Publication Data

US 2017/0055522 A1  Mar. 2, 2017

Related U.S. Application Data

(60) Provisional application No. 62/366,482, filed on Jul. 25, 2016, provisional application No. 62/361,244, (Continued)

(51) Int. Cl.
*C12M 1/34* (2006.01)
*C12M 1/36* (2006.01)
(Continued)

(52) U.S. Cl.
CPC ............ *C12M 23/16* (2013.01); *A01N 1/021* (2013.01); *A01N 1/0247* (2013.01);
(Continued)

(58) Field of Classification Search
CPC ...... C12M 23/16; C12M 23/42; C12M 23/38; C12M 41/48; C12M 41/40; C12M 21/08;
(Continued)

(56) References Cited

U.S. PATENT DOCUMENTS

| 8,647,861 B2 | 2/2014 | Ingber et al. ............... 435/289.1 |
| 10,184,102 B2 * | 1/2019 | Levner ................... C12M 23/16 |

(Continued)

FOREIGN PATENT DOCUMENTS

| EP | 1895308 A1 | 3/2008 |
| WO | WO200241996 | 5/2002 |

(Continued)

OTHER PUBLICATIONS

U.S. Appl. No. 62/024,361, filed Jul. 14, 2014.
(Continued)

*Primary Examiner* — Michael L Hobbs
(74) *Attorney, Agent, or Firm* — Medlen & Carroll, LLP

(57) ABSTRACT

The invention relates to a perfusion manifold assembly that allows for perfusion of a microfluidic device, such as an organ on a chip microfluidic device comprising cells that mimic cells in an organ in the body, that is detachably linked with an assembly so that fluid enters ports of the microfluidic device from a fluid reservoir, optionally without tubing, at a controllable flow rate. The invention further relates to a drop-to-drop connection scheme for putting a microfluidic device in fluidic communication with a fluid source or another microfluidic device, including but not limited to, putting a microfluidic device in fluidic communication with the perfusion manifold assembly.

42 Claims, 60 Drawing Sheets

Related U.S. Application Data filed on Jul. 12, 2016, provisional application No. 62/250,861, filed on Nov. 4, 2015, provisional application No. 62/210,122, filed on Aug. 26, 2015.

(51) Int. Cl.

| | | |
|---|---|---|
| *A01N 1/02* | (2006.01) | |
| *C12M 3/06* | (2006.01) | |
| *B01L 3/00* | (2006.01) | |
| *C12M 1/00* | (2006.01) | |
| *C12M 1/42* | (2006.01) | |
| *C12N 5/071* | (2010.01) | |
| *C12M 3/00* | (2006.01) | |
| *B01L 9/00* | (2006.01) | |

(52) U.S. Cl.
CPC ..... *B01L 3/50273* (2013.01); *B01L 3/502707* (2013.01); *B01L 3/502715* (2013.01); *B01L 3/502738* (2013.01); *B01L 9/527* (2013.01); *C12M 21/08* (2013.01); *C12M 23/38* (2013.01); *C12M 23/40* (2013.01); *C12M 23/42* (2013.01); *C12M 29/10* (2013.01); *C12M 35/04* (2013.01); *C12M 41/40* (2013.01); *C12M 41/48* (2013.01); *C12N 5/0602* (2013.01); *B01L 2200/025* (2013.01); *B01L 2200/027* (2013.01); *B01L 2200/12* (2013.01); *B01L 2300/0681* (2013.01); *B01L 2300/0887* (2013.01); *B01L 2300/123* (2013.01); *B01L 2300/14* (2013.01); *B01L 2300/161* (2013.01); *B01L 2300/165* (2013.01); *B01L 2400/0481* (2013.01); *B01L 2400/0487* (2013.01); *B01L 2400/06* (2013.01); *C12N 2521/00* (2013.01)

(58) Field of Classification Search
CPC . C12M 35/04; C12M 29/10; B01L 3/502738; B01L 3/502707; B01L 3/502715; B01L 2300/0681; B01L 2300/123; B01L 2300/14; B01L 2300/0887; B01L 2300/165; B01L 2300/161; B01L 2200/027; B01L 2200/12; B01L 2200/025; B01L 2400/0487; B01L 2400/06; A01N 1/021; A01N 1/0247; C12N 5/0602; C12N 2521/00

See application file for complete search history.

(56) References Cited

U.S. PATENT DOCUMENTS

| | | | |
|---|---|---|---|
| 2003/0132112 A1 | 7/2003 | Beebe et al. | 204/450 |
| 2003/0203506 A1 | 10/2003 | Beebe et al. | 436/180 |
| 2005/0105077 A1 | 5/2005 | Padmanabhan et al. | 356/436 |
| 2006/0128006 A1 | 6/2006 | Gerhardt et al. | 435/287.1 |
| 2008/0261295 A1 | 10/2008 | Butler et al. | 435/286.5 |
| 2009/0130719 A1 | 5/2009 | Handique | 435/91.2 |
| 2012/0152369 A1* | 6/2012 | Hiddessen | B01L 3/502784 137/14 |
| 2013/0115607 A1 | 5/2013 | Nielsen et al. | 435/6.12 |
| 2014/0174160 A1 | 6/2014 | Michienzi et al. | 73/61.58 |
| 2016/0136643 A1 | 5/2016 | Larson | 435/6.1 |

FOREIGN PATENT DOCUMENTS

| | | |
|---|---|---|
| WO | WO/2007/084425 | 7/2007 |
| WO | WO/2015/021228 | 2/2015 |
| WO | PCT/US2015/040026 | 7/2015 |
| WO | WO2016010861 | 1/2016 |

OTHER PUBLICATIONS

U.S. Appl. No. 62/127,438, filed Mar. 3, 2015, Hinojosa, et al.
Avram, et al., "Plasma Surface Modification for Selective Hydrophobic Control," *Romanian J. Information Science and Technology*, vol. 11, No. 4:409-422 (2008).
Hong, et al., "Hydrophilic Surface Modification of PDMS Using Atmospheric RF Plasma," *Journal of Physics: Conference Series* 34:656-661 (Institute of Physics Publishing) (2006).
Huh, et al., "Microfabrications of human organs-on-chips", Nature Protocols, 8(11):2135-2157 (2013).

* cited by examiner

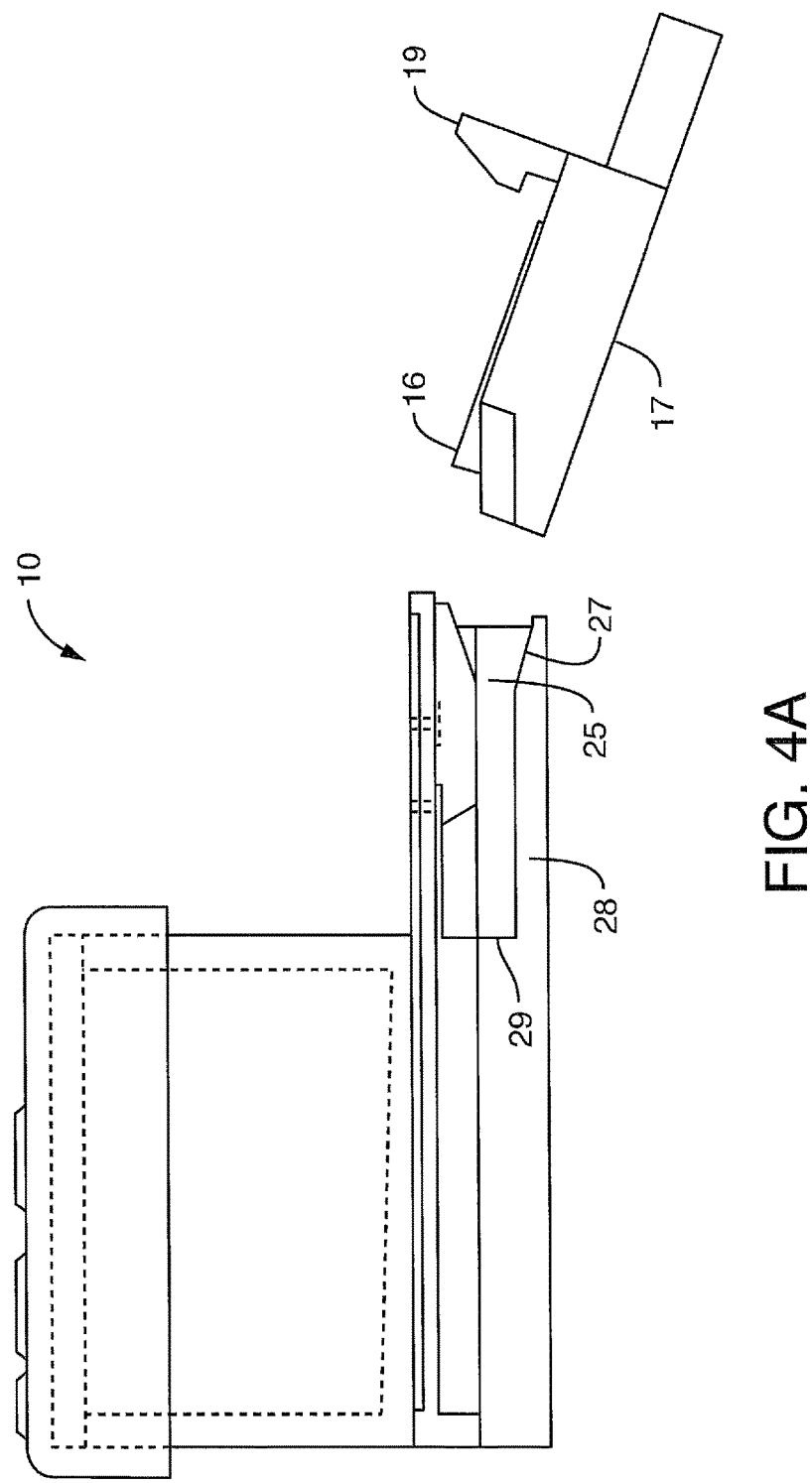

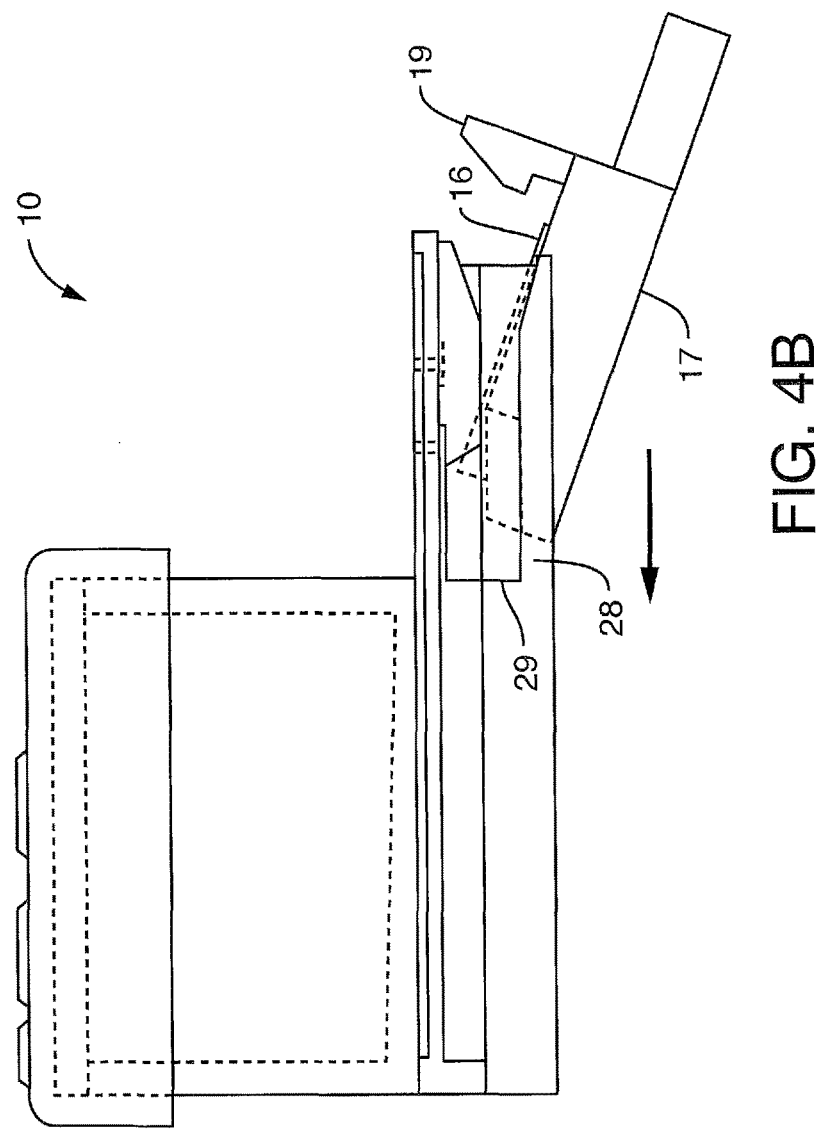

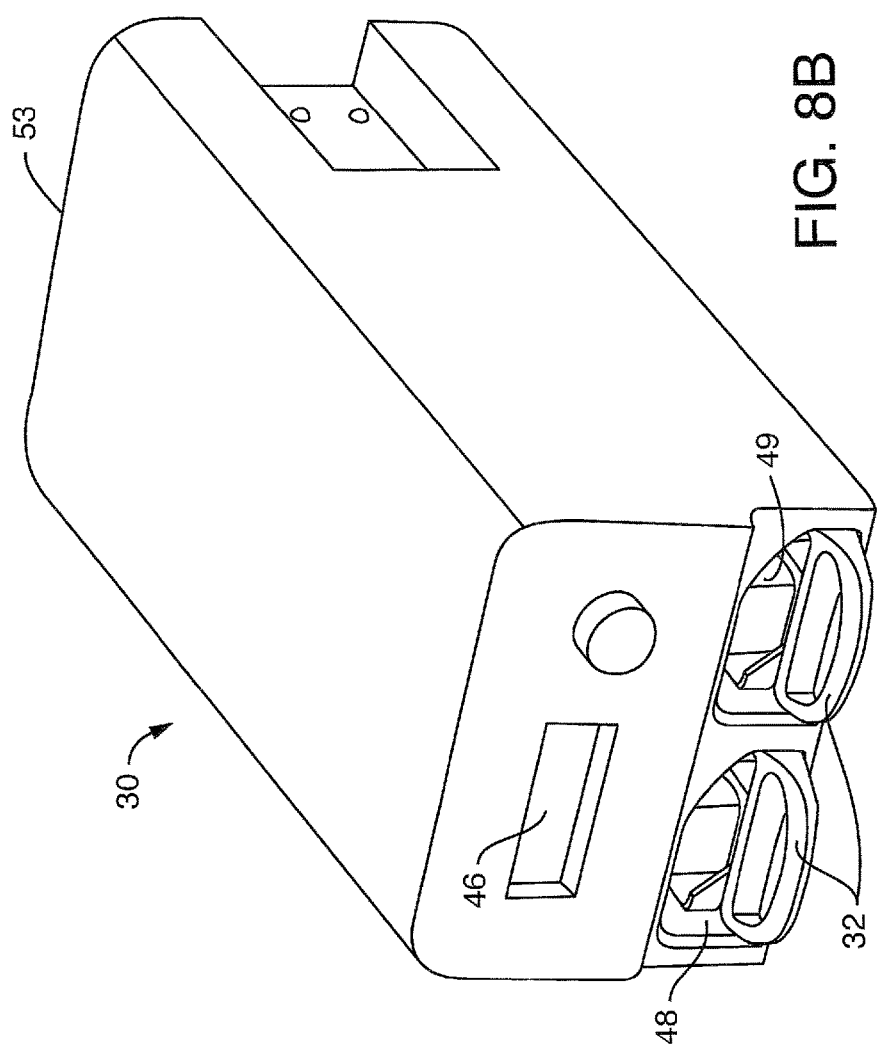

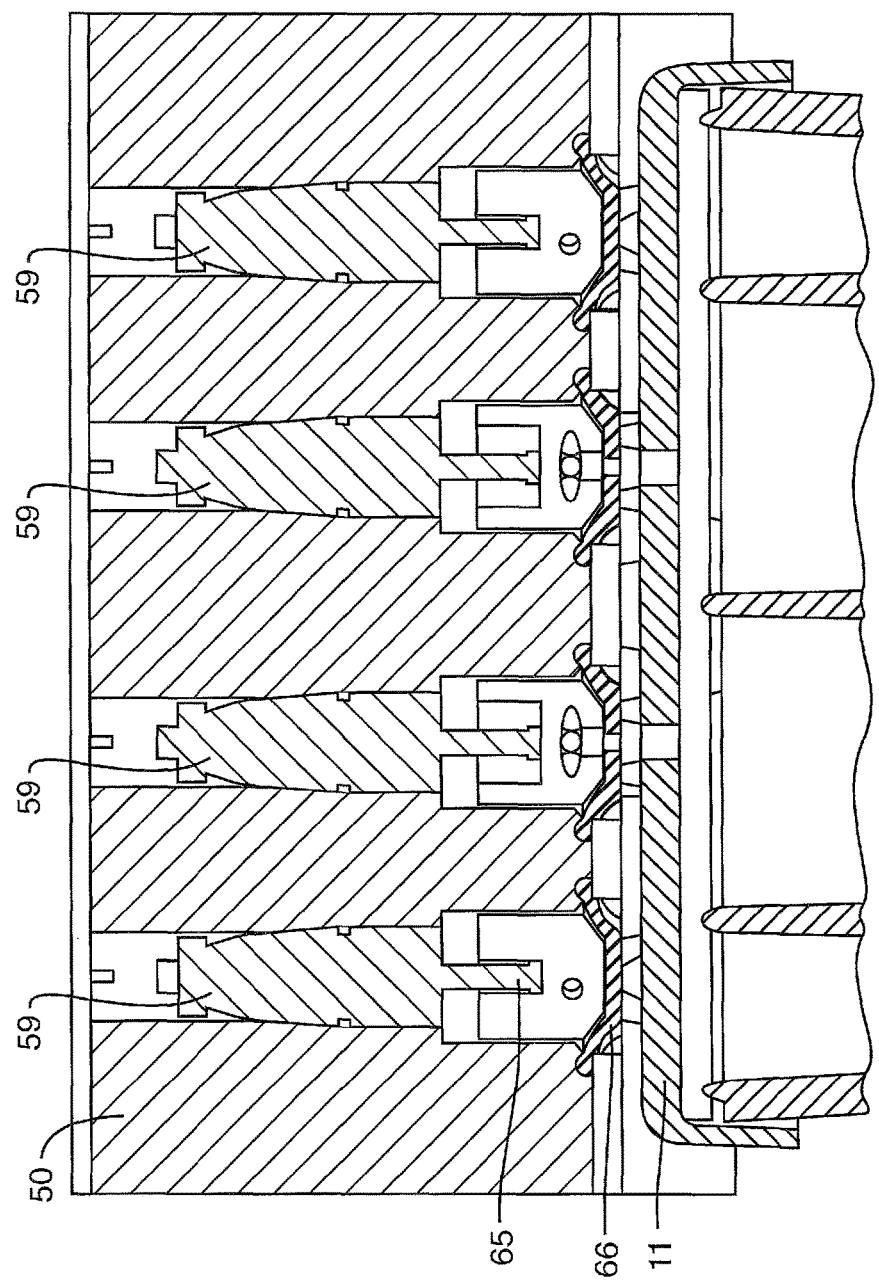

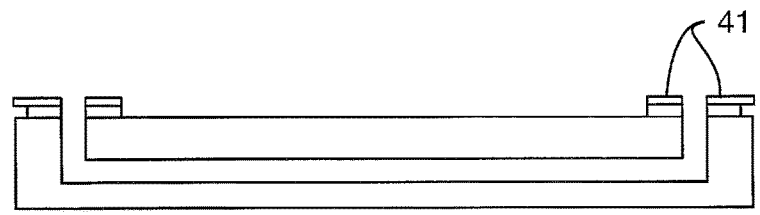
FIG. 24A
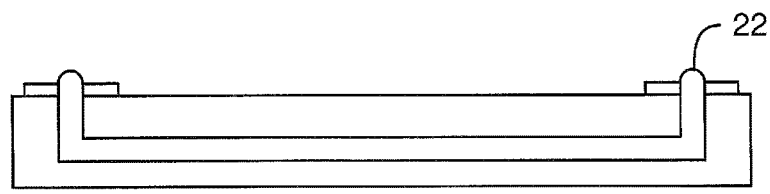
FIG. 24B
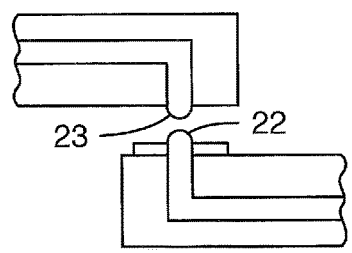 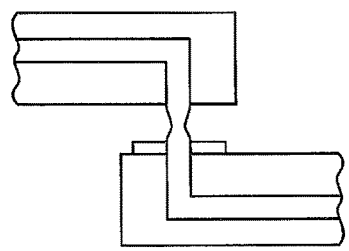
FIG. 24C            FIG. 24D

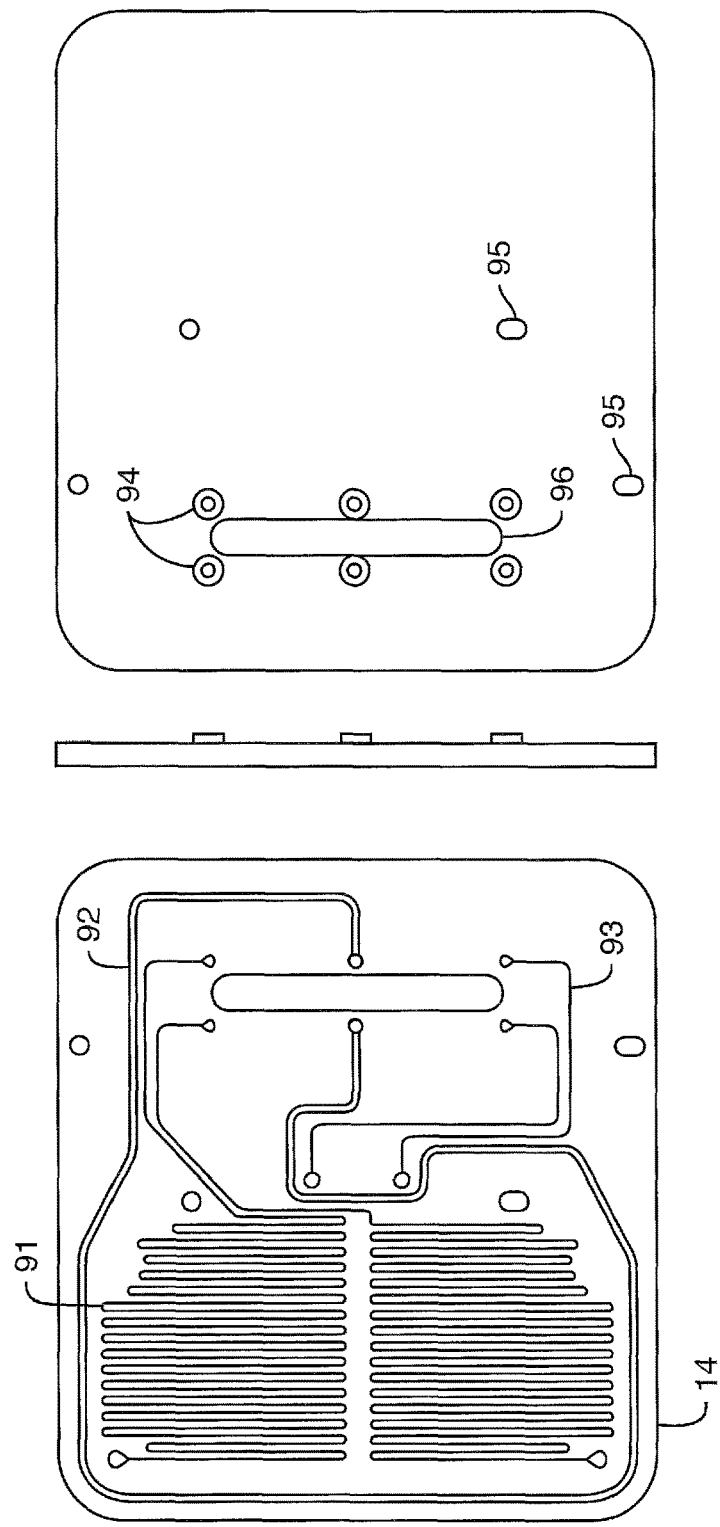

US 10,273,441 B2

PERFUSION MANIFOLD ASSEMBLY

This invention was made with government support under Grant number W911NF-12-2-0036 awarded by the Army Research Office/Defense Advanced Research Projects Agency-DARPA. The Government has certain rights in the invention.

FIELD OF THE INVENTION

A perfusion manifold assembly is contemplated that allows for perfusion of a microfluidic device, such as an organ on a chip microfluidic device comprising cells that mimic cells in an organ in the body or at least one function of an organ, that is detachably linked with said assembly so that fluid enters ports of the microfluidic device from a fluid reservoir, optionally without tubing, at a controllable flow rate. A drop-to-drop connection scheme is contemplated as one embodiment for putting a microfluidic device in fluidic communication with a fluid source or another microfluidic device, including but not limited to, putting a microfluidic device in fluidic communication with the perfusion manifold assembly.

BACKGROUND OF THE INVENTION

Two-dimensional (2D) monolayer cell culture systems have been used for many years in biological research. The most common cell culture platform is the two-dimensional (2D) monolayer cell culture in petri dishes or flasks. Although such 2D in vitro models are less expensive than animal models and are conducive to systematic, and reproducible quantitative studies of cell physiology (e.g., in drug discovery and development), the physiological relevance of the information retrieved from in vitro studies to in vivo system is often questionable. It has now been widely accepted that three-dimensional (3D) cell culture matrix promotes many biological relevant functions not observed in 2D monolayer cell culture. Said another way, 2D cell culture systems do not accurately recapitulate the structure, function, physiology of living tissues in vivo.

U.S. Pat. No. 8,647,861 describes microfluidic "organ-on-chip" devices comprising living cells on membranes in microchannels exposed to culture fluid at a flow rate. In contrast to static 2D culture, microchannels allow the perfusion of cell culture medium throughout the cell culture during in vitro studies and as such offer a more in vivo-like physical environment. In simple terms, an inlet port allows injection of cell culture medium into a cell-laden microfluidic channel or chamber, thus delivering nutrients and oxygen to cells. An outlet port then permits the exit of remaining medium as well as harmful metabolic by-products.

While such microfluidic devices are an improvement over traditional static tissue culture models, the small size, scale and interface of these devices makes fluid handling difficult. What is needed is a way to control perfusion of these devices in a manner whereby fluid pressure creates a flow rate that applies a desired fluid shear stress to the living cells. Ideally, the solution should provide for a simple user workflow.

SUMMARY OF THE INVENTION

The present invention contemplates a number of devices separately and in combination. The present invention contemplates a perfusion manifold assembly (also referred to as a cartridge, pod or perfusion disposable, whether or not there is any requirement or intent to dispose of the component) is contemplated that retains one or more microfluidic devices, such as "organ-on-a-chip" microfluidic devices (or simply "microfluidic chip") that comprise cells that mimic at least one function of an organ in the body, and allow the perfusion and optionally the mechanical actuation of said microfluidic devices, optionally without tubing. The present invention contemplates a number of embodiments of the perfusion manifold assembly. However, it is not intended that the present invention be limited to these embodiments. For example, the present invention contemplates combining features from different embodiments (as discussed below). In addition, the present invention contemplates removing features from the embodiments (as discussed below). Furthermore, the present invention contemplates substituting features in the embodiments (as discussed below).

A culture module is contemplated that allows the perfusion and optionally mechanical actuation of one or more microfluidic devices, such as organ-on-a-chip microfluidic devices comprising cells that mimic at least one function of an organ in the body. In one embodiment, the microfluidic device comprises a top channel, a bottom channel, and a membrane separating at least a portion of said top and bottom channels. In one embodiment, the microfluidic device comprises cells on the membrane and/or in or on the channels. In one embodiment, the culture module comprises a pressure manifold that allows for perfusion of a microfluidic device, such as an "organ on chip" microfluidic device comprising cells that mimic cells in an organ in the body or at least one function of an organ, that is optionally retained in contact with a perfusion disposable and detachably linked with said assembly so that fluid enters ports of the microfluidic device from a fluid reservoir, optionally without tubing, at a controllable flow rate. The perfusion disposable can be used separately from the culture module, and the microfluidic device or chip can be used separately from the perfusion disposable. In one embodiment, the present invention contemplates a (moving or non-moving) pressure manifold configured to mate with one or more microfluidic devices (such as any one of the perfusion manifold assembly embodiments described herein) with integrated valves that can prevent gas leaks when not mated with a microfluidic device.

A drop-to-drop connection scheme is contemplated as one embodiment for putting a microfluidic device in fluidic communication with a fluid source or another microfluidic device, including but not limited to, putting a microfluidic device in fluidic communication with a perfusion disposable. In one embodiment, the microfluidic device comprises a top channel, a bottom channel, and a membrane separating at least a portion of said top and bottom channels. In one embodiment, the microfluidic device comprises cells on the membrane and/or in or on the channels.

A pressure lid is contemplated that allows for the pressurization of one or more reservoirs within a perfusion disposable or perfusion manifold assembly (or other microfluidic device), the pressure lid being movable or removably attached to said perfusion disposable or other microfluidic device to allow improved access to elements (e.g. reservoirs) within. The pressure lid can be removed from the perfusion disposable and the perfusion disposable can be used without the lid. In one embodiment, the perfusion disposable comprises a microfluidic chip, and the chip comprises a top channel, a bottom channel, and a membrane separating at least a portion of said top and bottom channels. In one embodiment, the microfluidic chip comprises cells on the membrane and/or in or on the channels.

A method for pressure control is contemplated to allow the control of flow rate (while perfusing cells) despite limitations of common pressure regulators. Rather than having the pressure controllers (or actuators) of a culture module "on" all of the time (or at just one setpoint), in one embodiment, they are switched "on" and "off" (or between two or more setpoints) in a pattern. Accordingly, the switching pattern may be selected such that the average value of pressure acting liquid in one or more reservoirs of an engaged perfusion disposable (containing a microfluidic device or chip) corresponds to a desired value. In one embodiment, the microfluidic device comprises a top channel, a bottom channel, and a membrane separating at least a portion of said top and bottom channels. In one embodiment, the microfluidic device comprises cells on the membrane and/or in or on the channels.

In one embodiment, the perfusion manifold assembly comprises i) a cover or lid configured to serve as the top of ii) one or more fluid reservoirs, iii) a capping layer under said fluid reservoir(s), iv) a fluidic backplane under, and in fluidic communication with, said fluid reservoir(s), said fluidic backplane comprising a resistor, and v) a projecting member or skirt (for engaging the microfluidic device or a carrier containing a microfluidic device). As noted above, the cover or lid can be removed and the perfusion manifold assembly can still be used. In one embodiment, the assembly further comprises fluid ports positioned at the bottom of the fluidic backplane. In one embodiment, the capping layer caps the fluid backplane. Without being bound by theory of any particular mechanism, it is believed that these resistors serve to stabilize the flow of fluid coming from the reservoirs so that a stable flow can be delivered to the microfluidic device, and/or they serve to provide a means for translating reservoir pressure to perfusion flow rate. In one embodiment, the lid is held onto the reservoir using a radial seal. This does not require an applied pressure to create a seal. In another embodiment, the lid is held onto the reservoir using one or more clips, screws or other retention mechanisms. In one embodiment, the projecting member or skirt is engaged with a microfluidic chip. In one embodiment, the microfluidic chip comprises a top channel, a bottom channel, and a membrane separating at least a portion of said top and bottom channels. In one embodiment, the microfluidic device comprises cells on the membrane and/or in or on the channels.

In one embodiment, the perfusion manifold assembly comprises i) one or more fluid reservoirs, and ii) a fluidic backplane under, and in fluidic communication with, said fluid reservoir(s), said fluidic backplane comprising fluid channels that terminate a ports. In one embodiment, the fluidic backplane comprises a resistor. In one embodiment, the perfusion manifold assembly further comprises iii) a projecting member or skirt. In one embodiment, the skirt comprises a guide mechanism (for engaging the microfluidic device or a carrier containing a microfluidic device). In one embodiment, the guide mechanism comprises a guide shaft or a hole, groove, orifice or other cavity configured to accept a guide shaft. In one embodiment, the guide mechanism comprises (external or internal) guide tracks. In one embodiment, the guide tracks are side tracks (for engaging the microfluidic device or carrier). In one embodiment, the perfusion manifold assembly may further include a capping layer that caps the fluidic backplane. The embodiment may further optionally include a cover or lid. In one embodiment, the lid is held onto the reservoir using a radial seal. This does not require an applied pressure to create a seal. In another embodiment, the lid is held onto the reservoir using one or more clips, screws or other retention mechanisms. In one embodiment, fluidic ports are at the bottom of the fluidic backplane. In one embodiment, the projecting member or skirt is engaged with a microfluidic chip. In one embodiment, the microfluidic chip comprises a top channel, a bottom channel, and a membrane separating at least a portion of said top and bottom channels. In one embodiment, the microfluidic device comprises cells on the membrane and/or in or on the channels.

In one embodiment, the perfusion manifold assembly comprises i) one or more fluid reservoirs, ii) a fluidic backplane under, and in fluidic communication with, said fluid reservoir(s), and iii) a projecting member or skirt (for engaging the microfluidic device or a carrier containing a microfluidic device). The embodiment may further include a capping layer that caps the fluidic backplane. The embodiment may further optionally include a cover or lid. In one embodiment, the lid is held onto the reservoir using a radial seal. This does not require an applied pressure to create a seal. In another embodiment, the lid is held onto the reservoir using one or more clips, screws or other retention mechanisms. In one embodiment, fluidic ports are at the bottom of the fluidic backplane. In one embodiment, the projecting member or skirt is engaged with a microfluidic chip. In one embodiment, the microfluidic chip comprises a top channel, a bottom channel, and a membrane separating at least a portion of said top and bottom channels. In one embodiment, the microfluidic device comprises cells on the membrane and/or in or on the channels.

In one embodiment, the perfusion manifold assembly comprises i) one or more fluid reservoirs, ii) a fluidic backplane under, and in fluidic communication with, said fluid reservoir(s), and iii) a capping layer that caps the fluidic backplane. In one embodiment, said fluidic backplane comprising one or more resistors. In one embodiment, the assembly further comprises optionally iv) a projecting member or skirt (for engaging the microfluidic device or a carrier containing the microfluidic device). The embodiment may further optionally include a cover or lid. In some embodiments, attachment of a microfluidic device to the perfusion disposable is through an engagement with the skirt. However, in other embodiments, attachment is achieved directly with the assembly (without the skirt or other outward extension). In one embodiment, the projecting member or skirt is engaged with a microfluidic chip. In one embodiment, the microfluidic chip comprises a top channel, a bottom channel, and a membrane separating at least a portion of said top and bottom channels. In one embodiment, the microfluidic device comprises cells on the membrane and/or in or on the channels.

In one embodiment, the present invention contemplates a perfusion manifold assembly, comprising i) one or more fluid reservoirs, ii) a fluidic backplane positioned under, and in fluidic communication with, said fluid reservoirs, said fluidic backplane comprising a fluid resistor and fluid channels that terminate at ports, and iii) a projecting member or skirt having one or more side tracks. In one embodiment, the ports are positioned at the bottom of the fluidic backplane. In one embodiment, said one or more side tracks are configured for engaging a microfluidic device positioned in a microfluidic device carrier having one or more outer edges configured to slidably engage said one or more side tracks. In one embodiment of slidably engaging, the linking approach to the perfusion manifold comprises 1) a sliding action, 2) a pivoting movement, and 3) a snap fit so as to provide alignment and fluidic connection in a single action.

In the 1) sliding step, the chip (or other microfluidic device) is in the carrier, which slides along to align the fluidic ports. In the 2) pivot step, the carrier and chip (or other microfluidic device) is pivoted until ports come into fluid contact. In the 3) clip or snap fit step, the force needed to provide a secure seal is provided. In one embodiment, the projecting member or skirt is engaged with a microfluidic chip. In one embodiment, the microfluidic chip comprises a top channel, a bottom channel, and a membrane separating at least a portion of said top and bottom channels. In one embodiment, the microfluidic device comprises cells on the membrane and/or in or on the channels.

In one embodiment, the carrier has a cutout or "window" (e.g. a transparent window) for imaging (e.g. with a microscope) the cells within the microfluidic chip. In one embodiment, there is a corresponding cutout or window (e.g. transparent) in the perfusion disposable. In one embodiment, the microfluidic device comprises features of the carrier to avoid the need for a separate substrate. In one embodiment, the microfluidic device comprises a top channel, a bottom channel, and a membrane separating at least a portion of said top and bottom channels. In one embodiment, the microfluidic device comprises cells on the membrane and/or in or on the channels.

In one embodiment, the present invention contemplates a perfusion manifold assembly, comprising i) one or more fluid reservoirs, ii) a fluidic backplane positioned under, and in fluidic communication with, said fluid reservoirs, said fluidic backplane comprising a fluid resistor and fluid channels that terminate at iii) a projecting member or skirt having one or more fluid ports and one or more side tracks. In one embodiment, said one or more side tracks are configured for engaging a microfluidic device positioned in a microfluidic device carrier having one or more outer edges configured to slidably engage said one or more side tracks. In one embodiment of slidably engaging, the linking approach to the perfusion manifold comprises 1) a sliding action, 2) a pivoting movement, and 3) a snap fit so as to provide alignment and fluidic connection in a single action. In the 1) sliding step, the chip (or other microfluidic device) is in the carrier, which slides along to align the fluidic ports. In the 2) pivot step, the carrier and chip (or other microfluidic device) is pivoted until ports come into fluid contact. In the 3) clip or snap fit step, the force needed to provide a secure seal is provided. In one embodiment, the microfluidic device comprises features of the carrier to avoid the need for a separate substrate. In one embodiment, the carrier has a cutout or "window" (e.g. a transparent window) for imaging (e.g. with a microscope). In one embodiment, there is a corresponding cutout or window (e.g. transparent) in the perfusion disposable (e.g. in the fluid layer). In one embodiment, the present invention contemplates control of the focal plane position and alignment (flatness vs. the microscope stage) at which the chip sits. It is preferred that the required working distance for imaging be minimized (since larger working distances put more burden on the objective). It is not intended that the present invention be limited by the imaging approach; imaging can be upright (objective from above) or inverted (objective from the bottom). While certain embodiments have a cutout or window on only one side for certain imaging modalities (e.g. epifluorescence), in a preferred embodiment the present invention contemplates cutouts or windows on both sides of the chip to enable transmitted light imaging. In one embodiment, said resistor comprises serpentine channels. In one embodiment, said fluidic backplane is made of Cyclo Olefin Polymer (COP) (such as Zeonor 1420R, which is commercially available) and comprises linear fluid channels in fluidic communication with said serpentine channels, said linear channels terminating at one or more ports. In one embodiment, the skirt is made from polycarbonate (PC). In one embodiment, the assembly further comprising a cover for said fluid reservoirs, wherein said cover comprises a plurality of ports optionally associated with filters. In some embodiments, the cover ports comprise through-holes and filters positioned above corresponding holes in a gasket. In some embodiments, the cover comprises one or more channels that route one or more of the ports (such that the port is not a simple through-hole). In one embodiment, said side track comprises a closed first end proximal to said reservoirs and an opened second end distal to said reservoirs, said opened end comprising an angled slide for engaging said one or more outer edges of said microfluidic device carrier. In one embodiment, said side track comprises a linear region between said closed first end and said opened second end. In one embodiment, the projecting member or skirt is engaged with a microfluidic chip. In one embodiment, the microfluidic chip comprises a top channel, a bottom channel, and a membrane separating at least a portion of said top and bottom channels. In one embodiment, the microfluidic device comprises cells on the membrane and/or in or on the channels.

The present invention also contemplates systems comprising perfusion manifold assemblies. In one embodiment, the present invention contemplates a system, comprising: a) a perfusion manifold assembly, comprising i) one or more fluid reservoirs, ii) a fluidic backplane positioned under, and in fluidic communication with, said fluid reservoirs, and iii) a skirt or other projecting member; and b) a microfluidic device or chip engaged with the perfusion manifold assembly through said skirt. In one embodiment, the microfluidic device is engaged in a detachable manner. In one embodiment, the microfluidic device is engaged in a manner that is not detachable (e.g. a one-time connection) whether through a locking mechanism or by using adhesives (e.g. an adhesive layer to assist with the quality of the fluidic seal). In one embodiment, said skirt has a guide mechanism for engaging said microfluidic device. In one embodiment, the guide mechanism comprises a guide shaft or a hole, groove, orifice or other cavity configured to accept a guide shaft. In one embodiment, said guide mechanism comprises (external or internal) guide tracks. In one embodiment, said guide tracks are side tracks. In one embodiment, said microfluidic device or chip is in a carrier and said carrier is engaged with the perfusion manifold assembly through said side tracks of said skirt. In one embodiment, the microfluidic device has one or more features of a carrier so as to avoid the need for an additional substrate such as a carrier. In one embodiment, the microfluidic device comprises a top channel, a bottom channel, and a membrane separating at least a portion of said top and bottom channels. In one embodiment, the microfluidic device comprises cells on the membrane and/or in or on the channels. In one embodiment, the assembly further comprising a cover or cover assembly for said fluid reservoirs, wherein said cover comprises a plurality of ports optionally associated with filters. In some embodiments, the cover ports comprise through-holes and filters positioned above corresponding holes in a gasket. In some embodiments, the cover comprises one or more channels that route one or more of the ports (such that the port is not a simple through-hole).

In one embodiment, the present invention contemplates a system, comprising: a) a perfusion manifold assembly, comprising i) one or more fluid reservoirs, ii) a fluidic backplane positioned under, and in fluidic communication with, said fluid reservoirs, said fluidic backplane comprising a fluid resistor and fluid channels that terminate at fluid outlet ports at the bottom of said backplane, and iii) a skirt or other projecting member having one or more side tracks; and b) a microfluidic device positioned in a carrier, said carrier having one or more outer edges, said outer edges detachably engaging said one or more side tracks of said skirt, said microfluidic device comprising i) microchannels in fluidic communication with said perfusion manifold assembly via ii) one or more inlet ports on a iii) mating surface, wherein said one or more fluid inlet ports of said microfluidic device are positioned against said one or more fluid outlet ports of said perfusion manifold assembly under conditions such that fluid flows from said fluid reservoirs of said perfusion manifold assembly through said one or more fluid outlet ports into said one or more fluid inlet ports of said microfluidic device. In one embodiment, the carrier is engaged in a detachable manner. In one embodiment, the carrier is engaged in a manner that is not detachable (e.g. a one-time connection) whether through a locking mechanism or by using adhesives (e.g. an adhesive layer to assist with the quality of the fluidic seal). In one embodiment, the microfluidic device comprises a top channel, a bottom channel, and a membrane separating at least a portion of said top and bottom channels. In one embodiment, the microfluidic device comprises cells on the membrane and/or in or on the channels. In one embodiment, the assembly further comprising a cover for said fluid reservoirs, wherein said cover comprises a plurality of openings associated with channels. In one embodiment, the assembly further comprising a cover for said fluid reservoirs, wherein said cover comprises a plurality of ports optionally associated with filters. In some embodiments, the cover ports comprise through-holes and filters positioned above corresponding holes in a gasket. In some embodiments, the cover comprises one or more channels that route one or more of the ports (such that the port is not a simple through-hole).

In one embodiment, the present invention contemplates a system, comprising: a) a perfusion manifold assembly, comprising i) one or more fluid reservoirs, ii) a fluidic backplane positioned under, and in fluidic communication with, said fluid reservoirs, said fluidic backplane comprising a fluid resistor and fluid channels that terminate at iii) a skirt having one or more fluid outlet ports and one or more side tracks; and b) a microfluidic device positioned in a carrier, said carrier having one or more outer edges, said outer edges detachably engaging said one or more side tracks of said skirt, said microfluidic device comprising i) micro channels in fluidic communication with said perfusion manifold assembly via ii) one or more inlet ports on a iii) mating surface, wherein said one or more fluid inlet ports of said microfluidic device are positioned against said one or more fluid outlet ports of said skirt of said perfusion manifold assembly under conditions such that fluid flows from said fluid reservoirs of said perfusion manifold assembly through said one or more fluid outlet ports into said one or more fluid inlet ports of said microfluidic device. In one embodiment, the microfluidic device comprises a top channel, a bottom channel, and a membrane separating at least a portion of said top and bottom channels. In one embodiment, the microfluidic device comprises cells on the membrane and/or in or on the channels. In a preferred embodiment, said microfluidic device comprises living cells perfused with fluid from said fluid reservoirs. In one embodiment, the assembly further comprising a cover for said fluid reservoirs, wherein said cover comprises a plurality of ports optionally associated with filters. In some embodiments, the cover ports comprise through-holes and filters positioned above corresponding holes in a gasket. In some embodiments, the cover comprises one or more channels that route one or more of the ports (such that the port is not a simple through-hole).

In a particularly preferred embodiment, said microfluidic device or chip (whether positioned in a carrier or not) comprises at least two different cell types that function together in a manner that mimic one or more functions of cells in an organ in the body. In one embodiment, the microfluidic device comprises a membrane having top and bottom surfaces, said top surface comprising a first cell type, said bottom surface comprises a second cell type. In one embodiment, the microfluidic device comprises a top channel, a bottom channel, and a membrane separating at least a portion of said top and bottom channels. In one embodiment, said first cell type is epithelial cells and said second cell type is endothelial cells. In a preferred embodiment, said membrane is porous (e.g. porous to fluid, gases, cytokines and other molecules, and, in some embodiments, porous to cells, permitting cells to transmigrate the membrane).

In one embodiment, the present invention contemplates a method of seeding cells into a microfluidic chip (e.g. having ports associated with one or more microfluidic channels), the method comprising a) providing i) a chip at least partially contained in a carrier, ii) cells, iii) a seeding guide and iv) a stand with portions configured to accept at least one seeding guide in a stable mounted position; b) engaging said seeding guide with said carrier to create an engaged seeding guide; c) mounting said engaged seeding guide on said stand, and d) seeding said cells into said chip while said seeding guide is in a stable mounted position. In one embodiment, the seeding guide is configured (e.g. with guide tracks) to engage the edges of said carrier. In one embodiment, the seeding guide has side tracks (similar or identical to those in the skirt of one embodiment of the perfusion manifold assembly) to engage the edges of said carrier. In one embodiment of this method, a plurality of seeding guides are mounted on the stand, permitting a plurality of chips to be seeded with cells. In one embodiment, the microfluidic chip comprises a top channel, a bottom channel, and a membrane separating at least a portion of said top and bottom channels. In one embodiment, the microfluidic chip, after said seeding, comprises cells on the membrane and/or in or on the channels. In one embodiment, the method further comprises, after said seeding of step d), the steps of e) disengaging said carrier from said seeding guide and f) engaging said perfusion manifold assembly with said carrier comprising said microfluidic chip comprising cells.

In one embodiment, the present invention contemplates a method of seeding cells into a microfluidic chip (e.g. having ports associated with one or more microfluidic channels), the method comprising a) providing i) a chip at least partially contained in a seeding guide, ii) cells and iii) a stand with portions configured to accept at least one seeding guide in a stable mounted position; b) engaging said stand with said seeding guide; and c) seeding said cells into said chip while said seeding guide is in a stable mounted position. In one embodiment of this method, a plurality of seeding guides is engaged with said stand, permitting a plurality of chips to be seeded with cells. In one embodiment of this method, there is no chip carrier. In another embodiment, the chip carrier serves as the seeding guide (without a separate seeding guide structure engaging the carrier).

In a preferred embodiment, said carrier further comprises a locking mechanism for restricting movement of the carrier when said one or more fluid inlet ports of said microfluidic device are positioned against said one or more fluid outlet ports of said perfusion manifold assembly. It is not intended that the present invention be limited to the nature of the locking mechanism. In one embodiment, the locking mechanism is selected from the group consisting of a clip, a clamp, a stud, and a screw. In one embodiment, the locking mechanism engages in a friction fit. The locking mechanism can permit either detachable engagement or engagement that is not detachable.

The present invention also contemplates methods of perfusing cells utilizing a perfusion manifold assembly. In one embodiment, the present invention contemplates a method of perfusing cells, comprising: A) providing a) a perfusion manifold assembly comprising i) one or more fluid reservoirs, ii) a fluidic backplane positioned under, and in fluidic communication with, said fluid reservoirs, said fluidic backplane comprising fluid channels that terminate at outlet ports, and iii) a skirt or other projecting member comprising a guide mechanism; and b) a microfluidic device positioned in a carrier, said carrier configured to engage said guide mechanism of said skirt, said microfluidic device comprising i) living cells, and ii) microchannels in fluidic communication with ii) one or more inlet ports on a iii) mating surface; B) positioning said carrier such that engages of said guide mechanism of said skirt; and C) moving said carrier until said one or more fluid inlet ports of said microfluidic device are positioned against said one or more fluid outlet ports of said perfusion manifold assembly under conditions such that said microfluidic device is linked and fluid flows from said fluid reservoirs of said perfusion manifold assembly through said one or more fluid outlet ports into said one or more fluid inlet ports and into said microchannels of said microfluidic device, thereby perfusing said cells. In one embodiment, the fluidic backplane comprises a fluid resistor. In one embodiment, the guide mechanism comprises a guide shaft or a hole, groove, orifice or other cavity configured to accept a guide shaft. In one embodiment, the guide mechanism comprises (external or internal) guide tracks. In one embodiment, said guide tracks are side tracks. In one embodiment, said carrier comprises one or more outer edges, said outer edges configured for engaging said one or more side tracks of said skirt. In one embodiment, the moving of step C) comprises sliding said carrier along said side tracks until said inlet and outlet ports are positioned against each other. In one embodiment, said one or more inlet ports on said mating surface of said microfluidic device comprise droplets protruding above said mating surface and one or more outlet ports on said perfusion manifold comprise protruding droplets, such that sliding of step C) causes a droplet-to-droplet connection. In one embodiment, said carrier is engaged in a detachable fashion. In another embodiment, said carrier is engaged in a manner that is not detachable (e.g. one time connection). In one embodiment, the assembly further comprising a cover or lid for said fluid reservoirs, wherein said cover comprises a plurality of ports optionally associated with filters. In some embodiments, the cover ports comprise through-holes and filters positioned above corresponding holes in a gasket. In some embodiments, the cover comprises one or more channels that route one or more of the ports (such that the port is not a simple through-hole).

In one embodiment, the present invention contemplates a method of perfusing cells, comprising: A) providing a) a perfusion manifold assembly comprising i) one or more fluid reservoirs, ii) a fluidic backplane positioned under, and in fluidic communication with, said fluid reservoirs, said fluidic backplane comprising a fluid resistor and fluid channels that terminate at iii) a skirt having one or more fluid outlet ports and one or more side tracks; and b) a microfluidic device positioned in a carrier, said carrier having one or more outer edges, said outer edges configured for detachably engaging said one or more side tracks of said skirt, said microfluidic device comprising i) living cells, and ii) microchannels in fluidic communication with ii) one or more inlet ports on a iii) mating surface; B) positioning said carrier such that said one or more outer edges engage said one or more side tracks of said skirt; and C) sliding said carrier along said side track until said one or more fluid inlet ports of said microfluidic device are positioned against said one or more fluid outlet ports of said skirt of said perfusion manifold assembly under conditions such that said microfluidic device is linked and fluid flows from said fluid reservoirs of said perfusion manifold assembly through said one or more fluid outlet ports into said one or more fluid inlet ports and into said microchannels of said microfluidic device, thereby perfusing said cells. In one embodiment, said one or more inlet ports on said mating surface of said microfluidic device comprise droplets protruding above said mating surface and one or more outlet ports on said skirt comprise protruding droplets, such that sliding of step C) causes a droplet-to-droplet connection when one or more fluid inlet ports of said microfluidic device are positioned against said one or more fluid outlet ports of said skirt of said perfusion manifold assembly.

In one embodiment, said droplet-to-droplet connection does not permit air to enter said one or more fluid inlet ports. In one embodiment, the mating surface proximate to said droplets is hydrophobic.

In one embodiment, the method, further comprises the step of activating a locking mechanism for restricting movement of the carrier. In one embodiment, the method further comprises the step of placing said perfusion manifold assembly with said linked microfluidic device in an incubator.

In one embodiment, the method (as described for any of the embodiments of the perfusing method above) further comprises the step of placing said perfusion manifold assembly with said linked microfluidic device on, within or in contact with, a culture module. In one embodiment, said fluid reservoirs of said perfusion manifold assembly are covered with a cover assembly comprising a cover having a plurality ports, and said culture module comprises a mating surface with pressure points that correspond to the ports on the cover, such that the step of placing of said perfusion manifold assembly with said linked microfluidic device in or on said culture module results in contact of said ports with said pressure points. In one embodiment, said fluid reservoirs of said perfusion manifold assembly are covered with a cover assembly comprising a cover having a plurality ports, and said culture module comprises a mating surface with pressure points that correspond to the ports on the cover, such that after the step of placing of said perfusion manifold assembly with said linked microfluidic device in or on said culture module, the pressure points of the mating surface of the culture module are brought into contact with said through-holes of the cover assembly. In one embodiment, said fluid reservoirs of said perfusion manifold assembly are covered with a cover assembly comprising a cover having a plurality of through-hole ports associated with filters and corresponding holes in a gasket, and said culture module comprises a mating surface with pressure points that correspond to the through-hole ports on the cover, such that the step of placing of said perfusion manifold assembly with said linked microfluidic device on said culture module results in contact of said through-holes with said pressure points. In one embodiment, the fluid reservoirs of said perfusion manifold assembly are covered with a cover assembly comprising a cover having a plurality of through-hole ports associated with filters and corresponding holes in a gasket, and said culture module comprises a mating surface with pressure points that correspond to the through-hole ports on the cover, such that after the step of placing of said perfusion manifold assembly with said linked microfluidic device in or on said culture module, the pressure points of the mating surface of the culture module are brought into contact with said through-holes of the cover assembly.

In one embodiment, said culture module comprises volumetric controllers. In one embodiment, said volumetric controllers apply pressure to said fluid reservoirs via said pressure points corresponding to said ports on said cover. In one embodiment, said culture module comprises pressure actuators. In one embodiment, said culture module comprises pressure controllers. In one embodiment, said pressure controllers apply pressure to said fluid reservoirs via said pressure points (e.g. on a pressure manifold) corresponding to said ports (e.g. through-hole ports) on said cover. In one embodiment, said culture module comprises a plurality of perfusion manifold assemblies. In one embodiment, said culture module comprises integrated valves. In one embodiment, said integrated valves are in a pressure manifold. In one embodiment, said valves comprise Schrader valves.

The present invention also contemplates the culture module as a device. In one embodiment, the device comprises an actuation assembly configured to move a plurality of microfluidic devices (such as the perfusion manifold assemblies described herein) against a pressure manifold, said pressure manifold comprising integrated valves. In one embodiment, it is configured to move the microfluidic devices up against a non-moving pressure manifold. In one embodiment, the device comprises an actuation assembly configured to move one or more perfusion manifold assemblies into contact with a pressure manifold. In one embodiment, the device comprises an actuation assembly configured to move a pressure manifold (up or down) into contact with the plurality of perfusion manifold assemblies. In some embodiments, said pressure manifold comprises integrated valves and elastomeric membranes. In some embodiments, the elastic/pliable seal is disposed on the pod or lid and not on the pressure manifold. In either embodiment, the present invention is not intended to be limited to a membrane, since a membrane is only one specific way to do this; in other embodiments, o-rings, gaskets (thicker than a membrane), pliable materials, or vacuum grease are used instead. In one embodiment, the said valves comprise Schrader valves. In some embodiments, the pressure manifold is adapted to sense the presence of a coupled perfusion manifold assembly or microfluidic device, for example, in order to reduce the leakage of pressure or fluid in the absence of a coupled device. Importantly, the pressure manifold, in a preferred embodiment, takes the few pressure sources and disperses them to every perfusion manifold assembly. In some embodiments, the pressure manifold is also designed to directly align with the perfusion manifold assemblies (e.g. via alignment features in the pressure manifold mating surface). In one embodiment, the perfusion manifold assemblies slide into alignment features on the bottom of the pressure manifold that make sure the seals in the pressure manifold are always aligned with the ports on the perfusion manifold assemblies. In some embodiments, the pressure manifold has a set of springs that push down on the perfusion manifold assemblies when the pressure manifold is actuated. These springs force the lid up against the reservoir of the perfusion manifold assembly to create the seal that holds pressure (and avoids leaks) within the perfusion manifold assembly when pressure is passed through the lid ports.

The present invention also contemplates the culture module and the perfusion disposables (PDs) as a system. In one embodiment, the system comprises a device comprising an actuation assembly configured to move a plurality of microfluidic devices (such as the perfusion manifold assemblies described herein) against a pressure manifold, said pressure manifold comprising integrated valves. In one embodiment, it is configured to move the microfluidic devices up against a non-moving pressure manifold. In one embodiment, the system comprises a) device, comprising an actuation assembly configured to move b) a plurality of microfluidic devices (such as the perfusion disposables) into contact with a pressure manifold. In one embodiment, the system comprises a) device, comprising an actuation assembly configured to move a pressure manifold, said pressure manifold comprising integrated valves and seals (e.g. elastomeric membranes), said seals (e.g. elastomeric membranes) in contact with b) a plurality of microfluidic devices. In one embodiment, said microfluidic devices are perfusion disposables. In some embodiments, the elastic/pliable seal is disposed on the pod or lid and not on the pressure manifold. In either embodiment, the present invention is not intended to be limited to a membrane, since a membrane is only one specific way to do this; in other embodiments, o-rings, gaskets (thicker than a membrane), pliable materials, or vacuum grease are used instead. In one embodiment, said valves comprise Schrader valves. In one embodiment, the manifold uses a bi-stable engagement mechanism so that the actuator does not need to be always on to provide engagement and continuous pressure to the lid. In a bi-stable mechanism, the actuator engages the manifold and then can be turned off. This is useful in situations where the actuator might generate excessive heat while powered for long periods of time. In one embodiment, the perfusion disposable is engaged with a microfluidic chip. In one embodiment, the microfluidic chip comprises a top channel, a bottom channel, and a membrane separating at least a portion of said top and bottom channels. In one embodiment, the microfluidic device comprises cells on the membrane and/or in or on the channels.

The present invention also contemplates drop-to-drop connection schemes for putting a microfluidic device in fluidic communication with a fluid source or another device, including but not limited to, putting a microfluidic device in fluidic communication with the perfusion manifold assembly. In one embodiment, the present invention contemplates a fluidic device comprising a substrate having a first surface, said first surface comprising one or more fluidic ports, wherein said first surface is adapted to stably retain one or more liquid droplets comprising a first liquid at the one or more fluidic ports. In one embodiment, said first surface comprises one or more regions surrounding the one or more fluidic ports, and wherein said regions are adapted to resist wetting by said first liquid. In one embodiment, said regions are adapted to be hydrophobic. In one embodiment, said one or more regions comprise a first material selected to resist wetting by said first liquid. It is not intended that the present invention be limited by any particular first material. However, in one embodiment, the first material is selected from the group consisting of poly-tetrafluoroethylene (PTFE), a perfluoroalkoxy alkane (PFA), fluorinated ethylenepropylene (FEP), polydimethylsiloxane (PDMS), nylon (some grades are hydrophilic and some are hydrophobic), polypropylene, polystyrene and polyimide. In one embodiment, the substrate comprises said first material. In one embodiment, said first material is bonded, adhered, coated or sputtered onto said first surface. In one embodiment, said first material comprises a hydrophobic gasket. In one embodiment, the one or more regions are adapted to resist wetting by said first liquid by means of plasma treatment, ion treatment, gas-phase deposition, liquid-phase deposition, adsorption, absorption or chemical reaction with one or more agents.

In one embodiment, said first surface comprises one or more regions surrounding the one or more fluidic ports, and wherein said regions are adapted to promote wetting by said first liquid. In one embodiment, said regions are adapted to be hydrophilic. In one embodiment, said one or more regions comprise a first material selected to promote wetting by said first liquid. Again, it is not intended that the present invention be limited to any particular first material. However, in one embodiment, the first material is selected from the group consisting of polymethylmethacrylate (PMMA), polyvinyl alcohol (PVOH), polycarbonate (PC), polyether ether ketone (PEEK), polyethylene terephthalate (PET), polyfulfone, polystyrene, polyvinyl acetate (PVA), nylon, polyvinyl fluoride (PVF), polyvinylidiene chloride (PVDC), polyvinyl chloride (PVC) and acrylonitrile-butadiene-styrene (ABS). In one embodiment, the substrate comprises said first material. In one embodiment, said first material is bonded, adhered, coated or sputtered onto said first surface. In one embodiment, said first material comprises a hydrophilic gasket. In one embodiment, the one or more regions are adapted to promote wetting by said first liquid by means of plasma treatment, ion treatment, gas-phase deposition, liquid-phase deposition, adsorption, absorption or chemical reaction with one or more agents.

In one embodiment, the first surface comprises one or more ridges surrounding the one or more fluidic ports. In one embodiment, the first surface comprises one or more recesses surrounding the one or more fluidic ports. In one embodiment, said first surface is adapted to stably retain one or more aqueous liquid droplets. In one embodiment, said first surface is adapted to stably retain one or more non-aqueous liquid droplets. In one embodiment, said first surface is adapted to stably retain one or more oil droplets.

The present invention also contemplates systems comprising devices that retain droplets. In one embodiment, the system comprises: a) a first substrate comprising a first surface, said first surface comprising a first set of one or more fluidic ports, wherein said first surface is adapted to stably retain one or more liquid droplets comprising a first liquid at the first set of fluidic ports, b) a second substrate comprising a second surface, said second surface comprising a second set of one or more fluidic ports, and c) a mechanism for fluidically contacting (and connecting) the first set of fluidic ports to the second set of fluidic ports.

The present invention also contemplates methods of retaining droplets so that they can be combined to establish a fluidic connection. In one embodiment, a method for establishing a fluidic connection is contemplated, comprising: a) providing a first substrate comprising a first surface, said first surface comprising a first set of one or more fluidic ports, wherein said first surface is adapted to stably retain one or more liquid droplets comprising a first liquid at the first set of fluidic ports, b) providing a second substrate comprising a second surface, said second surface comprising a second set of one or more fluidic ports, and c) contacting the first set of fluidic ports and the second set of fluidic ports (e.g. via a controlled engagement). In a preferred embodiment, the contacting of step c) comprises aligning the first set of fluidic ports and the second set of fluidic ports and bringing the aligned sets of ports into contact.

In one embodiment, the present invention contemplates systems and methods where a microfluidic device is brought into contact with a fluid source in a drop-to-drop connection. In one embodiment, the present invention contemplates a method, comprising: a) providing i) a fluid source in fluidic communication with a first fluid port positioned on a first mating surface, said first fluid port comprising a first protruding fluid droplet; ii) a microfluidic device comprising a microchannel in fluidic communication with an second fluid port on a second mating surface, said second fluid port comprising a second protruding fluid droplet; and b) bringing said first protruding fluid droplet and said second fluid droplet together in a droplet-to-droplet connection, so that fluid can flow from said fluid source through said first fluid port into said second fluid port of said microfluidic device. In one embodiment, the present invention contemplates a system, comprising: a) a fluid source in fluidic communication with a first fluid port positioned on a first mating surface, said first fluid port adapted to support a first protruding fluid droplet; b) a microfluidic device comprising a microchannel in fluidic communication with an second fluid port on a second mating surface, said second fluid port adapted to support a second protruding fluid droplet; and c) a mechanism for bringing said first protruding fluid droplet and said second fluid droplet together in a droplet-to-droplet connection, so that fluid can flow from said fluid source through said first fluid port into said second fluid port of said microfluidic device. In one embodiment, the first protruding fluid droplet protrudes downward from said first mating surface and said second protruding fluid droplet protrudes upward from said second mating surface. In one embodiment, the first protruding fluid droplet protrudes upward from said first mating surface and said second protruding fluid droplet protrudes downward from said second mating surface. In one embodiment, said mechanism lifts the second mating surface upward into contact with said first mating surface. In another embodiment, said mechanism lifts the first mating surface upward into contact with said second mating surface. In still another embodiment, said mechanism lowers the second mating surface into contact with said first mating surface. In yet another embodiment, said mechanism lowers the first mating surface into contact with said second mating surface.

In one embodiment, the present invention contemplates that droplets are controlled by surface treatments. In one embodiment of the system, said first mating surface comprises a region surrounding said first fluid port, and wherein said region is adapted to resist wetting by said fluid. In one embodiment said region is adapted to be hydrophobic. In one embodiment, said region comprises a first material selected to resist wetting by said fluid. It is not intended that the present invention be limited by the nature of the first material. However, in one embodiment, the first material is selected from the group consisting of poly-tetrafluoroethylene (PTFE), a perfluoroalkoxy alkane (PFA), fluorinated ethylenepropylene (FEP), polydimethylsiloxane (PDMS), nylon (some grades are hydrophobic), polypropylene, polystyrene and polyimide. It is not intended that the present invention be limited by the nature by which the first material is attached to the surface. However, in one embodiment, said first material is bonded, adhered, coated or sputtered onto said first mating surface. The present invention also contemplates adding features with intrinsic hydrophobic surfaces, or surfaces that can be made hydrophobic. In one embodiment, said first material comprises a hydrophobic gasket. It is not intended that the present invention be limited by the particular treatment regime use to modify surfaces, or regions of surfaces. However, in one embodiment, said region of said first mating surface is adapted to resist wetting by means of plasma treatment, ion treatment, gas-phase deposition, liquid-phase deposition, adsorption, absorption or chemical reaction with one or more agents.

While an embodiment has been discussed above for adapting surfaces or regions of surfaces to resist wetting, the present invention contemplates embodiments wherein said first mating surface comprises a region surrounding said first fluid port, and wherein said region is adapted to promote wetting by said fluid. In one embodiment, said region is adapted to be hydrophilic. In one embodiment, said region comprises a first material selected to promote wetting by said first liquid. It is not intended that the present invention be limited to particular first materials for promoting wetting. However, in one embodiment, the first material is selected from the group consisting of polymethylmethacrylate (PMMA), polyvinyl alcohol (PVOH), polycarbonate (PC), polyether ether ketone (PEEK), polyethylene terephthalate (PET), polyfulfone, polystyrene, polyvinyl acetate (PVA), nylon (certain grades are hydrophilic), polyvinyl fluoride (PVF), polyvinylidiene chloride (PVDC), polyvinyl chloride (PVC) and acrylonitrile-butadiene-styrene (ABS). It is also not intended that the present invention be limited by the technique for attaching the first material to the surface. However, in one embodiment, said first material is bonded, adhered, coated or sputtered onto said first mating surface. The present invention also contemplates introducing structures or features with intrinsic hydrophilic surfaces, or surfaces that can be made hydrophilic. For example, in one embodiment, said first material comprises a hydrophilic gasket. It is also not intended that the present invention be limited to the treatment regime for promoting wetting. For example, in one embodiment, said region of said first mating surface is adapted to promote wetting by means of plasma treatment, ion treatment, gas-phase deposition, liquid-phase deposition, adsorption, absorption or chemical reaction with one or more agents.

The present invention also contemplates structures and geometrical features that can be molded or formed as part of the surface, attached to, deposited on, printed on or bonded to the sources, or machined into, etched into or ablated into the surface. For example, in one embodiment, the first mating surface comprises one or more ridges surrounding said first fluid ports. In another embodiment, the first mating surface comprises one or more recesses surrounding said first fluid port.

The present invention is also not limited to drop-to-drop connections with only aqueous fluids. While in one embodiment, said first mating surface is adapted to stably retain an aqueous protruding fluid droplet, in another embodiment, said first mating surface is adapted to stably retain a non-aqueous protruding fluid droplet, including but not limited to an oil protruding droplet.

The present invention also contemplates method for merging droplets using a drop-to-drop scheme. In one embodiment, the present invention contemplates a method of merging droplets, comprising: a) providing i) a fluid source in fluidic communication with a first fluid port positioned on a first mating surface, said first fluid port comprising a first protruding fluid droplet; and ii) a microfluidic device or chip comprising a microchannel in fluidic communication with a second fluid port on a second mating surface, said second fluid port comprising a second protruding fluid droplet; and b) bringing said first protruding fluid droplet and said second fluid droplet together in a droplet-to-droplet connection, whereby the first and second fluid droplets merge so that fluid flows from said fluid source through said first fluid port into said second fluid port of said microfluidic device. In one embodiment, the microfluidic chip comprises a top channel, a bottom channel, and a membrane separating at least a portion of said top and bottom channels. In one embodiment, the microfluidic device comprises cells on the membrane and/or in or on the channels. It is not intended that the present invention be limited to particular orientations or the two mating surfaces. In one embodiment, the first protruding fluid droplet protrudes downward from said first mating surface and said second protruding fluid droplet protrudes upward from said second mating surface. In another embodiment, the first protruding fluid droplet protrudes upward from said first mating surface and said second protruding fluid droplet protrudes downward from said second mating surface. It is also not intended that the present invention be limited by how the droplets are brought together. In one embodiment, step b) comprises lifting the second mating surface upward into contact with said first mating surface. In another embodiment, step b) comprises lifting the first mating surface upward into contact with said second mating surface. In yet another embodiment, step b) comprising lowering the second mating surface into contact with said first mating surface. In still another embodiment, step b) comprises lowering the first mating surface into contact with said second mating surface. In a preferred embodiment, said droplet-to-droplet connection does not permit air to enter said fluid inlet port.

The present invention contemplates surface treatments to promote wetting. In one embodiment, said first mating surface comprises a region surrounding said first fluid port, wherein said region is adapted to promote wetting by said fluid. In one embodiment, said region is adapted to be hydrophilic. In one embodiment, said region comprises a first material selected to promote wetting by said fluid. While not intended to limit the invention to any particular first material, in one embodiment, the first material is selected from the group consisting of polymethylmethacrylate (PMMA), polyvinyl alcohol (PVOH), polycarbonate (PC), polyether ether ketone (PEEK), polyethylene terephthalate (PET), polyfulfone, polystyrene, polyvinyl acetate (PVA), nylon, polyvinyl fluoride (PVF), polyvinylidiene chloride (PVDC), polyvinyl chloride (PVC) and acrylonitrile-butadiene-styrene (ABS). While not intending to limit the invention to any particular attachment approach, in one embodiment, said first material is bonded, adhered, coated or sputtered onto said first mating surface.

In some embodiments, the present invention contemplates adding features or structures to a surface, including structures with intrinsically hydrophilic surfaces (or surfaces that can be made hydrophilic). In one embodiment, said first material comprises a hydrophilic gasket.

It is not intended that the present invention be limited to any particular surface treatment technique. However, in one embodiment, said region of said first mating surface is adapted to promote wetting by means of plasma treatment, ion treatment, gas-phase deposition, liquid-phase deposition, adsorption, absorption or chemical reaction with one or more agents.

Additional structures can be molded or otherwise formed into or on to the surfaces. For example, in one embodiment, the first mating surface comprises one or more ridges surrounding said first fluid port. In another embodiment, the first mating surface comprises one or more recesses surrounding said first fluid port.

As noted above, the fluid need not be an aqueous fluid. While in one embodiment, the present invention contemplates said first mating surface is adapted to stably retain an aqueous protruding fluid droplet, in another embodiment, said first mating surface is adapted to stably retain a non-aqueous protruding fluid droplet, including but not limited to retaining an oil protruding droplet.

The present invention also contemplates systems for linking ports together. In one embodiment, the system comprises: a) a first substrate comprising a first fluidic port, b) a second substrate comprising a second fluidic port, c) a guide mechanism adapted to align the first port and the second port, and (optionally) d) a retention mechanism adapted to retain the first substrate in contact with the second substrate. While not intending to limiting the invention to any particular guide mechanism, in one embodiment, the guide mechanism is a guide track positioned on said first substrate, said guide track configured to engage a portion of said second substrate. While the present invention contemplates embodiments wherein the retention mechanism is on the first or second substrate, in one embodiment, the retention mechanism is a clip positioned on said second substrate, said clip configured to engage said first substrate.

In another embodiment, the present invention contemplates a system comprising: a) a first substrate comprising a first set of one or more fluidic ports, b) a second substrate comprising a second set of one or more fluidic ports, c) a guide mechanism adapted to align the first set of ports and the second set of ports, and d) a retention mechanism adapted to retain the first substrate in contact with the second substrate. Again, a variety of guide mechanisms are contemplated (and discussed herein). In one embodiment, the guide mechanism comprises a guide shaft or a hole, groove, orifice or other cavity configured to accept a guide shaft. However, in one embodiment, the guide mechanism is a guide track positioned on said first substrate, said guide track configured to engage a portion of said second substrate. Again, a variety of retention mechanisms are contemplated (and described herein). However, in one embodiment, the retention mechanism is a clip positioned on said second substrate, said clip configured to engage said first substrate.

The present invention also contemplates methods for linking ports in a manner such that a fluidic connection is established. In one embodiment, the present invention contemplates a method for establishing a fluidic connection, comprising: a) providing a first substrate comprising a first fluidic port, a second substrate comprising a second fluidic port, and a guide mechanism adapted to guide the second substrate, b) engaging the second substrate with the guide mechanism, c) aligning the first and second sets of fluidic ports by help of the guide mechanism, and d) contacting the first and second fluidic ports to establish a fluidic connection. While a variety of guide mechanisms are contemplated, in one embodiment, said guide mechanism comprises a guide track positioned on said first substrate, said guide track configured to engage a portion of said second substrate. In one embodiment of this method for establishing a fluidic connection, said second substrate comprises a microfluidic device comprising a mating surface, wherein said second fluidic port is positioned on said mating surface and comprises a droplet protruding above said mating surface. In a further embodiment, said first substrate comprises a mating surface, wherein said first fluidic port is positioned on said mating surface and comprises a protruding droplet. Still further in this embodiment, said contacting of step d) causes a droplet-to-droplet connection when said first and second fluidic ports to establish a fluidic connection. It is preferred that said droplet-to-droplet connection does not permit air to enter said one or more fluid inlet ports. While the present invention is not limited to the manner of aligning, in one embodiment, said aligning of step c) comprises sliding the second substrate by means of the guide track. While a variety of designs and conformations for the guide track are contemplated, in one embodiment, said guide track comprises first and second sections, said first section shaped to support the aligning of step c), said second section shaped to support the contacting of step d).

While the present invention contemplates embodiments where the retention mechanism is on the first substrate, in one embodiment, said second substrate comprises a retention mechanism adapted to retain the first substrate in contact with the second substrate. In some embodiments, the retention mechanism automatically engages when the first and second substrates make contact and establish a fluidic connection. However, in one embodiment, the present invention contemplates the active step of e) activating the retention mechanism.

While two substrate systems have been described above, the present invention also contemplates three substrate systems. In one embodiment, the system comprises: a) a first substrate comprising a first fluidic port, b) a second substrate comprising a second fluidic port, c) a third substrate configured to support said second substrate; d) a guide mechanism adapted to align the first port with second port, and e) a retention mechanism means adapted to retain the first substrate in contact with the second substrate.

As noted previously, a variety of guide mechanisms are contemplated (and described herein). In one embodiment, the guide mechanism comprises a guide shaft or a hole, groove, orifice or other cavity configured to accept a guide shaft. One or more guide shafts or other projections can be on one substrate, with one or more holes, grooves, orifices or other cavities on the other substrate configured to accept the one or more guide shafts or other projections. In one embodiment, the guide mechanism comprises a guide track. The guide track(s) can be in any orientation (e.g. coming from above rather than from either side). While the present invention contemplates that the guide mechanism might be attached to the first, second or third substrate, in one embodiment, the guide track is positioned on said first substrate. While the present invention contemplates embodiments wherein either the second or third substrates are have features or structures configured to engage the guide mechanism, in one embodiment, the present invention contemplates that the third substrate comprises edges configured to engage said guide track. In one embodiment, the second substrate comprises edges configured to engage said guide track. While the present invention contemplates embodiments wherein the retention mechanism is positioned on the first or second substrates, in one embodiment, said retention mechanism is positioned on said third substrate. As noted previously, a variety of retention mechanisms are contemplated. In one embodiment, said retention mechanism comprises a clip configured to engage said first substrate. In another embodiment, said retention mechanism comprises a clamp configured to engage said first substrate under conditions such that contact between said first and second substrates is maintained. In yet another embodiment, said retention mechanism comprises a stud configured to engage a hole on said first substrate. In still another embodiment, said retention mechanism engages a portion of said first substrate in a friction fit. In one embodiment, said retention mechanism is selected from the group consisting of an adhesive (including a laminate), a heat stake, and a screw.

While the present invention contemplates systems wherein the components of the systems are described (see above), the present invention also contemplates assemblies, where the components are arranged, attached or connected in certain ways. In one embodiment, the present invention contemplates an assembly, comprising: a) a first substrate comprising a first fluidic port and a guide mechanism, said first substrate positioned against and in contact with b) a second substrate comprising a second fluidic port, wherein said first and second ports are aligned so as to permit fluidic communication, said second substrate supported by c) a carrier, said carrier comprising a portion engaging said guide mechanism of said first substrate. While the present invention contemplates embodiments, where a retention mechanism is positioned on said first or second substrate, in one embodiment, said carrier further comprises a retention mechanism for retaining said contact between said first and second substrates. While a variety of guide mechanisms are contemplated (and described herein), in one embodiment, the guide mechanism comprises a guide track. The present invention is not limited to a single guide track; two or more guide tracks may be employed. For example, in one embodiment the guide track is positioned on one or more sides of said first substrate. In one embodiment, the carrier portion engaging said first substrate comprises one or more edges configured to engage said guide track.

While a variety of retention mechanisms are contemplated (and described herein) in one embodiment of the assembly, said retention mechanism comprises a clip configured to engage said first substrate. In another embodiment, said retention mechanism comprises a clamp configured to engage said first substrate. In yet another embodiment, said retention mechanism comprises a stud configured to engage a hole on said first substrate. In a particular embodiment, said retention mechanism engages a portion of said first substrate in a friction fit. In one embodiment, said retention mechanism is selected from the group consisting of an adhesive (including but not limited to a laminate), a heat stake, and a screw.

The present invention also contemplates methods for establishing a fluidic connection by bringing fluidic ports together where three substrates are involved. In one embodiment, the present invention contemplates a method for establishing a fluidic connection, comprising: a) providing: a first substrate comprising a first fluidic port, a second substrate comprising a second fluidic port, a third substrate configured to support said second substrate, and a guide mechanism; b) aligning said first and second ports with said guide mechanism; and c) contacting said first port with said second port under conditions such that a fluidic connection is established between said first and second substrate. In one embodiment of this three substrate method, said second substrate comprises a microfluidic device comprising a mating surface, wherein said second fluidic port is positioned on said mating surface and comprises a droplet protruding above said mating surface. Further in this embodiment, said first substrate comprises a mating surface, wherein said first fluidic port is positioned on said mating surface and comprises a protruding droplet. Still further in this embodiment, said contacting of step c) causes a droplet-to-droplet connection when said first and second fluidic ports to establish a fluidic connection. It is preferred that said droplet-to-droplet connection does not permit air to enter said one or more fluid inlet ports.

Again, a variety of guide mechanisms are contemplated and described herein. In one embodiment, the guide mechanism comprises a guide track. While the present invention contemplates positioning the guide track on said first, second or third substrates, in a preferred embodiment, the guide track is positioned on said first substrate. In one embodiment, the third substrate comprises edges configured to engage said guide track. While not intending that the invention be limited to the particular technique for aligning, in one embodiment, the present invention contemplates said aligning of step b) comprises sliding said third substrate by means of said guide track. In one embodiment, said guide track comprises first and second sections, said first section shaped to support the aligning of step b), said second section shaped to support the contacting of step c). In one embodiment, said first section is linear and said second section is curved. In yet another embodiment, said guide mechanism comprises a mechanism on which said third substrate rotates or pivots during step d). For example, in one embodiment, said guide mechanism comprises a hinge, joint, or pivot point.

While the present invention contemplates embodiments where the retention mechanism is positioned on the first or second substrates, in one embodiment, the present invention contemplates that said third substrate further comprises a retention mechanism for retaining alignment of said first and second ports. Again, a variety of retention mechanisms are contemplated. In one embodiment, said retention mechanism comprises a clip configured to engage said first substrate. In one embodiment, said retention mechanism comprises a clamp configured to engage said first substrate under conditions such that contact between said first and second substrates is maintained. In yet another embodiment, said retention mechanism comprises a stud configured to engage a hole on said first substrate. In still another embodiment, said retention mechanism engages a portion of said first substrate in a friction fit. In one embodiment, said retention mechanism is selected from the group consisting of an adhesive (including but not limited to a laminate), a heat stake, and a screw. The present invention also contemplates embodiments wherein the third substrate is a carrier for the second substrate.

In one embodiment, the present invention contemplates a method for establishing a fluidic connection, comprising: a) providing: a first substrate comprising a guide mechanism and a first fluidic port on a first mating surface, a second substrate comprising a second fluidic port on a second mating surface and a bottom surface, and a carrier in contact with said bottom surface of said second substrate, said carrier comprising a retention mechanism and one or more edges for engaging said guide mechanism; b) engaging said guide mechanism of said first substrate with one or more edges of said carrier; c) aligning said first and second ports with said guide mechanism; d) contacting said first mating surface with said second mating surface under conditions such that said first port contacts said second port and a fluidic connection is established between said first and second substrate. In one embodiment of this method, said second fluidic port comprises a droplet protruding above said mating surface of said second substrate. In one embodiment, said first fluidic port comprises a protruding droplet. In one embodiment, said contacting of step d) causes a droplet-to-droplet connection when said first and second fluidic ports to establish a fluidic connection. It is preferred that said droplet-to-droplet connection does not permit air to enter said one or more fluid inlet ports. While a variety of guide mechanisms are contemplated, in one embodiment, the guide mechanism comprises a guide track. The present invention is not limited to embodiments where there is only one guide track; two or more guide tracks may be used. In one embodiment, the guide track is positioned on one or more sides of said first substrate. In a preferred embodiment, the carrier comprises one or more edges configured to engage said guide track. While a variety of aligning approaches are contemplated, in one embodiment, said aligning of step c) comprises sliding said carrier by means of said guide track. While a variety of designs and configurations for the guide track are contemplated, in one embodiment, said guide track comprises first and second sections, said first section shaped to support the aligning of step c), said second section shaped to support the contacting of step d). In one embodiment, said first section is linear and said second section is curved. In yet another embodiment, said guide mechanism comprises a mechanism on which said carrier rotates or pivots during step d). In this embodiment, said guide mechanism may comprise a hinge, a joint, a socket or other pivot point.

In some embodiments, the retention mechanism automatically engages when or after contact is made in step d). However, in one embodiment, the present invention contemplates the active step of e) activating said retention mechanism under condition such that said alignment of said first and second ports is retained. Again, a variety of retention mechanisms are contemplated. In one embodiment, said retention mechanism comprises a clip configured to engage said first substrate. In one embodiment, said retention mechanism comprises a clamp configured to engage said first substrate under conditions such that contact between said first and second substrates is maintained. In one embodiment, said retention mechanism comprises a stud configured to engage a hole on said first substrate. In one embodiment, said retention mechanism engages a portion of said first substrate in a friction fit. In one embodiment, said retention mechanism is selected from the group consisting of an adhesive (including but not limited to a laminate, a heat stake, and a screw).

The present invention also contemplates devices for perfusing cells, including devices that apply pressure to fluid reservoirs to create a flow of fluid (e.g. culture media). The present invention contemplates, in one embodiment, a device, comprising an actuation assembly configured to move a pressure manifold, said pressure manifold comprising integrated valves. In one embodiment, said device further comprises elastomeric membranes. In one embodiment, said valves comprise Schrader valves. In one embodiment, said pressure manifold comprises a mating surface with pressure points. In one embodiment, the device further comprises pressure controllers. In one embodiment, said pressure controllers are configured to apply pressure via said pressure points. In one embodiment, said actuation assembly comprises pneumatic cylinder operably linked to said pressure manifold. In one embodiment, said mating surface further comprises alignment features configured to align a microfluidic device or chip when said microfluidic device or chip engages said mating surface. In one embodiment, said device is a culture module for perfusing cells. In one embodiment, the microfluidic chip is engaged with a perfusion manifold assembly (and the alignment features are configured to align the perfusion manifold assembly). In one embodiment, the microfluidic chip comprises a top channel, a bottom channel, and a membrane separating at least a portion of said top and bottom channels. In one embodiment, the microfluidic device comprises cells on the membrane and/or in or on the channels.

The present invention also contemplates systems where a device for delivering pressure is linked to a plurality of microfluidic devices, and more preferably, the plurality of microfluidic devices (such as the various embodiments of the perfusion disposables discussed herein) are simultaneously linked (although they can be linked individually or sequentially, if desired). In one embodiment, the present invention contemplates a system, comprising a) device comprising an actuation assembly configured to move a pressure manifold, said pressure manifold comprising integrated valves, said pressure manifold in contact with b) a plurality of microfluidic devices (such as the various embodiments of the perfusion disposables discussed herein). In one embodiment, said pressure manifold further comprises elastomeric membranes, and said elastomeric membranes are in contact with said microfluidic devices. In one embodiment, said microfluidic devices are perfusion disposables. In one embodiment, said valves comprise Schrader valves. In one embodiment, each of said microfluidic devices is covered with a cover assembly comprising a cover having a plurality of ports, and said pressure manifold comprising a mating surface with pressure points that correspond to the ports on the cover, wherein the pressure points of the mating surface of the pressure manifold are in contact with said ports of the cover assembly. In one embodiment, said ports comprise through-hole ports associated with filters and corresponding holes in a gasket. In one embodiment, the device further comprises pressure controllers. In one embodiment, said pressure controllers are configured to apply pressure via said pressure points. In one embodiment, said actuation assembly comprises pneumatic cylinder operably linked to said pressure manifold. In one embodiment, said mating surface of the pressure manifold further comprises alignment features configured to align a microfluidic device when said microfluidic device engages said mating surface. In a preferred embodiment, said device is a culture module for perfusing cells. In one embodiment of such a culture module, the culture module is configured to accept one or more trays, each tray comprising a plurality of microfluidic devices. In one embodiment, the culture module further comprises a user interface to control said culture module. In one embodiment, each tray comprising a plurality of perfusion manifold assemblies. In one embodiment, a microfluidic chip is engaged with each perfusion manifold assembly (and the alignment features of the pressure manifold mating surface are configured to align each perfusion manifold assembly). In one embodiment, the microfluidic chip comprises a top channel, a bottom channel, and a membrane separating at least a portion of said top and bottom channels. In one embodiment, the microfluidic device comprises cells on the membrane and/or in or on the channels.

The present invention also contemplates methods for perfusing cells (e.g. cells in microchannels of a microfluidic device, such as the various embodiments of the perfusion disposable discussed herein, where cells were first seeded into said microfluidic device, with or without a seeding guide of the type described herein) with a culture module. In one embodiment, the present invention contemplates a method of perfusing cells, comprising: A) providing a) a culture module, said culture module comprising i) an actuation assembly configured to move a plurality of microfluidic devices against ii) a pressure manifold, said pressure manifold comprising a mating surface with pressure points; and b) a plurality of microfluidic devices, each of said microfluidic devices comprising i) one or more microchannels comprising living cells, ii) one or more reservoirs comprising culture media, and iii) a cover assembly above said one or more reservoirs, said cover assembly comprising a cover with ports that correspond to the pressure points on the pressure manifold mating surface; B) placing said plurality of microfluidic devices on or in said culture module; and C) simultaneously (or sequentially) contacting said ports on the cover of each microfluidic device of said plurality of microfluidic devices with said mating surface of said pressure manifold, such that the ports are in contact with said pressure points, under conditions such that culture media flows from said reservoirs into said microchannels of said microfluidic devices, thereby perfusing said cells. In one embodiment, said plurality of microfluidic devices are positioned on one or more trays prior to step B) and said placing of step B) comprising moving at least a subset of said plurality of microfluidic devices simultaneously into said culture module. In one embodiment, said simultaneous contacting of step C) is achieved by moving, via the actuation assembly, the plurality of microfluidic devices up against the mating surface of the pressure manifold. In another embodiment, the present invention contemplates a method of perfusing cells, comprising: A) providing a) a culture module, said culture module comprising i) an actuation assembly configured to move ii) a pressure manifold, said pressure manifold comprising a mating surface with pressure points; and b) a plurality of microfluidic devices, each of said microfluidic devices comprising i) one or more microchannels comprising living (viable) cells, ii) one or more reservoirs comprising culture media, and iii) a cover assembly above said one or more reservoirs, said cover assembly comprising a cover with ports that correspond to the pressure points on the pressure manifold mating surface; B) placing said plurality of microfluidic devices on or in said culture module; and C) simultaneously (or sequentially) contacting said ports on the cover of each microfluidic device of said plurality of microfluidic devices with said mating surface of said pressure manifold, such that the ports are in contact with said pressure points, under conditions such that culture media flows from said reservoirs into said microchannels of said microfluidic devices, thereby perfusing said cells. In the above embodiment, the plurality of microfluidic devices are simultaneously linked. Thereafter, they can be simultaneously de-linked or disconnected from the pressure manifold. In one embodiment, said plurality of microfluidic devices are positioned on one or more trays (or nests) prior to step B) and said placing of step B) comprising moving at least a subset (at least three) of said plurality of microfluidic devices simultaneously into said culture module. In one embodiment, said simultaneous contacting of step C) is achieved by moving, via the actuation assembly, the mating surface of the pressure manifold down onto said cover assemblies of said plurality of microfluidic devices. In one embodiment of the perfusion method, the microfluidic device comprises a microfluidic chip (including but not limited to the microfluidic chip shown in FIG. 3A, with one or more microchannels and ports) engaged in a perfusion manifold assembly, the assembly comprising i) a cover or lid configured to serve as the top of ii) one or more fluid reservoirs, iii) a fluidic backplane under, and in fluidic communication with, said fluid reservoir(s), and iv) a projecting member or skirt that engages the microfluidic chip (directly) or (indirectly through) a carrier containing the microfluidic chip. It is preferred that the perfusing is done at a rate that results in (or maintains) greater than 80%, and more preferably greater than 90%, and most preferably, greater than 95% viability of the cells contained within the microfluidic chip. In one embodiment, the assembly further comprises a capping layer under said fluid reservoir(s). In one embodiment, said fluidic backplane comprises a resistor. In a preferred embodiment, the microfluidic chip environment is maintained to be sterile during said perfusing.

The present invention also contemplates controlling pressure while perfusing cells (e.g. cells in microchannels of a microfluidic device, such as the various embodiments of the perfusion disposable discussed herein, where cells were first seeded into said microfluidic device, with or without a seeding guide of the type described herein), including controlling pressure, in one embodiment, such that it is reliably maintained at 1 pKa (plus or minus 0.5 pKa, and more preferably, plus or minus 0.15 pKa). In one embodiment, the present invention contemplates a method of controlling pressure while perfusing cells, comprising: A) providing a) a plurality of microfluidic devices, each of said microfluidic devices comprising i) one or more microchannels comprising living cells, ii) one or more reservoirs comprising culture media, b) one or more pressure actuators, B) coupling said pressure actuators to at least one of the said reservoirs, the coupling adapted such that actuated pressure modulates the perfusion of at least some of said living cells, C) turning said one or more pressure actuators between two or more pressure setpoints, thereby controlling pressure while perfusing said cells. In another embodiment, the present invention contemplates a method of controlling pressure while perfusing cells, comprising: A) providing a) a culture module, said culture module comprising i) an actuation assembly configured to move ii) a pressure manifold, said pressure manifold comprising a mating surface with pressure points, and iii) one or more pressure controllers to provide pressure to said pressure points; and b) a plurality of microfluidic devices, each of said microfluidic devices comprising i) one or more microchannels comprising living cells, ii) one or more reservoirs comprising culture media, and iii) a cover assembly above said one or more reservoirs, said cover assembly comprising a cover with ports that correspond to the pressure points on the pressure manifold mating surface; B) placing said plurality of microfluidic devices on or in said culture module; C) simultaneously contacting said ports on the cover of each microfluidic device of said plurality of microfluidic devices with said mating surface of said pressure manifold, such that the ports are in contact with said pressure points, under conditions such that culture media flows from said reservoirs into said microchannels of said microfluidic devices, thereby perfusing said cells; and D) turning (or switching) said one or more pressure controllers off for a period of time and on for a period of time (or turning them between two or more setpoints), thereby controlling pressure while perfusing said cells. In one embodiment, the switching is between setpoints 1 kPa and 0.5 kPa to get good resolution within that range. In one embodiment, the switching is at three levels: 2 kPa, 1 kPa and 0 kPa for some advanced method. In one embodiment, said pressure controllers are turned off and on (or between setpoints) in a switching pattern (e.g. they are turned off and on, or between setpoints, repeatedly at defined intervals). In a preferred embodiment, the switching pattern is selected such that the average value of pressure acting liquid in said one or more reservoirs corresponds to a desired value. For cells, the desired value is typically low. For example, in one embodiment, the switching pattern is selected such that the average gas pressure is maintained below 1 kPa. In one embodiment of the method of perfusing and controlling pressure, the microfluidic device comprises a microfluidic chip (including but not limited to the microfluidic chip shown in FIG. 3A, with one or more microchannels and ports) engaged in a perfusion manifold assembly, the assembly comprising i) a cover or lid configured to serve as the top of ii) one or more fluid reservoirs, iii) a fluidic backplane under, and in fluidic communication with, said fluid reservoir(s), and iv) a projecting member or skirt that engages the microfluidic chip (directly) or (indirectly through) a carrier containing the microfluidic chip. It is preferred that the perfusing is done at a rate that results in greater than 80%, and more preferably greater than 90%, and most preferably, greater than 95% viability of the cells contained within the microfluidic chip. In one embodiment, the assembly further comprises a capping layer under said fluid reservoir(s). In one embodiment, said fluidic backplane comprises a resistor. In one embodiment, the ports on the cover or lid are associated with filters. In one embodiment, the filters are 0.2 micron, 0.4 micron or 25 micron filters. In a preferred embodiment, the microfluidic chip environment is maintained to be sterile during said perfusing. In one embodiment, cycling the pressure regulators on and off brings the average value of pressure close to the desired value, but the max and min values seen by the microfluidic device or chip are brought much closer to the desired value by incorporating the resistive filter at the inlet in the lid of the perfusion manifold assembly.

A pressure lid is contemplated as a device that allows for the pressurization of one or more fluid sources (e.g. reservoirs) within or otherwise associated with a microfluidic device. The present invention contemplates, in one embodiment, a pressure lid comprising a plurality of ports configured to engage a pressure manifold. In one embodiment, the ports are associated with filters. In one embodiment, the lid is associated with a gasket. In one embodiment, the pressure lid is movable or removably attached to a microfluidic device to allow improved access to elements (e.g. reservoirs) within. In one embodiment, the present invention contemplates a method comprising a) providing a pressure lid, a microfluidic device comprising a fluid source, and a pressure manifold, wherein the pressure lid comprising a plurality of ports configured to engage a pressure manifold; b) positioning said pressure lid over said fluid source so as to create a positioned pressure lid; and c) engaging said positioned pressure lid with said pressure manifold under conditions such that pressure is applied through said ports such that fluid from said fluid source moves into or through said microfluidic device. In one embodiment, the method further comprising d) disengaging said positioned pressure lid from said pressure manifold. Thereafter, the pressure lid can be (optionally) removed and the microfluidic device can be used without the lid.

The present invention also contemplates a system comprising: a) instrument for interfacing with b) a microfluidic device, said microfluidic device either comprising or in fluidic communication with i) one or more fluid reservoirs and ii) a pressure lid comprising one or more instrument-interface ports and one or more reservoir-interface ports, wherein the pressure lid is adapted to convey pressure between at least one of the instrument-facing ports and at least one of the reservoir-facing ports. In one embodiment, the instrument comprises a (moving or non-moving) pressure manifold. In one embodiment, the one or more fluid reservoirs are disposed in a cartridge, said cartridge in fluidic communication with said microfluidic device. In one embodiment, the one or more fluidic reservoirs are disposed in the said microfluidic device.

The present invention also contemplates, as a device, a pressure lid comprising one or more instrument-interface ports and one or more reservoir-interface ports, wherein the pressure lid is adapted to convey pressure between at least one of the instrument-facing ports and at least one of the reservoir-facing ports, and wherein the pressure lid is adapted to form a pressure interface with at least one fluid reservoir.

The present invention also contemplates, as a device, a pressure lid comprising one or more channels, each channel comprising an instrument-interface end and anreservoir-interface end, the channel configured to convey pressure between an instrument and a fluid reservoir.

BRIEF DESCRIPTION OF THE DRAWINGS

FIG. 2C-2 is a magnified view of one portion of FIG. 2C-1 (circled). In the illustrated embodiment, the cross section shape of the sealing tooth is a trapezoidal shape, but other contemplated embodiments employ other tooth shapes including but not limited to semi-circular, rectangular, polygonal, and triangular. FIG. 2E-1 is a cross-section view of one embodiment of the cover assembly seal in connection with the reservoir, showing the cover gasket and sealing tooth. FIG. 2E-2 is a magnified view of one portion of FIG. 2E-1 (circled). As the pressure manifold (discussed below) engages the cover assembly, the pressure drives the cover assembly (including the cover gasket) onto the sealing tooth, forming seals between each of the reservoir chambers.

FIG. 4A shows a side view of one embodiment of a chip carrier (with the chip inside) approaching (but not yet engaging) a side track of a skirt of one embodiment of the perfusion manifold assembly, the carrier aligned at an angle matching an angled front end portion of the side track, the carrier comprising a retention mechanism configured as a upwardly protecting clip. Without being bound by theory, a suitably large angle permits chip engagement without smearing or premature engagement of liquid droplets present on the chip and/or the perfusion manifold assembly during the insertion and alignment processes. FIG. 4B shows a side view of one embodiment of a chip carrier (with the chip inside) engaging a side track of a skirt of one embodiment of (but not yet linked to) the perfusion manifold assembly.

FIG. 8B is a schematic of another embodiment showing the trays (or racks) inserted within the housing of the culture module, which has a user interface. The illustrated nested design in which (in the present example) a tray carries multiple removable sub-trays provides the user with the flexibility to remove or carry various numbers of PDs depending on use. For example, the user may carry a full tray to a bio-safety cabinet in order to replenish media or collect samples from all PDs in the tray, move a sub-tray of 3 PDs to a microscope stage in order to image them without permitting the remaining PDs from dysregulating in terms of temperature or gas content, or remove or load a single PD for careful inspection or replacement.

FIG. 11D is an interior side view schematic of one embodiment of the pressure manifold (50) showing a plurality of valves (59) in the manifold body, the poppet (65), valve seal (66) and PD cover (11). In operation (to engage the PD), the valve seal (66) deflects with the displacement of the poppet (65).

FIG. 14 is a schematic showing one embodiment of connecting two microfluidic devices, resulting in the introduction of air bubbles into the microchannels.

FIG. 15 is a schematic showing one embodiment of connecting two microfluidic devices (or a microfluidic device to a fluid source) utilizing a drop-to-drop approach, resulting in no air bubbles.

FIG. 22 is a schematic showing a surface modification embodiment.

FIG. 24 is a schematic of one embodiment of a drop-to-drop connection scheme whereby a combination of geometric shapes and surface treatments are used to control the droplet. FIG. 24A shows an embodiment of the microfluidic device or "chip" comprising a fluid channel and ports, having an elevated region at each port (e.g. a pedestal or gasket). FIG. 24B shows the hydrophilic channel filled with fluid where the droplet radius is balanced at each end (i.e. at the port openings). FIG. 24C shows one portion of the microfluidic device of FIG. 24B with an upward projecting droplet (22) approaching (but not yet in contact with) one portion of the mating surface of the perfusion manifold assembly, which also has a projecting droplet (in this case, the droplet (23) is projecting downward). FIG. 24D shows the same portion of the microfluidic device of FIG. 24C with the upward projecting droplet (22) of the microfluidic device making contact with (and merging with) the downwardly projecting droplet (23) of the perfusion manifold assembly.

FIG. 25 shows an embodiment of drop-to-drop connecting using surface treatments alone (i.e. without geometric shapes such as pedestals or gaskets).

FIG. 32A shows one embodiment of a fluidic backplane comprising serpentine fluid resistor channels (91), vacuum channels (92) and output channels (93). FIG. 32B is an edge view. FIG. 32C shows the chip engagement bosses (94) of the fluidic backplane, which serve as its fluidic outlet ports, along with assembly alignment features (95) and a visualization cutout (96) which permits microscopy and other imaging.

FIG. 36A is a topside view of the assembly (10) before engaging the carrier (17) and chip (16). FIG. 36B shows an underside view of the assembly (10) with fluidic outlet ports (94) configured to align with ports (2) on the chip (16). FIG. 36C shows the assembly (10) engaged with the carrier such that the carrier tab (18) is positioned in the openings (112).

DEFINITIONS

Figure 1A:
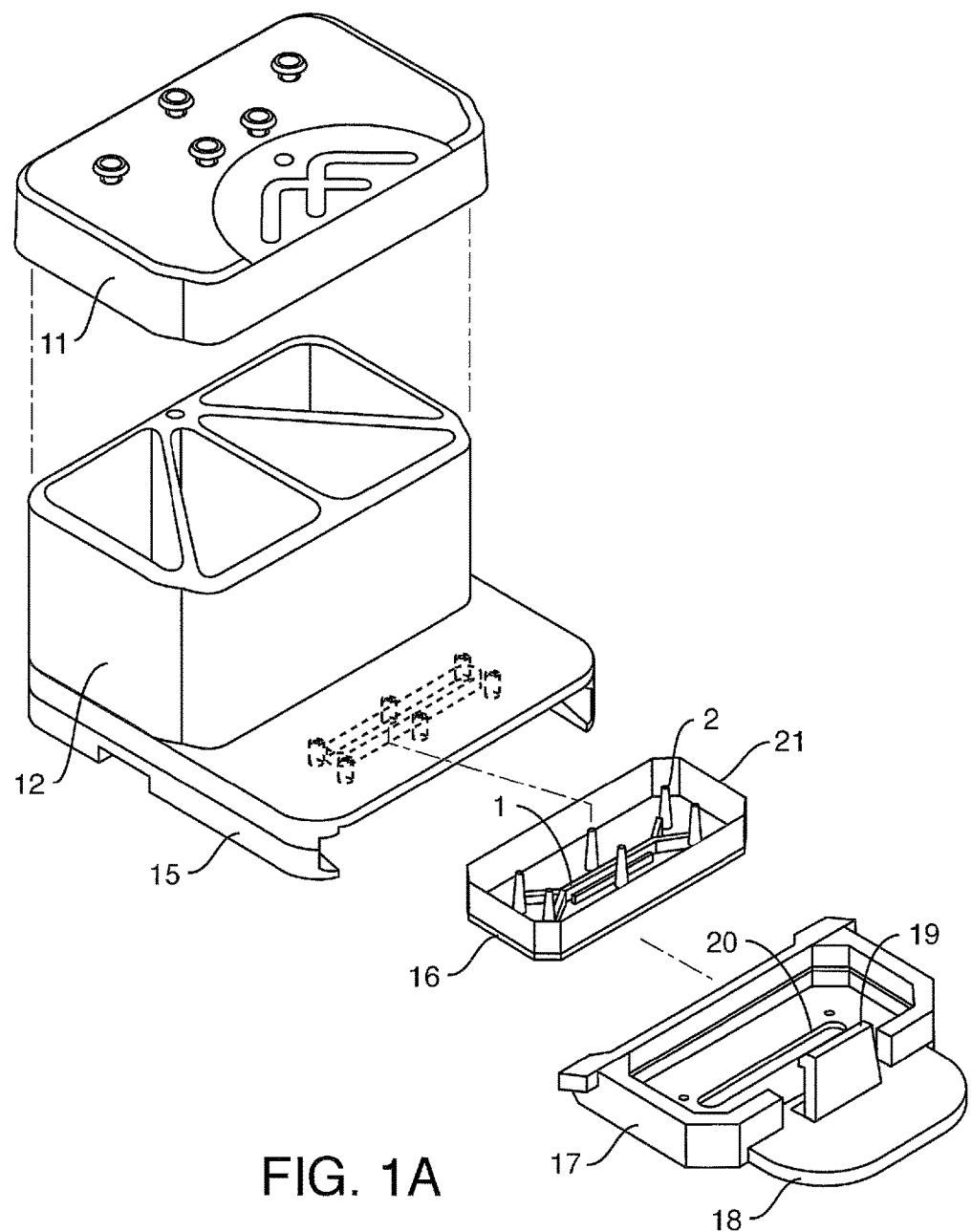
FIG. 1A is an exploded view of one embodiment of the perfusion manifold assembly showing the cover (or cover assembly) off of the reservoirs (the reservoir body can be made of acrylic, for example), the reservoirs positioned above the backplane, the backplane in fluidic communication with the reservoirs, the skirt with a side track for engaging a representative microfluidic device or "chip" (which can be fabricated out of plastic, such as PDMS, for example) having one or more inlet, outlet and (optional) vacuum ports, and one or more microchannels, the chip shown next to (but not in) one embodiment of a chip carrier (which can be fabricated out of a thermoplastic polymer, such as acrylonitrile butadiene styrene (ABS), for example), the carrier being configured to support and carrier the chip, e.g. dimensioned so that the chip fits within a cavity.

"Bond number" is a dimensionless ratio of gravity forces to capillary forces on a liquid interface. When the Bond number is high air, liquid interfaces tend to be shaped by gravity. When the Bond number is low, those surfaces tend to be shaped by the capillary force.

"Hydrophobic reagents" are used to make "hydrophobic coatings" on surfaces (or portions thereof), including projections, platforms or pedestals at or near ports, as well as mating surfaces (or portions thereof). It is not intended that the present invention be limited to particular hydrophobic reagents. In one embodiment, the present invention contemplates the use of silanes to make hydrophobic coatings, including but not limited to halogenated silanes and alkylsilanes. In this regard, it is not intended that the present invention be limited to particular silanes; the selection of the silane is only limited in a functional sense, i.e. that it render the surface hydrophobic. The present invention also contemplates using commercially available products, such as the Rain-X™ product which is a synthetic hydrophobic surface-applied product that causes water to bead, most commonly used on glass automobile surfaces.

A surface or a region on a surface is "hydrophobic" when it displays (e.g. advancing) contact angles for water greater than approximately ninety (90) degrees (in many cases, it is preferable that both advancing and receding contact angles are greater than approximately 90 degrees). In one embodiment, the hydrophobic surfaces of the present invention display advancing contact angles for water between approximately ninety (90) and approximately one hundred and ten (110) degrees. In another embodiment, hydrophobic surfaces have regions displaying advancing contact angles for water greater than approximately one hundred and ten (110) degrees. In another embodiment, hydrophobic surfaces have regions displaying receding contact angles for water greater than approximately 100 degrees. It is important to note that some liquids, and particularly some biological liquids, contain elements that may coat a surface after wetting it, thereby affecting its hydrophobicity. In the context of the present invention, it may be important that a surface resists such coating from a liquid of intended use, for example, that such coating does not create an advancing and/or receding contact angle that is less than 90 degrees over the duration that the surface remains wetted by the said liquid.

A surface or a region on a surface is "hydrophilic" when it displays (e.g. advancing) contact angles for water less than approximately ninety (90) degrees, and more commonly less than approximately seventy (70) degrees (in many cases it is preferable that both the advancing and receding contact angles are less than approximately 90 degrees or approximately 70 degrees).

Measured contact angles can fall in a range, i.e. from the so-called advancing (maximal) contact angle to the receding (minimal) contact angle. The equilibrium contact is within those values, and can be calculated from them.

Hydrophobic surfaces "resist wetting" by aqueous liquids. A material is said to resist wetting by a first liquid where the contact angle formed by the first liquid on the material is greater than 90 degrees. Surfaces can resist wetting by aqueous liquids and non-aqueous liquids, such as oils and fluorinated liquids. Some surfaces can resist wetting by both aqueous liquids and non-aqueous liquids. Hydrophobic behavior is generally observed by surfaces with critical surface tensions less than 35 dynes/cm. At first, the decrease in critical surface tension is associated with oleophilic behavior, i.e., the wetting of the surfaces by hydrocarbon oils. As the critical surface tensions decrease below 20 dynes/cm, the surfaces resist wetting by hydrocarbon oils and are considered oleophobic as well as hydrophobic.

Hydrophilic surfaces "promote wetting" by aqueous liquids. A material is said to promote wetting by a first liquid where the contact angle formed by the first liquid on the material is less than 90 degrees, and more commonly less than 70 degrees.

As used herein, the phrases "linked," "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

"Channels" are pathways (whether straight, curved, single, multiple, in a network, etc.) through a medium (e.g., silicon, plastic, etc.) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents.

"Microchannels" are channels with dimensions less than 1 millimeter and greater than 1 micron. Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

Figure 3B:
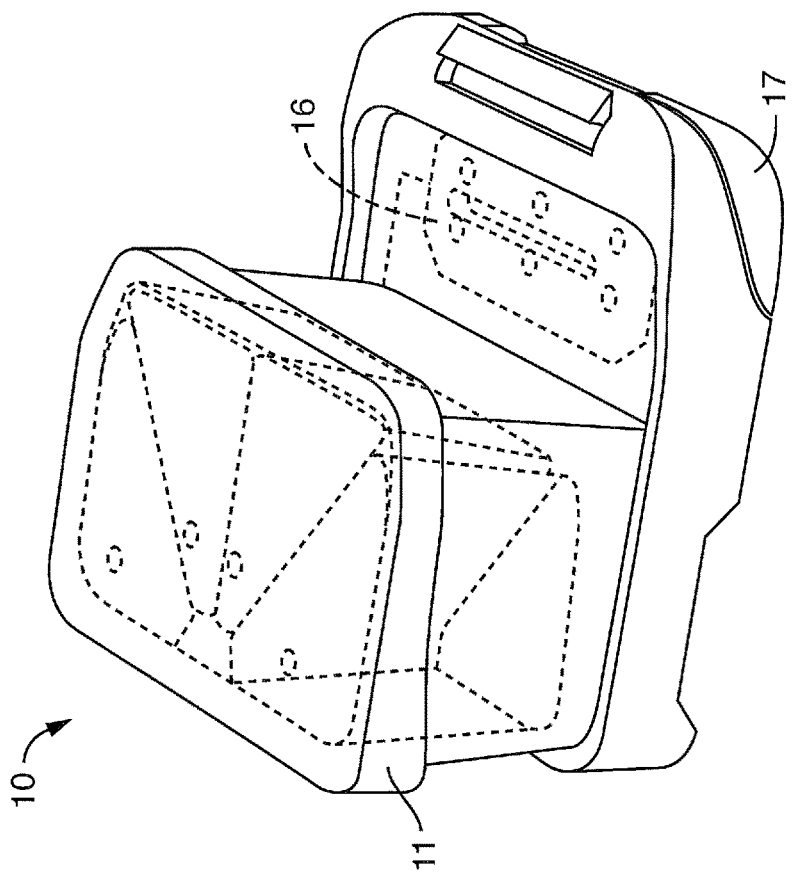
FIG. 3B is a topside schematic of an alternative embodiment of the perfusion disposable or "pod" featuring the transparent (or translucent) cover over the reservoirs, with the chip inserted. The chip can be seeded with cells and then placed in a carrier for insertion into the perfusion disposable.
Figure 3A:
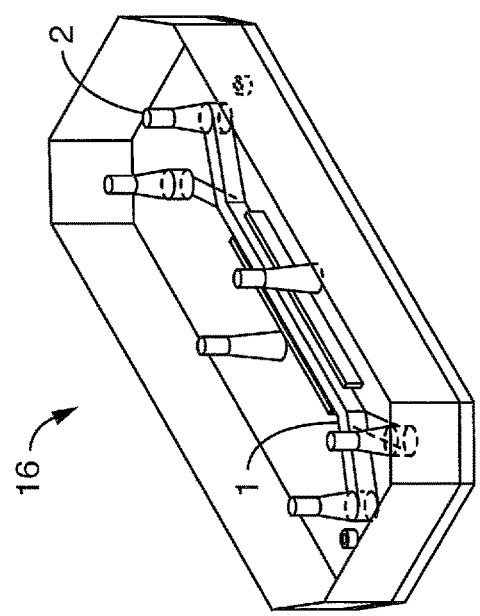
FIG. 3A shows one embodiment of the microfluidic device or chip, showing two channels, each with an inlet and outlet port, as well as (optional) vacuum ports.
Figure 3C:
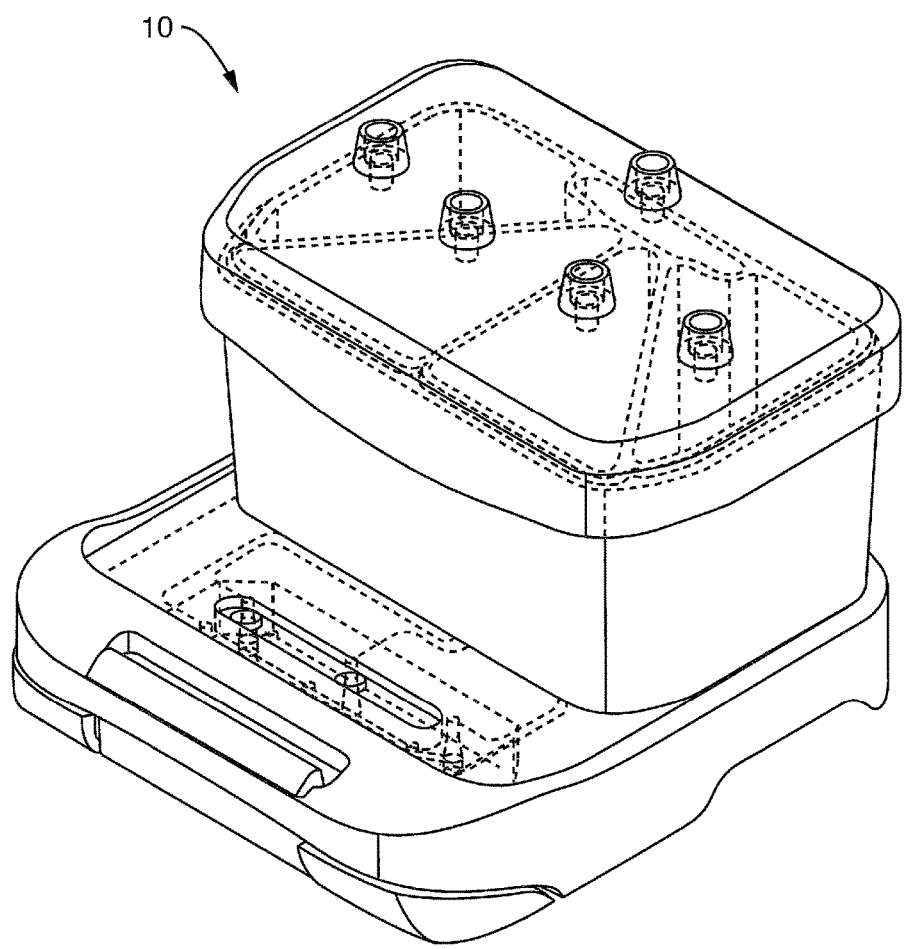
FIG. 3C is a schematic of the same assembled perfusion disposable embodiment shown in FIG. 3B, except that the ports on the cover assembly and the cutout (above the inserted chip for visualization, imaging, etc.) are now shown.
Figure 3D:
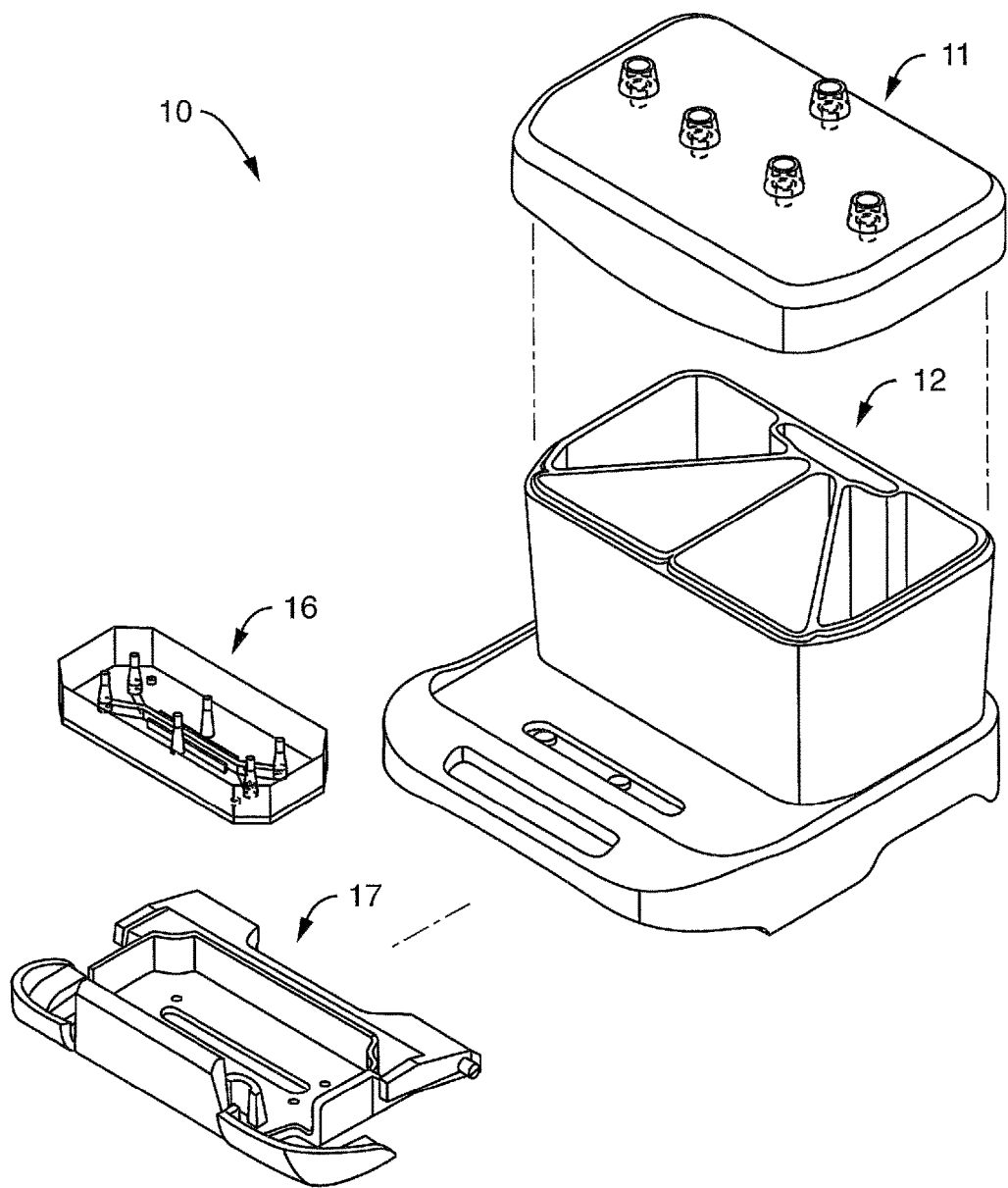
FIG. 3D is a schematic of the same perfusion disposable embodiment of FIG. 3C, but unassembled to show the relationships of the cover, reservoirs, skirt, chip and carrier.
Figure 4C:
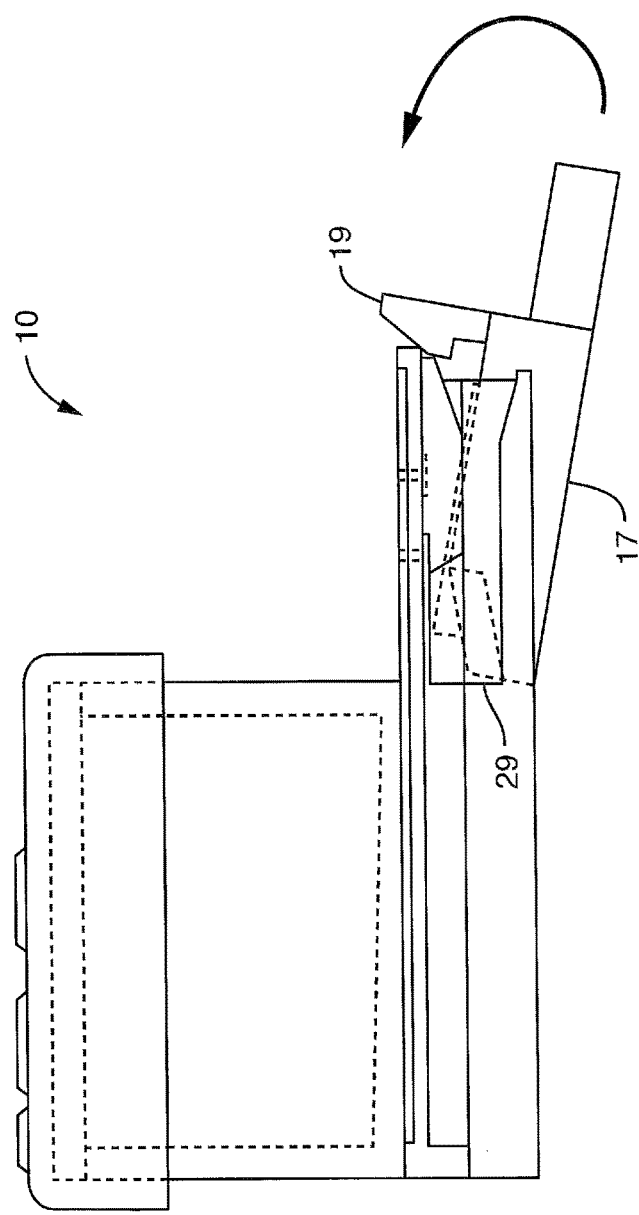
FIG. 4C shows a side view of one embodiment of a chip carrier (with the chip inside) fully engaging a side track of a skirt of one embodiment of (but not yet linked to) the perfusion manifold assembly (with an arrow showing the necessary direction of movement to get a snap fit whereby the retention mechanism will engage to prevent movement).
Figure 4D:
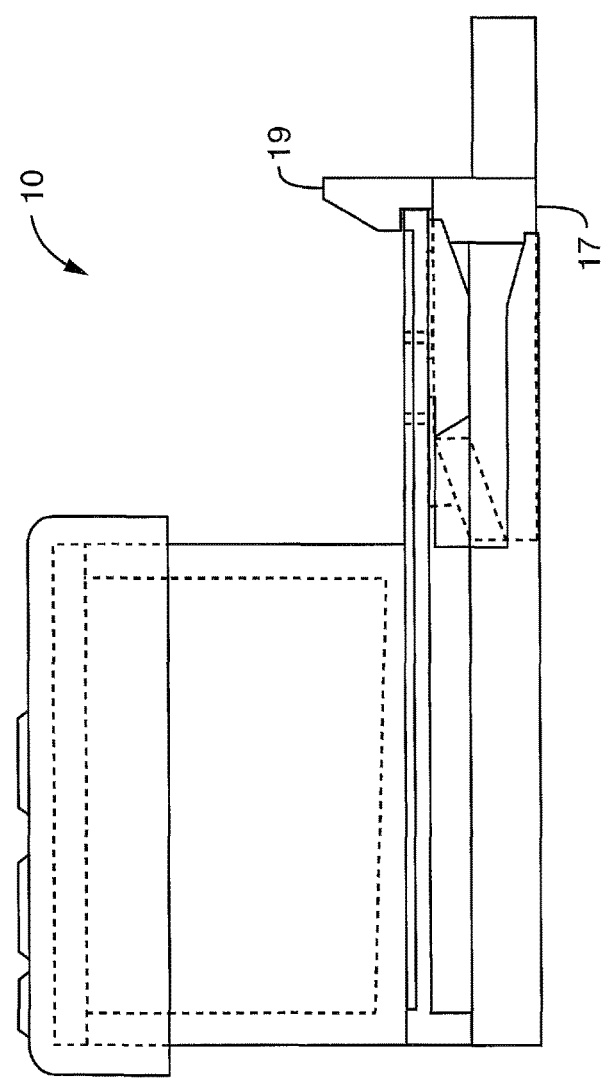
FIG. 4D shows a side view of one embodiment of a chip carrier (with the chip inside) detachably linked to the perfusion manifold assembly, where the retention mechanism is engaged to prevent movement. While detachability and optionally re-attachability is desirable in certain applications (for example, permitting chip removal to enable the addition of cells, imaging, performing various assays), in alternative embodiments, the linking is not detachable. For example, an adhesive layer, glue and/or heat staking may be employed to provide a robust linkage that may pose a challenge in detachment or reattachment.
Figures 1, 4E:
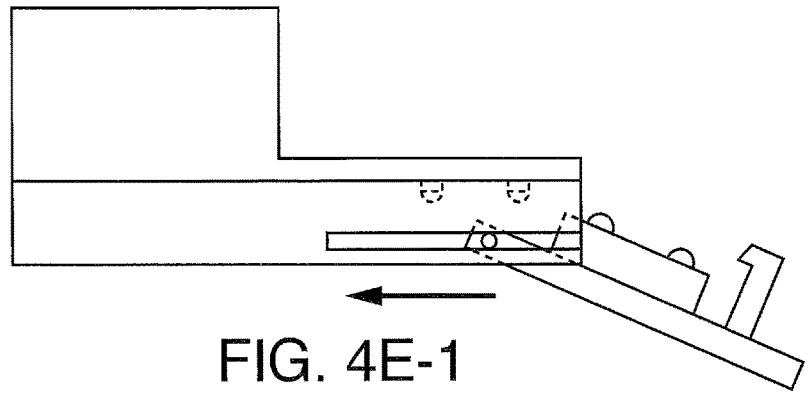
FIG. 4E is a summary slide schematically showing one embodiment of a linking approach to the perfusion manifold comprising a 1) sliding action (4E-1), 2) pivoting (4E-2), and 3) snap fit (4E-3) so as to provide alignment and fluidic connection in a single action. In the 1) sliding step, the chip (or other microfluidic device) is inserted into the carrier, which slides along to align the fluidic ports. In the 2) pivot step, the chip (or other microfluidic device) is pivoted until ports come into fluid contact. In the 3) clip or snap fit step, the force needed to provide a secure seal is provided.
Figures 2, 4E:
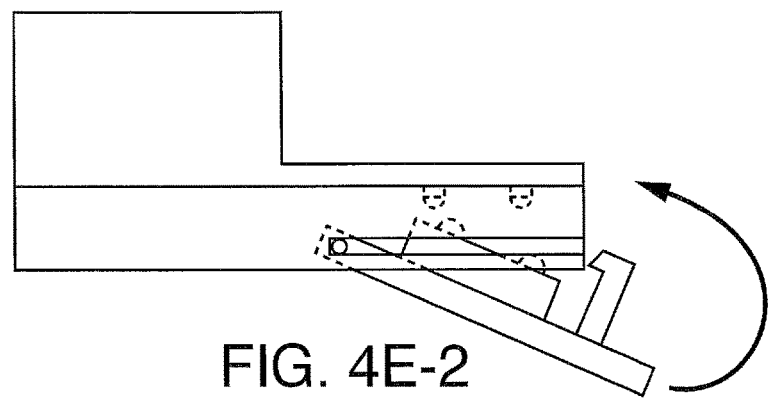
Figures 3, 4E:
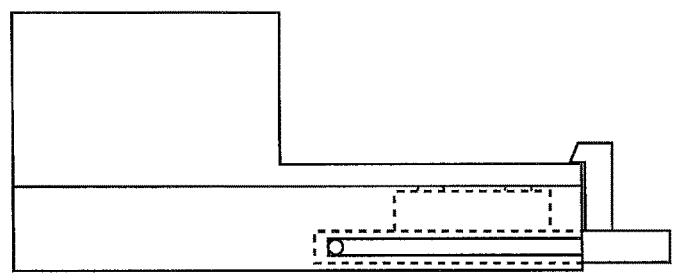

The present invention contemplates a variety of "microfluidic devices," including but not limited to microfluidic chips (such as that shown in FIG. 3A), perfusion manifold assemblies (without chips), and perfusion manifold assemblies engaged with microfluidic chips (such as that shown in FIG. 3B). However, the methods described herein for engaging microfluidic devices (e.g. by drop-to-drop connections), and for perfusing microfluidic devices are not limited to the particular embodiments of microfluidic devices described herein, and may be applied generally to microfluidic devices, e.g. devices having one or more microchannels and ports.

A "stable droplet" is a droplet of media that does not experience significant movement away from its intended location (e.g. to remain in contact with a fluidic port) and preferably does not experience a significant (>10%) change in volume or placement on a microfluidic device over the course of several seconds, and more preferably one minute, and even more preferably several minutes (2-10 minutes). In a preferred embodiment, the present invention contemplates a stable droplet during drop-to-drop engagement. A surface may intrinsically (e.g. because of what it is made of) be able to stably retain, or be made to stably retain, a droplet, meaning that the droplet will not spontaneously expand or shift beyond a limited (or designated) area. Stable droplets do not experience a significant change in volume or placement. The present invention contemplates this spatial control of droplets, i.e. retaining the droplet within a defined spatial extent and/or retaining the droplet within the spatial extent of the one or more regions. In a preferred embodiment, the present invention contemplates both preventing the droplet from extending too far, and ensuring that it is centered on the port (i.e. making sure that the area right on top of the fluidic port remains covered by the droplet). In terms of preventing the droplet from extending or spreading too wide, the present invention contemplates, in one embodiment, retaining the droplet within the spatial extent of the one or more regions. In a particularly preferred embodiment, the present invention contemplates preventing the droplet from shifting away during manipulation (i.e. rolling away on the surface as the microfluidic device or chip is moved around or even inverted. Of course, such movements are contemplated without violent shaking. A droplet that is found to be stable if a particular engagement procedure is used, may be found unstable if another procedure (e.g. more violent procedure) is utilized.

"Controlled engagement" refers to engagement of two devices that allows for both adequate alignment of vias or ports, and smooth drop-to-drop connection, which does not result in loss of droplet stability. If the devices, for example, snap violently into place or the droplets on opposite devices touch prior to engagement, droplet stability will be compromised.

GENERAL DESCRIPTION OF THE INVENTION
DETAILED DESCRIPTION

Figure 1B:
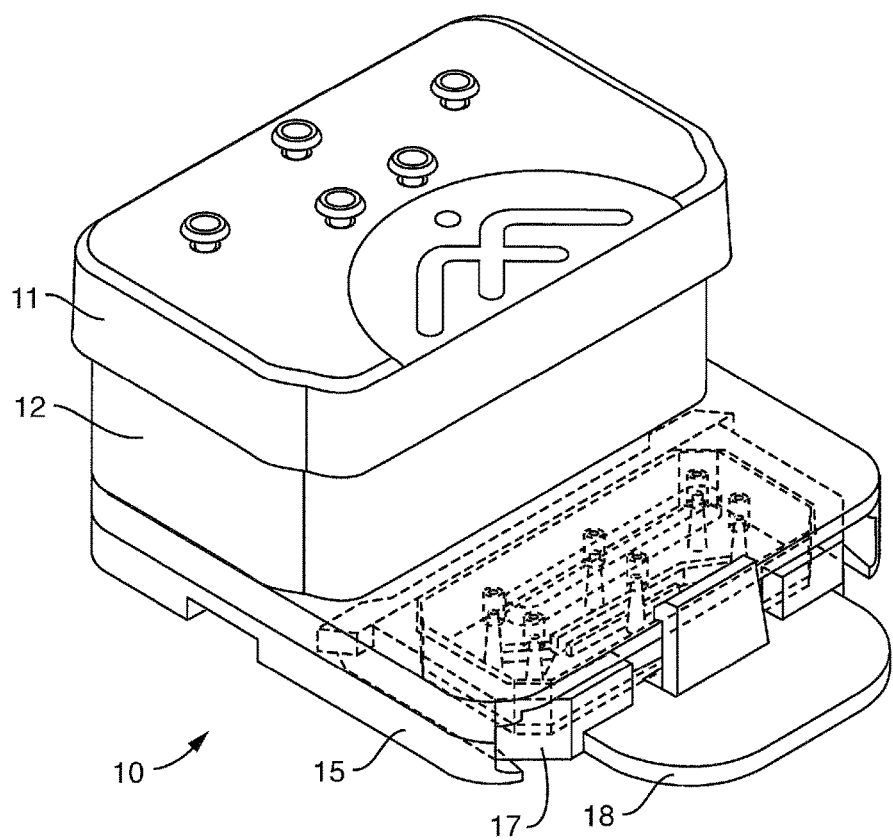
FIG. 1B shows the same embodiment of the perfusion manifold assembly with the cover on and over the reservoirs, and the chip inside the chip carrier fully linked to the skirt of the perfusion manifold assembly, and thereby in fluidic communication with the reservoirs. In one embodiment, each chip has two inputs, two outputs and (optionally) two connections for the vacuum stretch. In one embodiment, putting the chip in fluidic communication connects all six in one action, rather than connecting them one at a time.
Figure 1C:
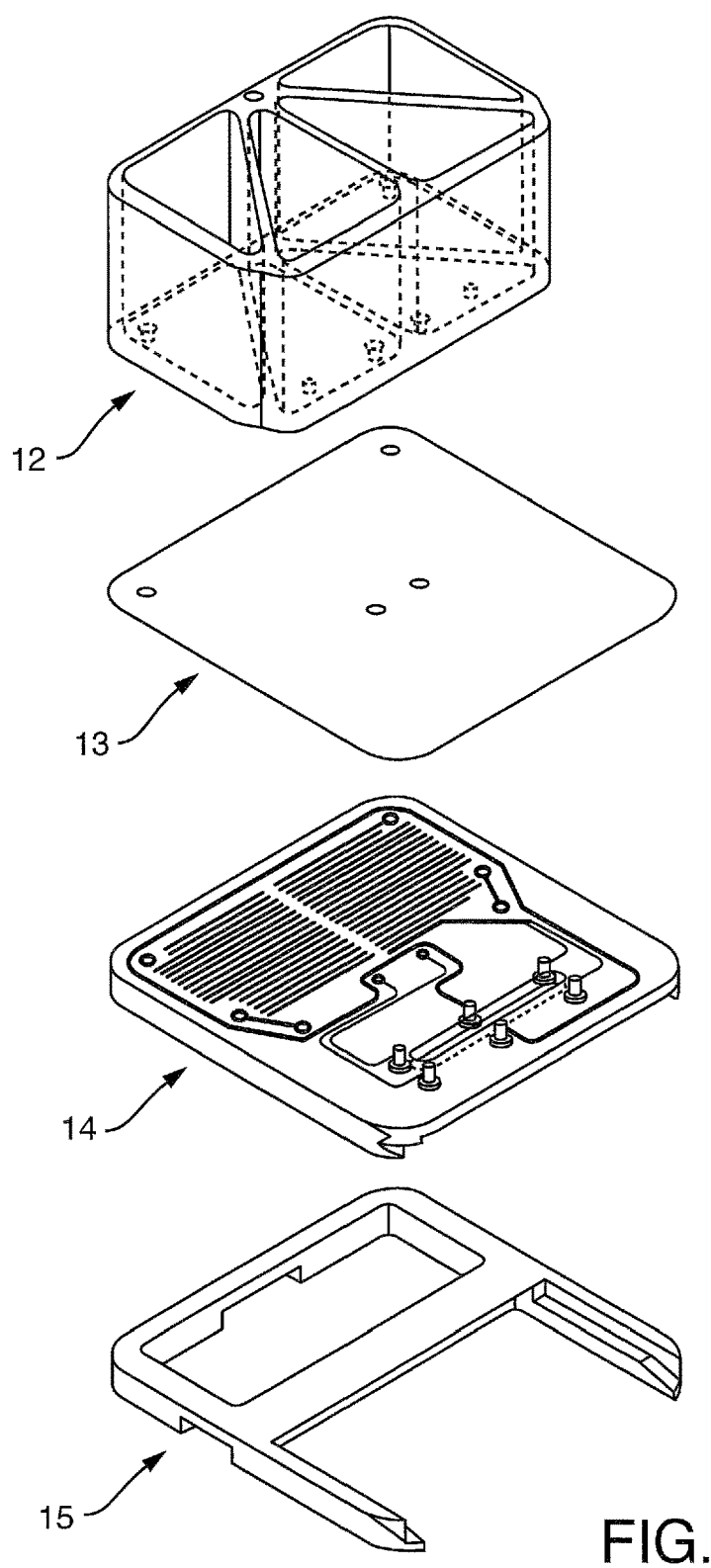
FIG. 1C is an exploded view of one embodiment of the perfusion manifold assembly (before the components have been assembled) comprising reservoirs positioned over a fluidic backplane (comprising a fluid resistor), that is fluidically sealed with a capping layer and is positioned over a skirt, with each piece dimensioned to fit over the next. In one embodiment, the skirt comprises structure (e.g. made of polymer) that borders or defines two open spaces, one of the spaces configured to receive the carrier with the chip inside. In one embodiment, the skirt has structure that completely surrounds one open space and two "arms" that extend outwardly that define a second open space for receiving the carrier. In one embodiment, the two arms have side tracks for slidably engaging the carrier edges.

In one embodiment, the present invention contemplates a perfusion manifold assembly that allows for perfusion of a microfluidic device, such as an organ on a chip microfluidic device comprising cells that mimic cells in an organ in the body or at least one function of an organ, that is (preferably detachably) linked with said assembly so that fluid enters ports of the microfluidic device from a fluid reservoir, optionally without tubing, at a controllable flow rate. In one embodiment (as shown in FIGS. 1A, 1B and 1C), the perfusion manifold assembly (10) comprises i) a cover or lid (11) configured to serve as to top of ii) one or more fluid reservoirs (12), iii) a capping layer (13) under said fluid reservoir(s), iv) a fluidic backplane (14) under, and in fluidic communication with, said fluid reservoir(s), said fluidic backplane comprising a fluidic resistor, and v) a projecting member or skirt (15) for engaging the microfluidic device (16) or chip which is preferably positioned in a carrier (17), the chip having one or more microchannels (1) and in fluidic communication with one or more ports (2). The assembly can be used with or without the lid or cover. Other embodiments (discussed below) lack a skirt or projecting member. In one embodiment, the carrier (17) has a tab or other gripping platform (18), a retention mechanism such as a clip (19), and a visualization cutout (20) for imaging the chip. The cutout (20) can enable placing a carrier (e.g. a carrier engaged with the perfusion manifold assembly or "pod" or not so engaged) onto a microscope or other inspection device, allowing the chips to be observed without having to remove the chip from the carrier. In one embodiment, the fluidic resistor comprises a series of switchbacks or serpentine fluid channels. FIG. 32 shows an enhanced schematic of one embodiment of the backplane, showing the fluid resistor channels (32A) and chip engagement bosses (32C) or ports. A variety of fluid resistors designs are contemplated, as described more fully in U.S. Provisional Application Ser. Nos. 62/024,361 and 62/127,438, which became PCT/US2015/040026, hereby incorporated by reference (and in particular, the discussion of resistors, resistor design, and pressures is incorporated herein by reference). In one embodiment, the perfusion manifold assembly is made of plastic and is disposable, i.e. it is disposed of after docking with and perfusing a microfluidic device. While the present invention contemplates "disposable" embodiments, the element may (alternatively) be reusable (e.g. as a cost consideration).

In one embodiment, the microfluidic device (e.g. chip) (16) may first be placed in a carrier (17) (e.g. chip carrier) before engaging the perfusion manifold assembly (10) or may engage the assembly directly. In either case, the (optional) detachable linking of the microfluidic device with the manifold should either a) prevent air from entering the microchannels, or b) provide a way for undesirable air to be removed or vented out of the system. Indeed, air removal may be needed in some embodiments during both chip attachment and use of the microfluidic device.

Figure 15A:
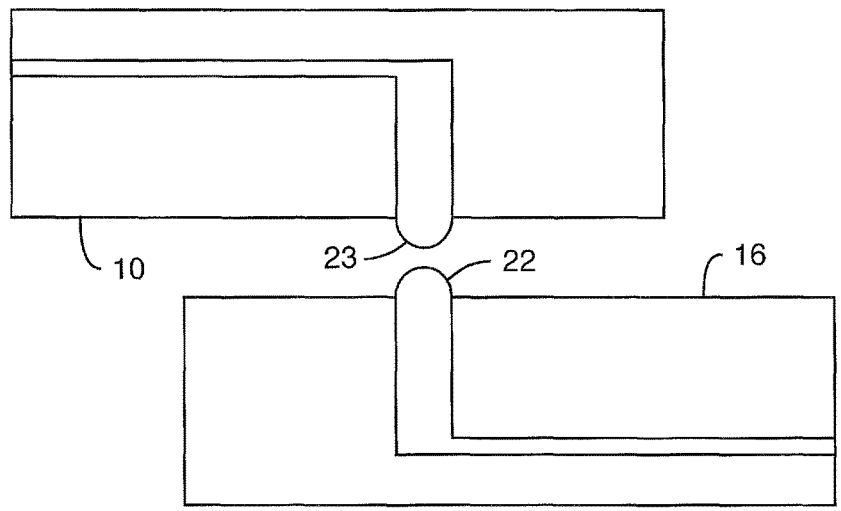
FIG. 15A shows two fluidically primed devices with microchannels with protruding droplets formed on the surfaces of the devices but not in the areas around the fluidic vias or port, and more particularly, formed directly on and above the ports.
Figure 15B:
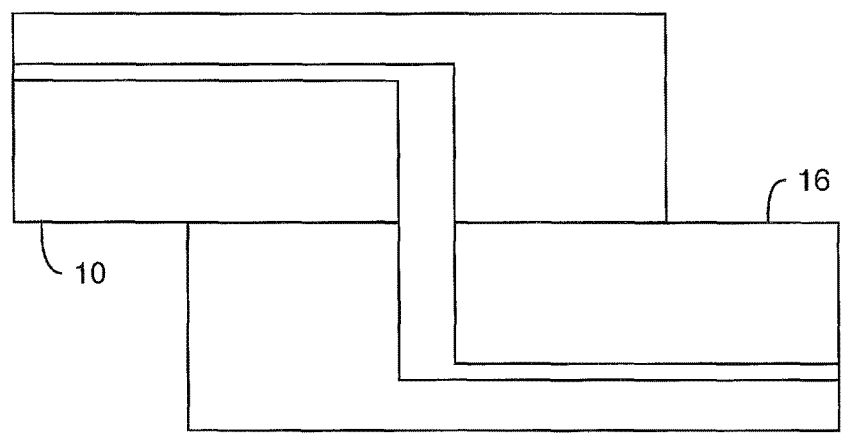
FIG. 15B shows that when the surfaces come near each other during a connection, the droplet surfaces join typically without introducing any air bubbles.

In one embodiment for preventing air from entering the microchannels, the microfluidic device is detachably linked using a "drop-to-drop" "chip-to-cartridge" connection. In this embodiment, an inlet port of the microfluidic device has a droplet (22) projecting therefrom (FIG. 15A), and the surface of the perfusion manifold assembly or "cartridge" (10) for engaging the device has a corresponding droplet (23). When the two are brought together (FIG. 15B), the droplets merge allowing for fluidic communication without the introduction of air into the channels. In one embodiment, the chip carrier is designed so as to not interfere with the "drop-to-drop" connection. For example, the carrier, in one embodiment, surrounds the sides, but not the mating surface (21) of the microfluidic device. It should be noted that FIG. 15A shows a skirt-free perfusion manifold (10) where the microfluidic device or chip engages from underneath (rather than from the side).

It is not intended that the present invention be limited to only one manner for detachably linking the microfluidic device. In one embodiment, the microfluidic device, such as an organ on a chip microfluidic device comprising cells that mimic one or more functions of cells in an organ in the body or at least one function of an organ, approaches the assembly from the side (FIG. 16A) or underneath (FIG. 16B), with the droplet (22) projecting upward, while the corresponding droplet (23) on the assembly (or other type of fluid source) projects downward. The microfluidic device (or the device carrier) may comprises a portion (24) configured to engage a side track (25) or other guide mechanism. In another embodiment, the microfluidic device, such as an organ on a chip microfluidic device comprising cells that mimic cells in an organ in the body or at least one function of an organ, approaches the assembly from above, with the droplet projecting downward, while the corresponding droplet on the assembly projects upward. In still another embodiment, the microfluidic device, such as an organ on a chip microfluidic device comprising cells that mimic cells in an organ in the body or at least one function of an organ, approaches the assembly from the side and is positioned by pivoting (FIG. 16D, see the arrow) about a hinge, socket, or other pivot point (26). In still another embodiment, the microfluidic device engages in the manner of an audio cassette or CD with the droplet projecting upward, while the corresponding droplet on the assembly projects downward, where there is a combined sideways movement and upward movement (FIGS. 16B-16C).

In one embodiment, the microfluidic device (16) is detachably linked with the perfusion manifold assembly (10)

by a clipping mechanism that temporarily "locks" the microfluidic device, including organ-on-chip devices, in place (FIGS. 4A, 4B, 4C and 4D). In one embodiment, the clipping or "snap fitting" involves a projection on the carrier (19) which serves as a retention mechanism when the microfluidic device (16) is positioned. In one embodiment, the clipping mechanism is similar to the interlocking plastic design of a Lego™ chip and comprises a straight-down clip, friction fit, radial-compression fit or combination thereof. However, in another embodiment, the clipping mechanism is triggered only after the microfluidic device, or more preferably, the carrier (17) comprising the microfluidic device (16), engages the perfusion manifold assembly (or cartridge) on a guide rail, side slot, internal or external track (25) or other mechanism that provides a stable glide path for the device as it is conveyed (e.g. by machine or by hand) into position. The guide rail, side slot, internal or external track (25) or other mechanism can be, but need not be, strictly linear and can be positioned in a projecting member or skirt (15) attached to the main body of the perfusion manifold assembly (10). In one embodiment, the beginning portion of the guide rail (25) (or side slot, internal or external track or other mechanism) comprises an angled slide (27) which provides a larger opening for easier initial positioning, followed by a linear or essentially linear portion (28). In one embodiment, the end portion (29) (close to the corresponding ports of the assembly) of an otherwise linear (or essentially linear) guide rail (25) (or side slot, internal track or other mechanism) is angled (or curves) upward (FIG. 16B) so that there is a combination of linear movement (e.g. initially) and upward movement to achieve linking.

In several embodiments, it is important that droplets remain placed at their corresponding fluidic port despite the motion of their substrate or any period of upside-down orientation. In addition, it is desirable that the droplets retain their size, for example, so that the drop-to-drop process is consistent regardless of the speed of the engagement process. Accordingly, the present invention contemplates designs and method to provide stable droplets. Stable droplets are contemplated for aqueous as well as non-aqueous liquids. Although we focus our examples without loss of generality on aqueous droplets, one familiar with the art should be able to adapt the examples and particularly the use of hydrophilic and hydrophobic regions or materials based on the wetting properties of the liquid. In some embodiments, a droplet may be restricted within a first region of a substrate by surrounding the first region with a second region, wherein the second region is hydrophobic (or more generally, with a propensity against wetting by the droplet's liquid). The said second region may be hydrophobic due to selection of one or more hydrophobic materials that it comprises (e.g. PTFE, FEP, certain grades of Nylon, etc.), surface treatment (e.g. plasma treatment, chemical treatment, ink treatment), the use of a gasket (e.g. a film, an o-ring, an adhesive gasket), by masking during treatment of at least one other region of the substrate, or a combination thereof. In some embodiments, a droplet may be restricted within a first region of a substrate by surrounding the first region with a geometric feature. In some embodiments, the geometric feature may be a ridge or a depression. Without being bound by theory, such features may act to restrict the droplet by means of their edges, which interact with the surface layer of the droplet (and correspondingly with the surface tension of the droplet), for example, by "pinning" the surface of the droplet. In some embodiments, a droplet may be restricted to cover a first region of a substrate by adapting the first region to be hydrophobic (or more generally, with a propensity for wetting by the droplet's liquid). The said first region may be hydrophilic due to selection of one or more hydrophilic materials that is comprises (e.g. PMMA, PLA), surface treatment (e.g. plasma treatment, chemical treatment, ink treatment), the use of a gasket (e.g. a film, an o-ring, an adhesive gasket), by masking during the treatment of at least one of other region of the substrate, or a combination thereof.

In one embodiment, the mating surface (21) of a microfluidic device (or at least a portion thereof adjacent the port opening) is hydrophobic or made hydrophobic (or protected with a mask during plasma treatment to keep it from becoming hydrophilic). In one embodiment, the mating surface of a perfusion manifold assembly or cartridge (or at least a portion thereof adjacent the port opening) is hydrophobic or made hydrophobic (or protected with a mask during plasma treatment to keep it from becoming hydrophilic). In one embodiment, both the mating surface of the microfluidic device (or at least a portion thereof adjacent the port opening) and the mating surface of the perfusion manifold (or at least a portion thereof adjacent the port opening) is hydrophobic or made hydrophobic (or protected with a mask during plasma treatment to keep it from becoming hydrophilic).

The advantage of the carrier is that the surfaces of the microfluidic device need not be touched during the detachable linkage with the perfusion manifold assembly. The carrier can have a plate, platform, handle or other mechanism for gripping the carrier (18), without contacting the mating surface (21) of the microfluidic device (16). The retention mechanism (19) can comprise a projection, hook, latch or lip that engages one or more portions of the perfusion manifold assembly, and more preferably the skirt of the perfusion manifold assembly, to provide a "snap fit."

Figure 27:
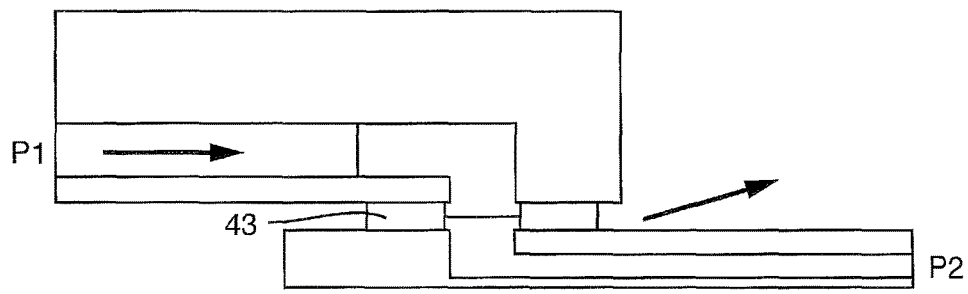
FIG. 27 shows an embodiment where the microfluidic device ("chip") is linked from below to the perfusion manifold assembly (above) at a port with a venting gasket (43), where the assembly does not cover or close off the gasket, allowing any air trapped during the linking to be vented out (right hand arrow). It may be desirable to ensure that any air preferentially flows out through the venting gasket rather than continue to flow through the channels. In some embodiments, this preferential flow is encouraged by subjecting fluid in the fluid channel of the assembly (left hand arrow) to a first pressure (P1) and fluid in the microfluidic device channel to a second pressure (P2), where P1 and P2 are greater than the back-pressure of the venting gasket. In some embodiments, the pressure P1 and/or P2 are applied using a pressure source and/or gravitational head. In some embodiments, the pressure P1 and/or P2 are generated by the flow resistance of the fluid.
Figure 28:
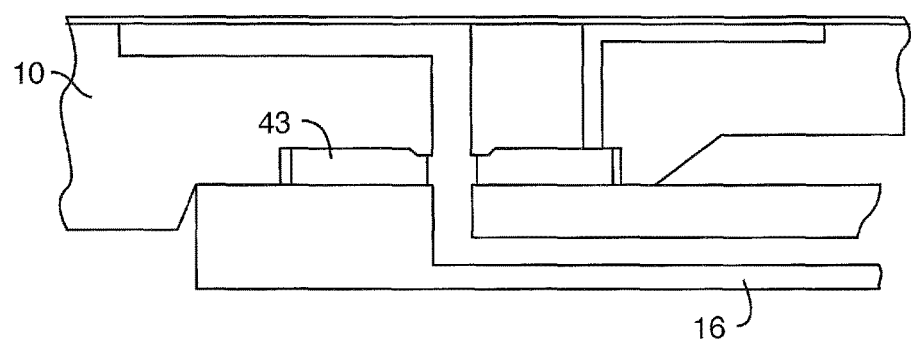
FIG. 28 shows another embodiment where the microfluidic device (16) ("chip") is linked from below to the perfusion manifold assembly (10) (above) at a port with a venting gasket (43), where the assembly covers the gasket (i.e. the gasket is enclosed by the assembly mating surface), but where there is a path in the assembly above the gasket to allow any air trapped during the linking to be vented out.
Figure 29:
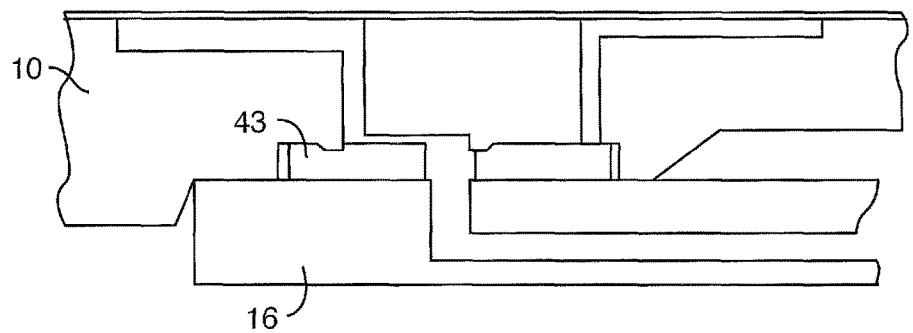
FIG. 29 shows another embodiment where the microfluidic device (16) ("chip") is linked from below to the perfusion manifold assembly (10) (above) at a port with a venting gasket (43), where the fluid path goes over the gasket (the gasket can be larger if desired). This embodiment facilitates the removal of air trapped during the linking including smaller bubbles, since, without being bound by theory, it enables smaller bubbles to interact with ("wet") the venting gasket.
Figure 30A:
FIGS. 30 and 31 are a series of still photos from a video showing one embodiment of the microfluidic device (having droplets protruding from gaskets) moving along a essentially linear (i.e. along the x axis in the x/y plane) rail or guide track of a fluid source, or microfluidic device such as the perfusion manifold assembly (compare FIG. 30A to 30B) until it gets close (FIG. 31A) to the corresponding ports of the perfusion manifold assembly, whereupon a combination of movement in the x axis and z axis (i.e. side movement and upward movement) causes the droplets to merge and the chip to link (FIG. 31B).
Figure 30B:
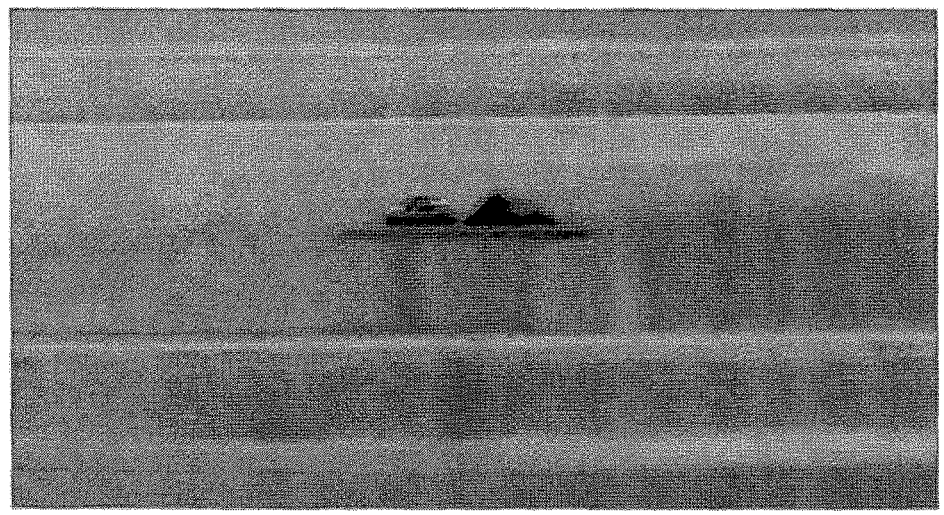
Figure 31A:
Figure 31B:
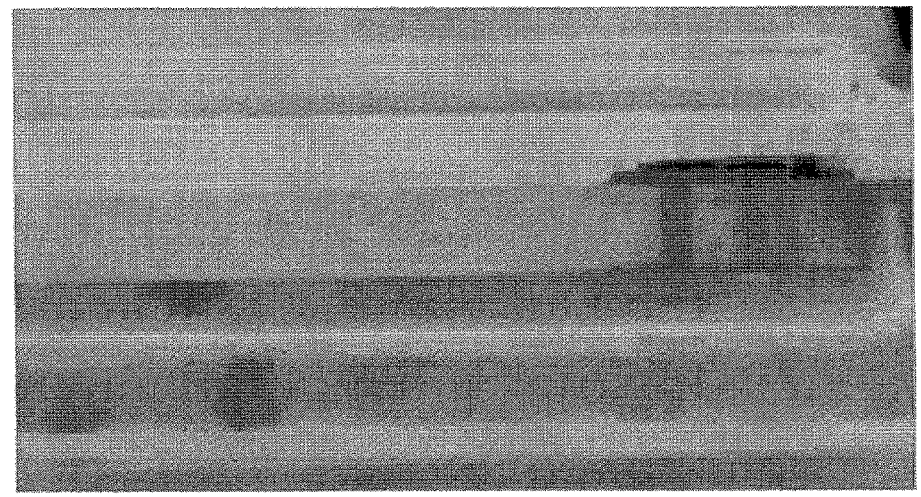

In other embodiments (FIGS. 27, 28 and 29), one or more gaskets can be used to vent air (e.g. any air that has been introduced because of the detachable linking of the microfluidic device with the perfusion manifold assembly). While in one embodiment, bubbles can be trapped (and their impact thereby limited), in an alternative embodiment, they are vented. One method involves use of hydrophobic vent material (molded or sheet). For example, the hydrophobic vent material may comprise PTFE, PVDF, hydrophobic grades of Nylon, or a combination thereof. In some embodiments venting can be accomplished by employing materials that display high gas permeability (e.g. PDMS). In other embodiments, venting can be accomplished by employing porous materials, for example, sintered materials, porous membranes (e.g. track-etched membranes, fiber-based membranes), open-cell foams, or a combination thereof. In a preferred approach, air escapes from a vented (or venting) gasket. In some embodiments, the perfusion manifold assembly or microfluidic device comprise a vent adapted to provide a path for undesired gas to escape.

Figure 5:
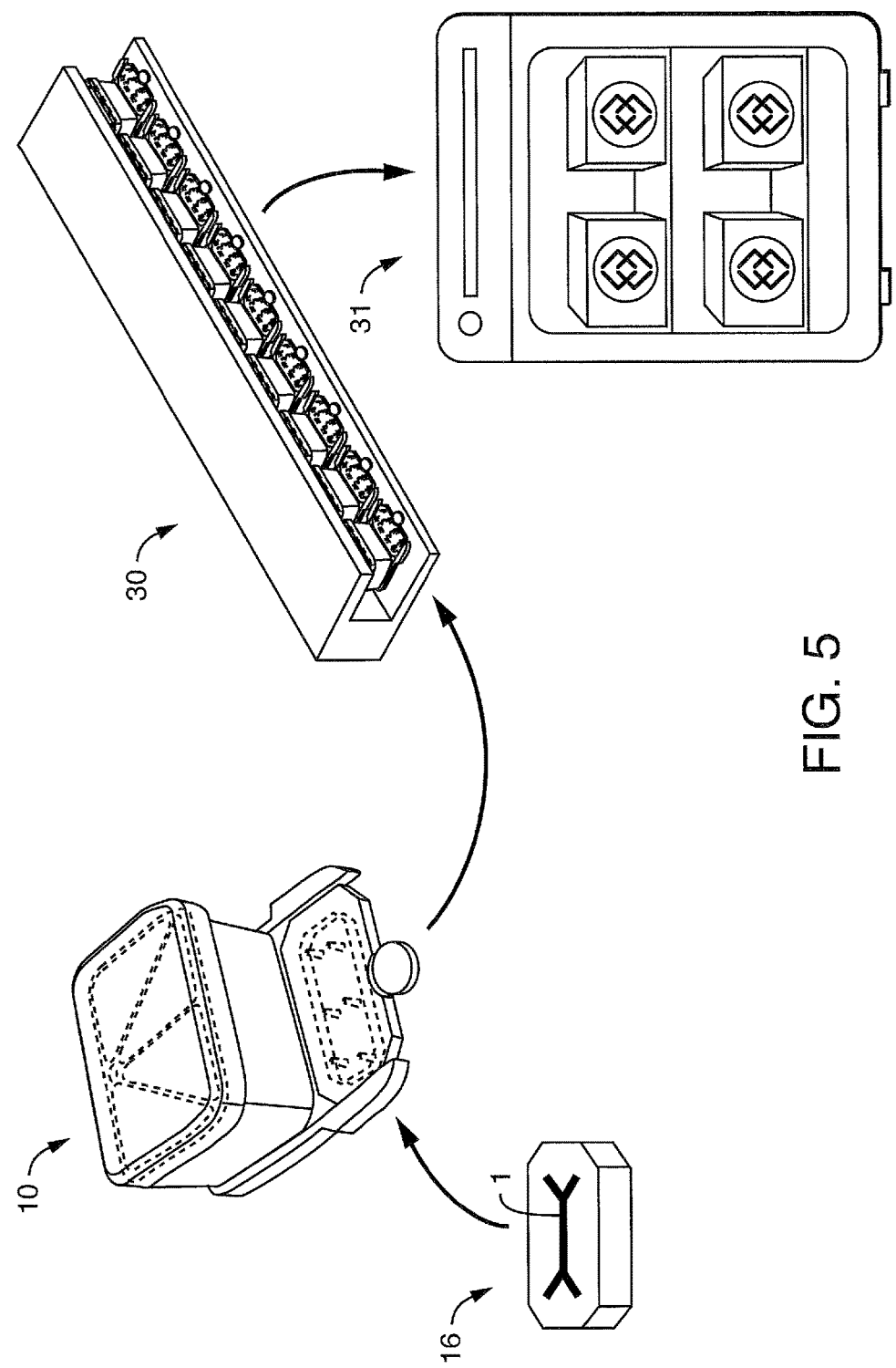
FIG. 5 is a schematic of one embodiment of a work flow (with arrows showing each progressive step), where the chip is linked (e.g. snapped in) to a disposable perfusion manifold assembly ("perfusion disposable"), which in turn is positioned with other assemblies on a culture module, which is placed in an incubator. In alternative embodiments, the culture module may comprise features of an incubator (e.g. a heat source and/or a source of warm moist air), so as to avoid the need for a separate incubator. While the present invention contemplates "disposable" embodiments, the element may (alternatively) be reusable (e.g. as a cost consideration). In a further embodiment of the work flow or method, the chip can be placed in a carrier, the carrier can be placed in a seeding guide (discussed and illustrated below), cells can be seeded into the chip, the carrier can be removed from the seeding guide, and the carrier can engage the perfusion disposable (with the rest of the work flow as illustrated in FIG. 5).

Once a microfluidic device (or "chip") has docked with the perfusion manifold assembly, the assembly-chip combination can be placed into an incubator (31) (typically set at a temperature above room temperature, e.g. 37° C.), or more preferably, into a culture module (30) capable of holding a plurality of assembly-chip combinations, the culture module configured to fit on an incubator shelf (see FIG. 5). This allows for the easy handling of many (e.g. 5, 10, 20, 30, 40, 50 or more) microfluidic devices at one time. For example, where the culture module comprises 9 assembly-chip combinations, and an incubator is sized for 6 to 9 culture modules, between 54 and 81 "organs-on-chip" can be handled in a single incubator (FIG. 5 and FIG. 8). In another example, where the culture module comprises 12 assembly-chip combinations, and an incubator is sized for 4 to 6 culture modules, between 48 and 72 "organs-on-chip" can be handled in a single incubator. The perfusion manifold can be easily removed and inserted into the culture module without breaking the fluidic connections to the chip. In one embodiment, the culture module is capable of maintaining the temperature above room temperature, e.g. 37° C., without being placed in an incubator.

The culture module (30), in one embodiment (FIG. 6), comprises a removable tray (32) for positioning the assembly-chip combinations, a pressure surface (33), and pressure controllers (34), along with an optional user interface (46) to control the movement of the various elements. In one embodiment, the tray (32) can slide. In one embodiment, the tray is positioned on the culture module and the tray is moved up via a tray mechanism (35) to engage the pressure surface (33) of the culture module, i.e. the cover or lid (11) of the perfusion manifold assembly (10) engages the pressure surface of the culture module (30). Multiple perfusion assemblies (10) can be attached to the pressure controllers in a single action by the tray mechanism. In another embodiment, the tray is positioned on the culture module and the pressure surface of the culture module (30) is moved down to engage the tray (32), i.e. the cover or lid (11) of the perfusion manifold assembly (10). In either case, in one embodiment (FIGS. 2A and 2B), the cover or lid comprises ports such as through-hole ports (36) that are engaged by corresponding pressure points on the pressure surface (33) of the culture module. These ports (36), when engaged, transmit applied pressure inward through the cover and through a gasket (37) and apply the pressure to the fluid in the reservoirs (12) of the perfusion manifold assembly (10). Thus, in this embodiment, pressure is applied through the lid (11) and the lid seals against the reservoir(s). For example, when on applies 1 kPa, this nominal pressure results, in one embodiment, in a flow rate of approximately 30-40 uL/hr. Alternatively, these ports (36), when engaged, move inward on the cover so as to contact the gaskets (i.e. the ports act essentially like plungers).

Figure 8A:
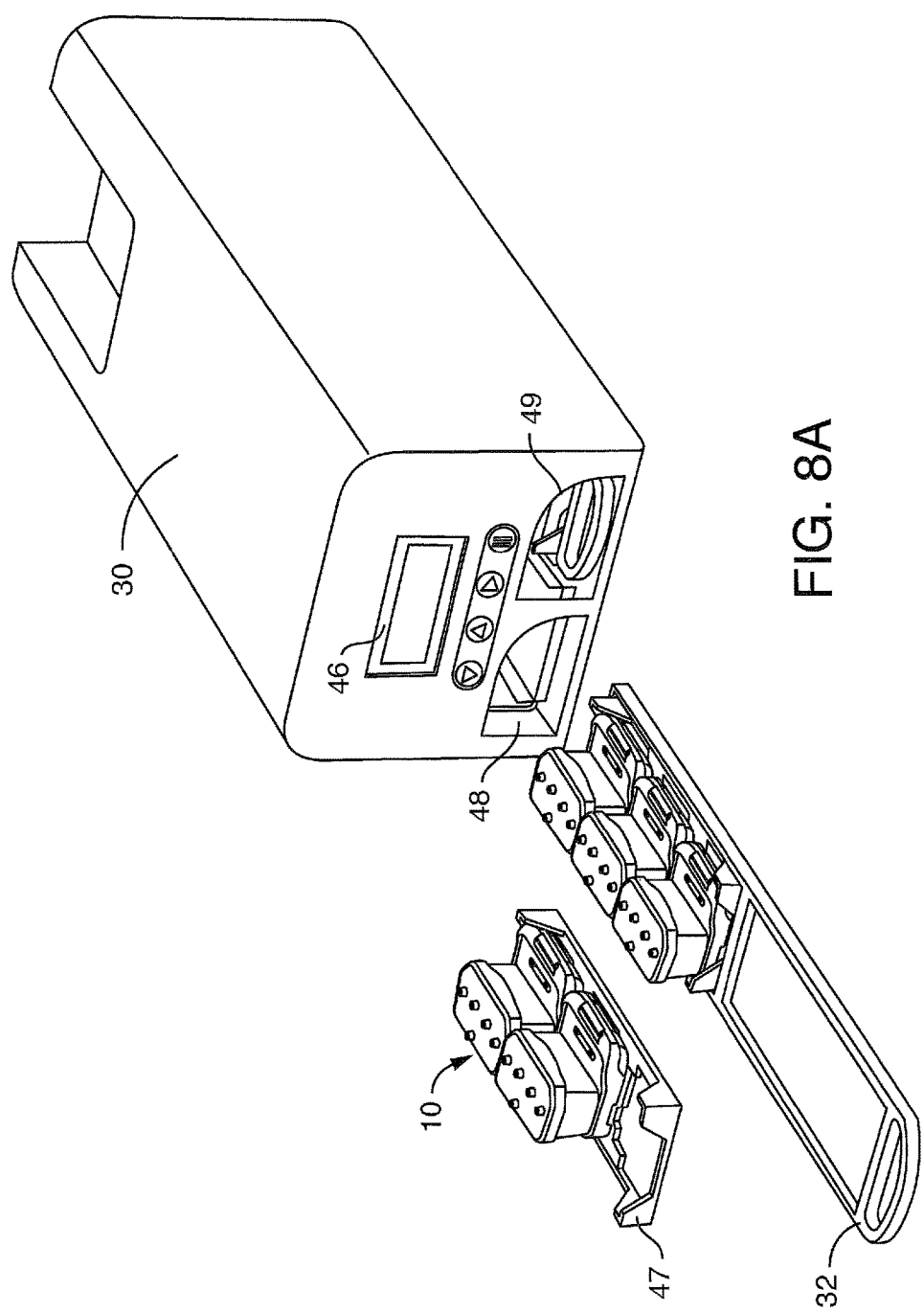
FIG. 8A is a schematic of another embodiment showing the tray (or rack) and sub-tray (or nest) for transporting and inserting the perfusion disposables (PDs) into the pressure module, which has a user interface on outside of the housing.

FIG. 8A is a schematic of another embodiment of the culture module (30) showing the tray (or rack) (32) and sub-tray (or nest) for transporting and inserting the perfusion disposables (10) into the culture module, which has two openings (48, 49) in the housing to receive the trays, and a user interface (46) to control the process of engaging the perfusion disposables and applying pressure. A typical incubator (not shown) can hold up to six modules (30). FIG. 8B is a schematic of the same embodiment of FIG. 8A, but showing both of the trays (or racks) (32) inserted into the two openings (48, 49) in the housing (53) of the pressure module (30), which has a user interface (46) (e.g. LCD screen) to control the process.

Figure 9A:
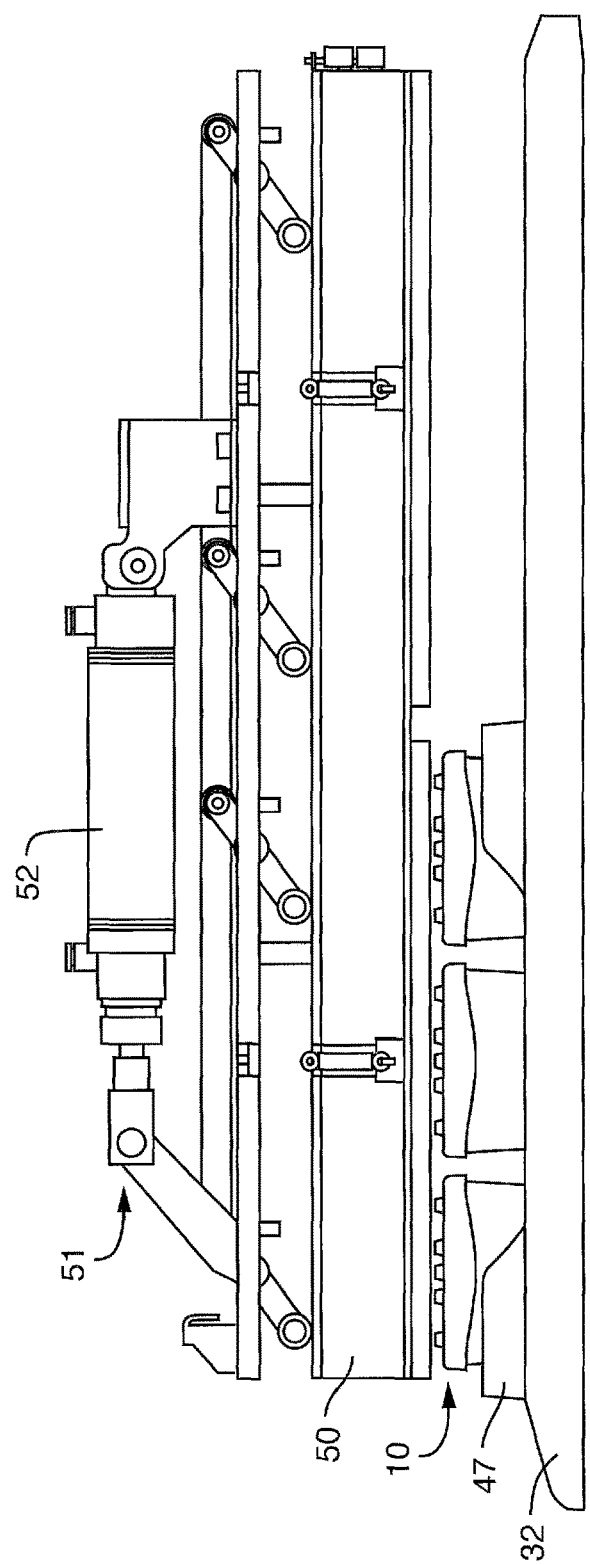
FIG. 9A is a schematic of the interior of one embodiment of the pressure module (in an open position), showing the positioning of the tray (or rack), sub-tray (or nest), perfusion disposables (PDs) under a pressure manifold (but not engaging it, so the clearance is sufficient to remove them), with the actuation assembly (including the pneumatic cylinder) above. Three microfluidic devices or perfusion disposables are shown to illustrate, although more (e.g. 6, 9 or 12) are typically used at once.

FIG. 9A is a schematic of the interior of one embodiment of the module (i.e. the housing has been removed), showing the pressure manifold (50) in an open position, with the positioning of the tray or rack (32), sub-tray or nest (47), perfusion disposables (10) under the pressure manifold (50) but not engaging it (so the clearance is sufficient to remove them), with the actuation assembly (51) including the pneumatic cylinder (52) above.

Figure 9B:
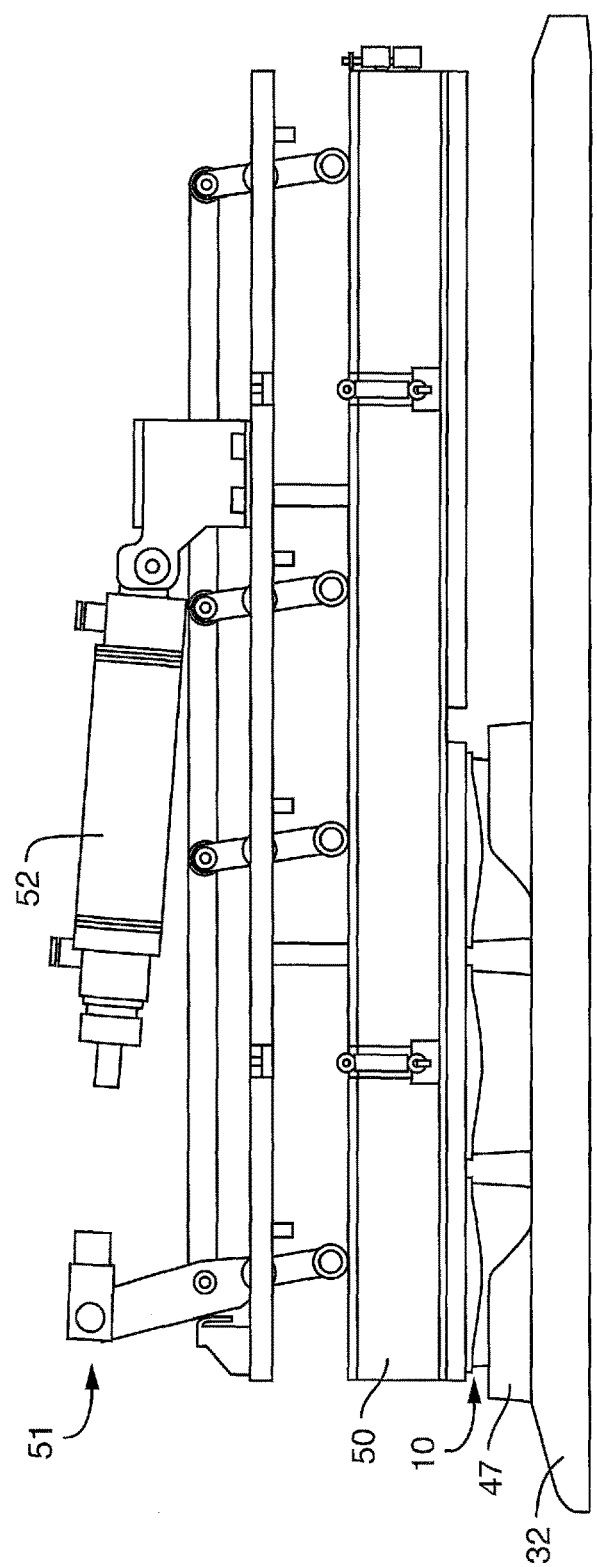
FIG. 9B is a schematic of the interior of one embodiment of the pressure module (in a closed position), showing the positioning of the tray (or rack), sub-tray (or nest), perfusion disposables (PDs) under the pressure manifold (and engaging it), with the actuation assembly (including the pneumatic cylinder) above. Again, three microfluidic devices or perfusion disposables are shown to illustrate, although more (e.g. 6, 9 or 12) are typically used at once.

FIG. 9B is a schematic of the interior of one embodiment of the module (i.e. the housing has been removed), showing the pressure manifold (50) in a closed position, with the positioning of the tray or rack (32), sub-tray or nest (47), perfusion disposables (10) under the pressure manifold (50) and engaging it, with the actuation assembly (51) including the pneumatic cylinder (52) above. The pressure manifold (50) simultaneously engages all of the perfusion disposables (10) while media perfusion is required or needed. Independent control of the flow rate in the top and bottom channels of the chip (16) can be achieved. The pressure manifold (50) can disengage (without complicated fluid disconnects) as desired to allow removal of the trays (32) or nests (47) for imaging or other tasks. In one embodiment, the pressure manifold (50) can simultaneously disengage from a plurality of perfusion manifold assemblies. In one embodiment, the perfusion disposables (10) are not rigidly fixed inside the nests (47), allowing them to locate relative to the pressure manifold (50) as it closes. In a preferred embodiment, integrated alignment features in the pressure manifold (50) provide guidance for each perfusion disposable (10).

In one embodiment, the cover or lid is made of polycarbonate. In one embodiment, each through-hole port is associated with a filter (38) (e.g. a 0.2 um filter). In one embodiment, the filters are aligned with holes (39) in a gasket positioned underneath the cover.

Figure 10A:
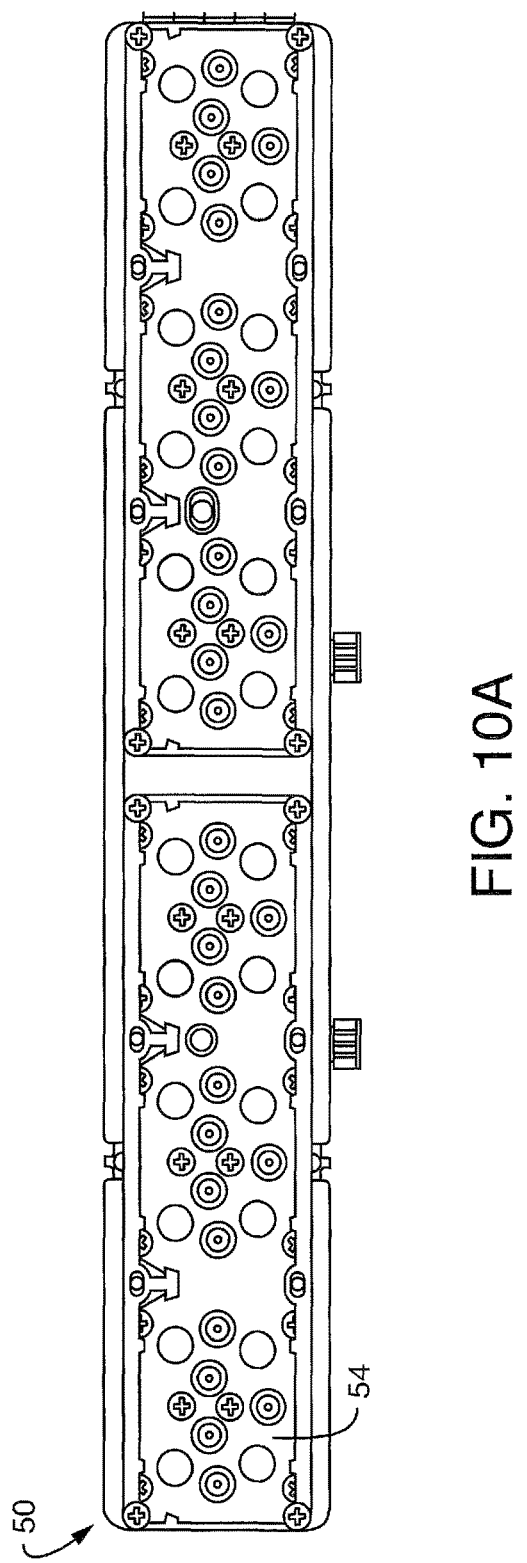
FIG. 10A is a schematic of one embodiment of the pressure manifold (50) showing the view of the PD engaging face (54) with several PD engaging locations (in this case, six engaging locations).
Figure 10B:
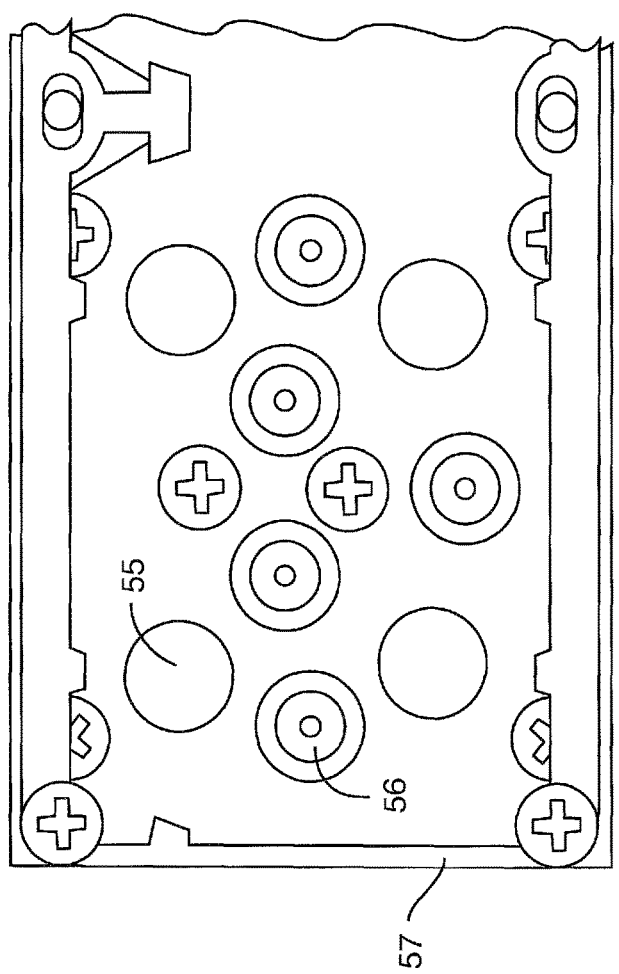
FIG. 10B shows a magnified portion of the engaging face (54) of the pressure manifold (50) highlighting the spring shuttle (55), valve seals (56) and alignment features (57) (so that the PD is aligned with the manifold).
Figure 10C:
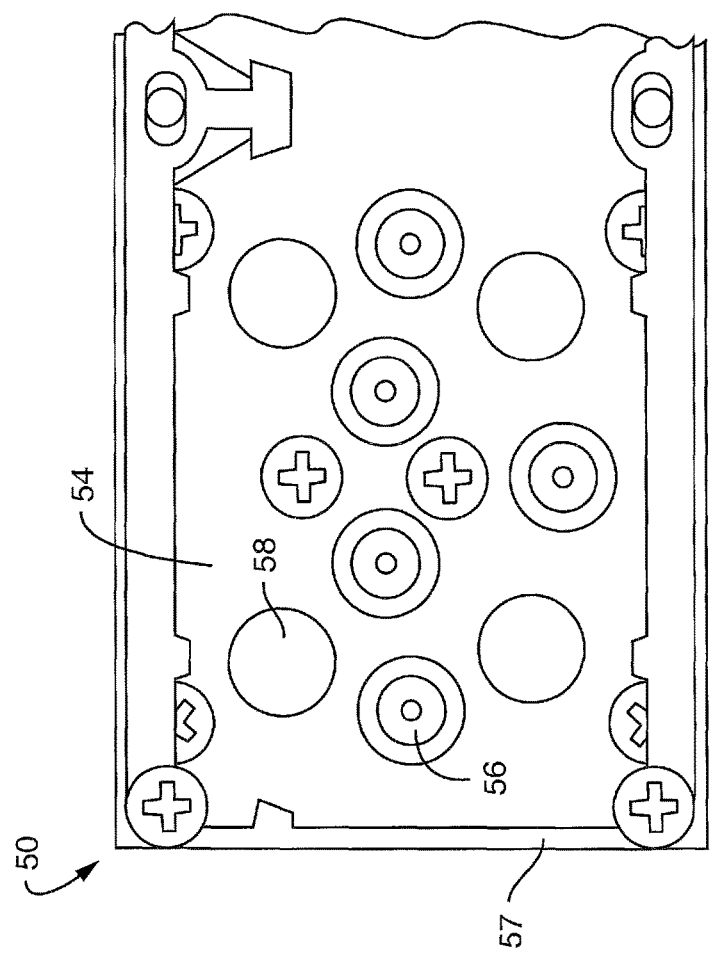
FIG. 10C is a schematic of another embodiment of the pressure manifold (50) showing the PD engaging face (54), along with an magnified portion highlighting the lid compressor (58), valve seals (56) and alignment features (57) (so that the PD is aligned with the manifold).
Figure 10D:
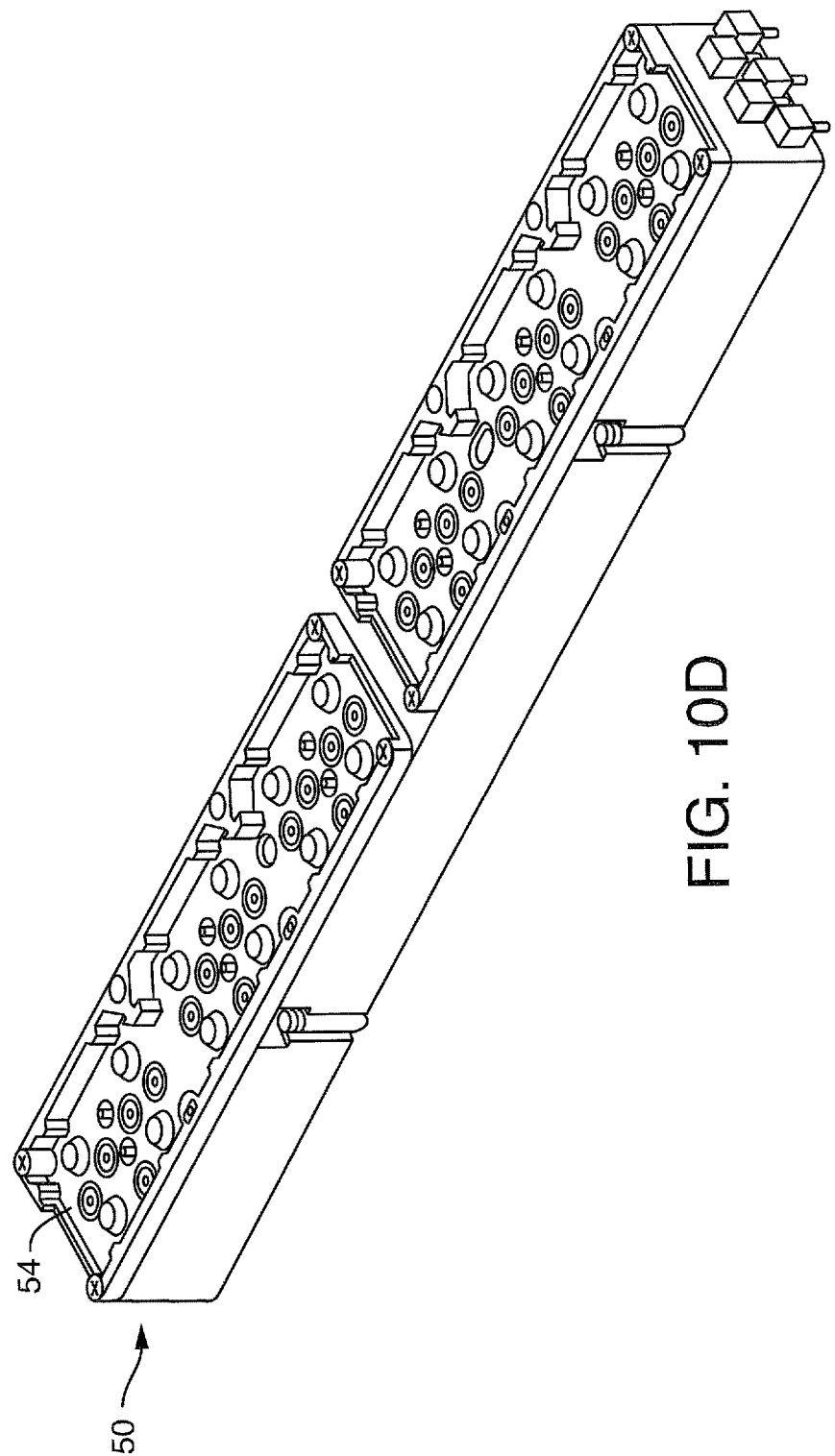
FIG. 10D is a schematic of one embodiment of the pressure manifold (50) showing the PD engaging face (54) from the side.
Figure 10E:
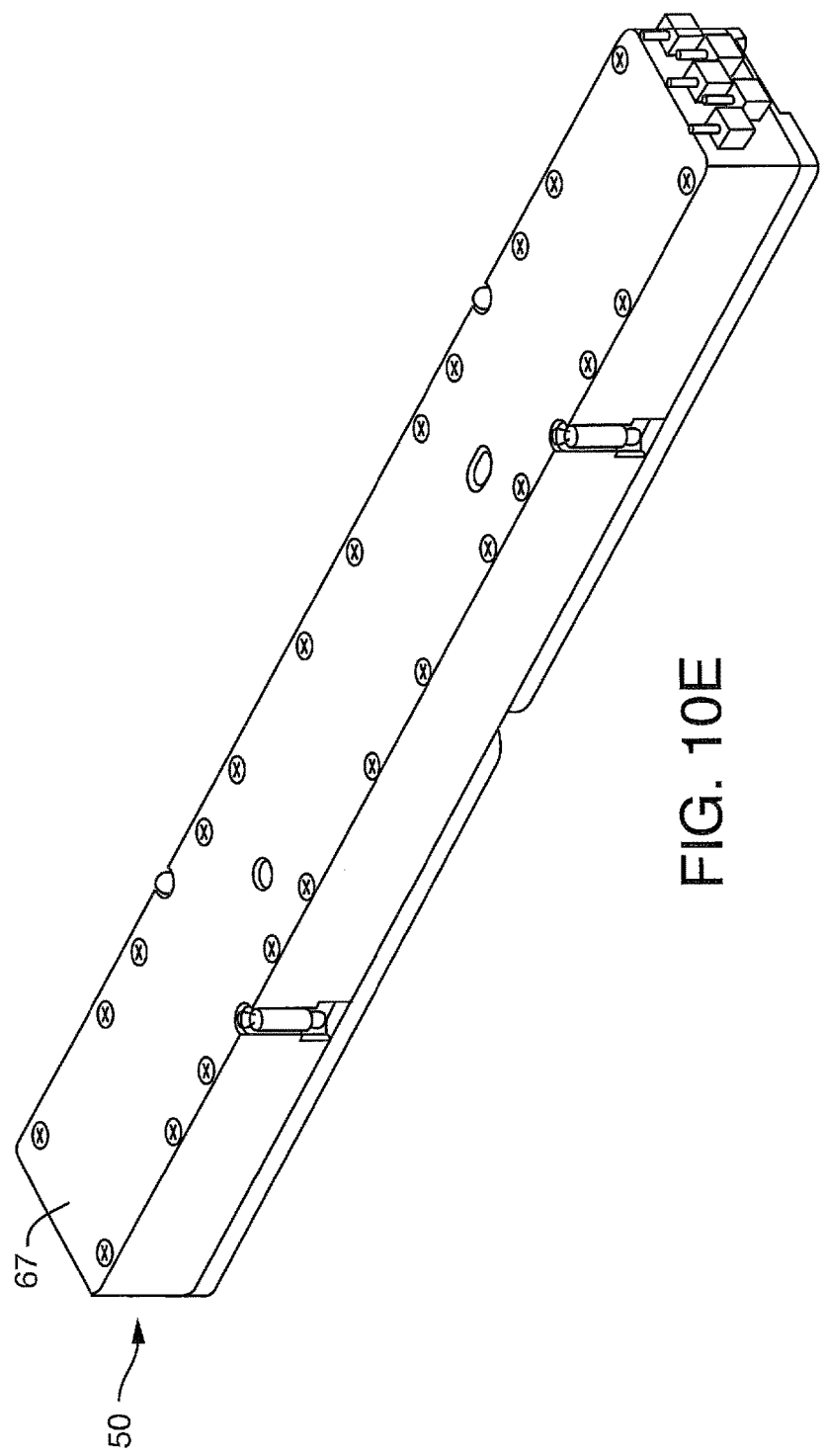
FIG. 10E is a schematic of one embodiment of the pressure manifold (50) showing the opposite face (67).
Figure 10F:
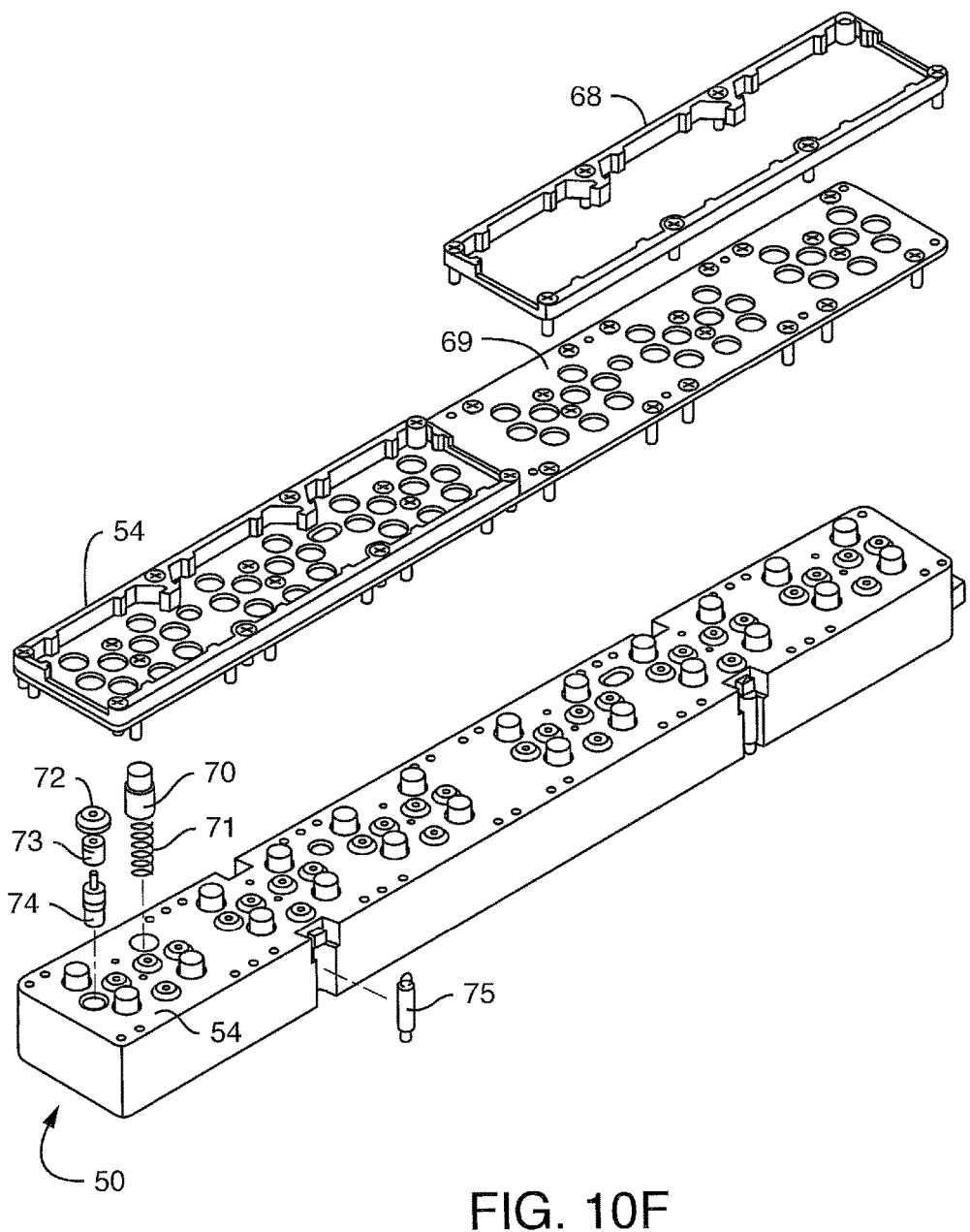
FIG. 10F is a schematic of one embodiment of the pressure manifold (50) showing the PD engaging face (54) view with the PD guide (68) and lower backer plate (69) removed, highlighting one spring carrier (70) and spring (71) (out of many) by showing it removed from the manifold body, along with one seal (72), shuttle (73), and valve body (74) (out of many) by showing it removed from the manifold body. An exterior spring (75) adapted to depress the pressure manifold against the perfusion disposables is also highlighted by showing it removed.
Figure 10G:
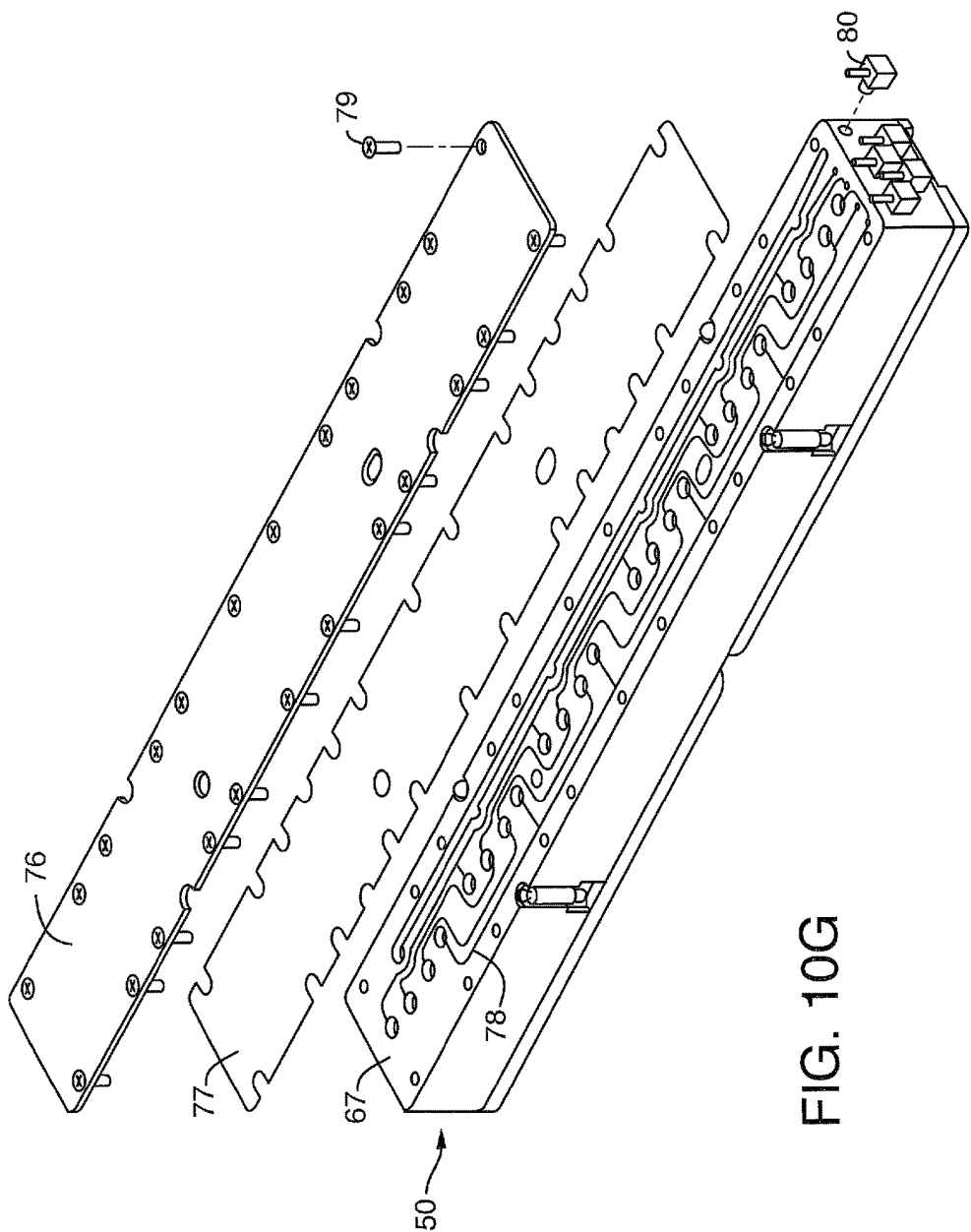
FIG. 10G is a schematic of one embodiment of the pressure manifold (50) showing the opposite face (67) (not the PD engaging face) view with the upper backer plate (76) and capping strip (77) removed. Illustrated are manifold routing channels (78), which are adapted to direct and optionally distribute pressure and/or fluid from one or more pressure ports. Additionally illustrated is one screw (79) (among many) and one gas port (80) (out of five, including both gas and vacuum ports) by showing it removed from the manifold body (50).
Figure 10H:
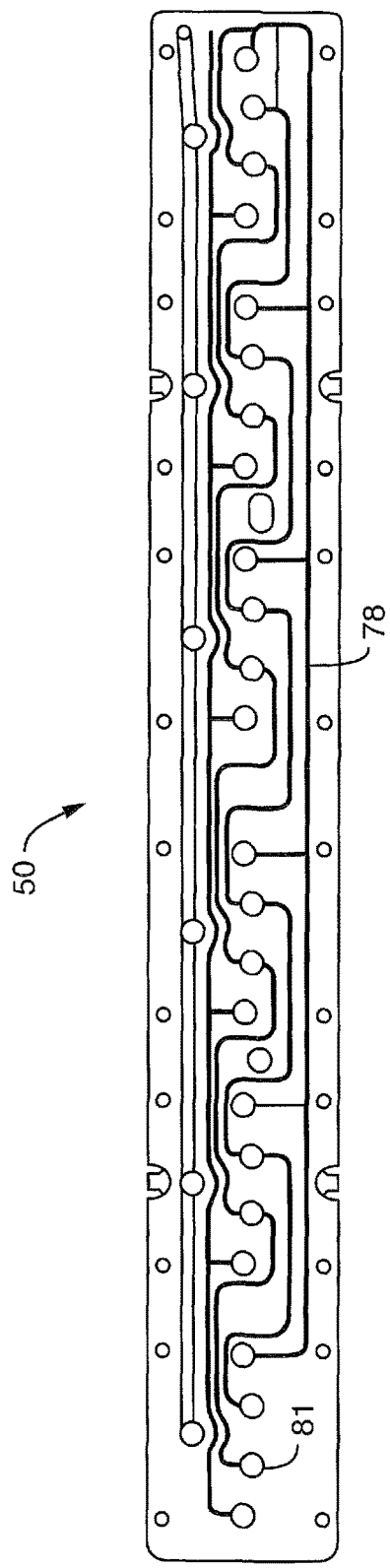
FIG. 10H is a schematic of one embodiment of the pressure manifold (50) showing a top view of the manifold routing channels (78) and one port (81) among many.

A culture module comprising a pressure manifold is contemplated that allows the perfusion and optionally mechanical actuation of one or more microfluidic devices, such as organ-on-a-chip microfluidic devices comprising cells that mimic at least one function of an organ in the body. FIG. 10A is a schematic of one embodiment of the pressure manifold (50) showing the view of the PD engaging face (54) with several PD engaging locations (in this case, six engaging locations). FIG. 10B shows a magnified portion of the engaging face (54) of the pressure manifold (50) highlighting the spring shuttle (55), valve seals (56) and alignment features (57) (so that the PD is aligned with the manifold). The spring shuttle is an optional means by which the pressure manifold may sense the presence of a PD in the particular PD engaging location. In a specific embodiment, the presence of a PD depresses the spring shuttle, which opens one or more valves disposed within the pressure manifold to enable the application of pressure or fluid flow to the PD. In turn, when a PD is absent, the shuttle is not depressed, leaving the valve closed; this is intended to prevent pressure or fluid leakage. The illustrated valve seals are adapted to form pressure and/or fluid seals against corresponding features in the PD and if present, a pressure lid. FIG. 10C is a schematic of another embodiment of the pressure manifold (50) showing the PD engaging face (54), along with an magnified portion highlighting the lid compressor (58), valve seals (56) and alignment features (57) (so that the PD is aligned with the manifold). Lid compressors may apply force onto a pressure lid in order to aid the establishment of maintenance of a pressure and/or fluidic seal between the pressure lid and reservoirs. In one embodiment, the lid compressors comprise springs, elastomeric material, pneumatic actuators or combination thereof, which can be selected and sized to apply a force corresponding to the force required to maintain the said pressure and/or fluidic seal. FIG. 10D is a schematic of one embodiment of the pressure manifold (50) showing the PD engaging face (54) from the side. FIG. 10E is a schematic of one embodiment of the pressure manifold (50) showing the opposite face (67). FIG. 10F is a schematic of one embodiment of the pressure manifold (50) showing the PD engaging face (54) view with the PD guide (68) and lower backer plate (69) removed, highlighting one spring carrier (70) and spring (71) (out of many) by showing it removed from the manifold body, along with one seal (72), shuttle (73), and valve body (74) (out of many) by showing it removed from the manifold body. An exterior spring (75) adapted to depress the pressure manifold against the perfusion disposables is also highlighted by showing it removed. FIG. 10G is a schematic of one embodiment of the pressure manifold (50) showing the opposite face (67) (not the PD engaging face) view with the upper backer plate (76) and capping strip (77) removed. Illustrated are manifold routing channels (78), which are adapted to direct and optionally distribute pressure and/or fluid from one or more pressure ports. Additionally illustrated is one screw (79) (among many) and one gas port (80) (out of five, including both gas and vacuum ports) by showing it removed from the manifold body (50). FIG. 10H is a schematic of one embodiment of the pressure manifold (50) showing a top view of the manifold routing channels (78) and one port (81) among many. The routing channels can be produced using a number of methods known in the art, including molding, machining, ablation, lamination, 3D printing, photolithography and a combination thereof.

Figure 11A:
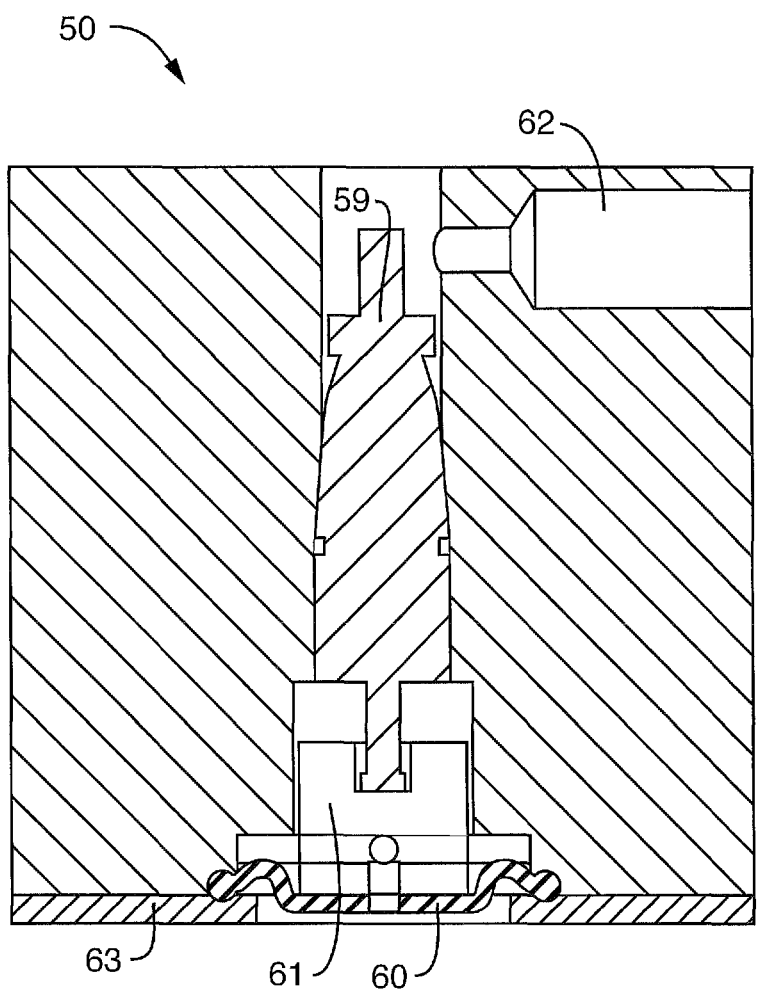
FIG. 11A is a schematic of one embodiment of a valve (59) (a Schrader valve) in the pressure manifold (50), showing the silicone membrane (60), shuttle (61), air inlet (62) and cover plate (63).
Figure 11B:
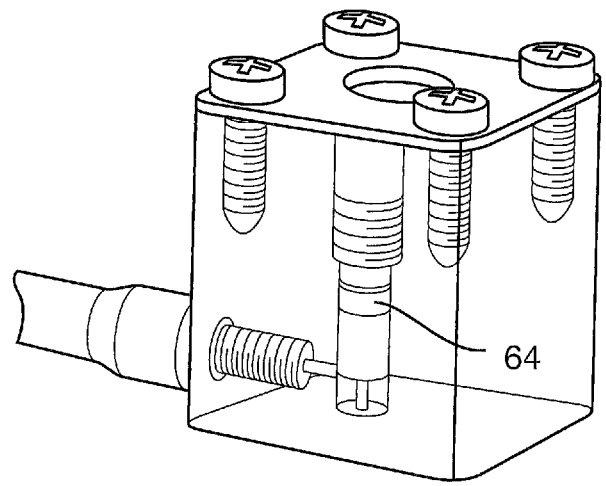
FIG. 11B is a side view and FIG. 11C is a top view photograph of one embodiment of a valve for the pressure manifold, showing the valve seat (64) and a membrane (60) acting as the valve seal.
Figure 11C:
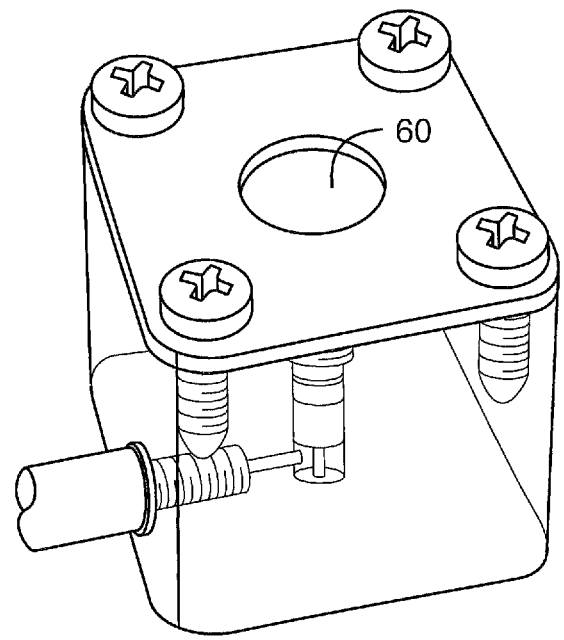

FIG. 11A is a schematic of one embodiment of a valve (59) (a Schrader valve) in the pressure manifold (50), showing the silicone membrane (60), shuttle (61), air inlet (62) and cover plate (63). In this embodiment, the spring shuttle is integrated into the valve and is adapted to depress the Schrader valve's poppet to actuate the valve. FIG. 11B is a side view and FIG. 11C is a top view photograph of one embodiment of a valve for the pressure manifold, showing the valve seat (64) and a membrane (60) acting as the valve seal. FIG. 11D is an interior side view schematic of one embodiment of the pressure manifold (50) showing a plurality of valves (59) in the manifold body, the poppet (65), valve seal (66) and PD cover (11). In operation (to engage the PD), the valve seal (66) deflects with the displacement of the poppet (65).

Figure 12A:
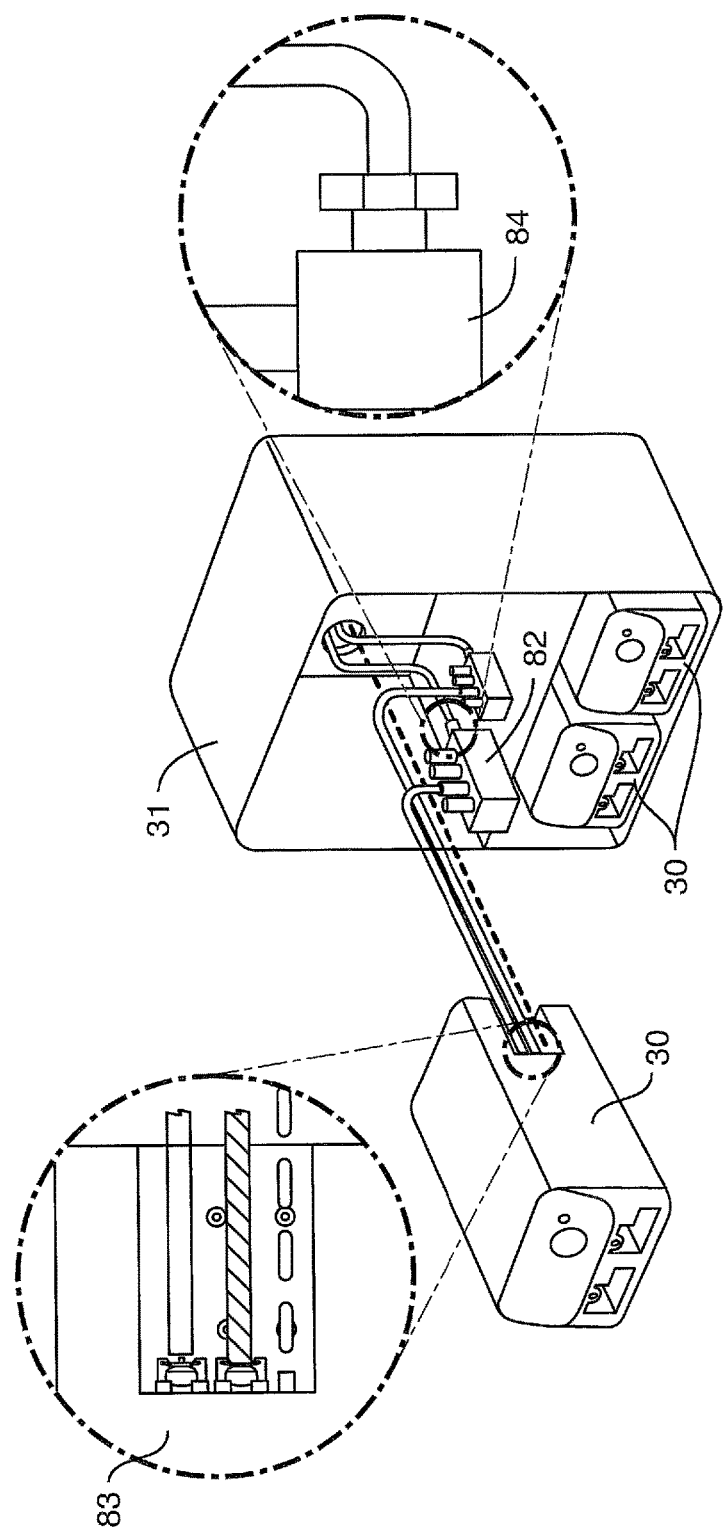
FIG. 12A is a schematic of one embodiment of a connection scheme comprising a tube connecting manifold (82) permitting four culture modules (30) (three are shown) to be connected inside a single incubator (31) using one or more hub modules (the two circles provide magnified views of a first end (83) and second end (84) of the connections).
Figure 12B:
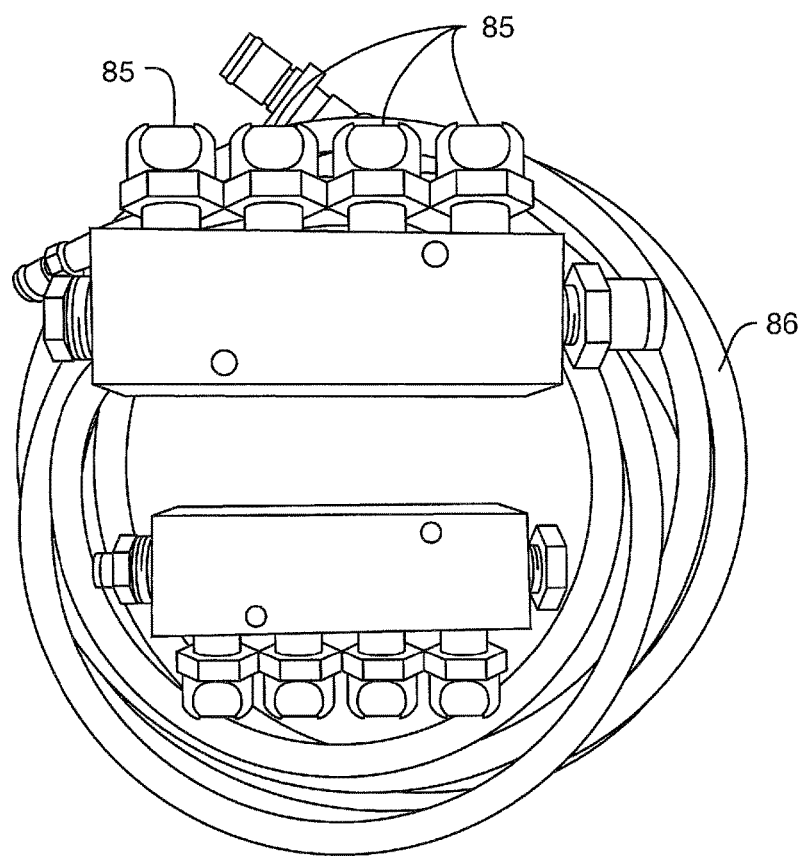
FIG. 12B is a photograph of gas hubs and vacuum hubs (collectively 85), along with the tubing (86) for the connection shown in FIG. 12A.
Figure 13:
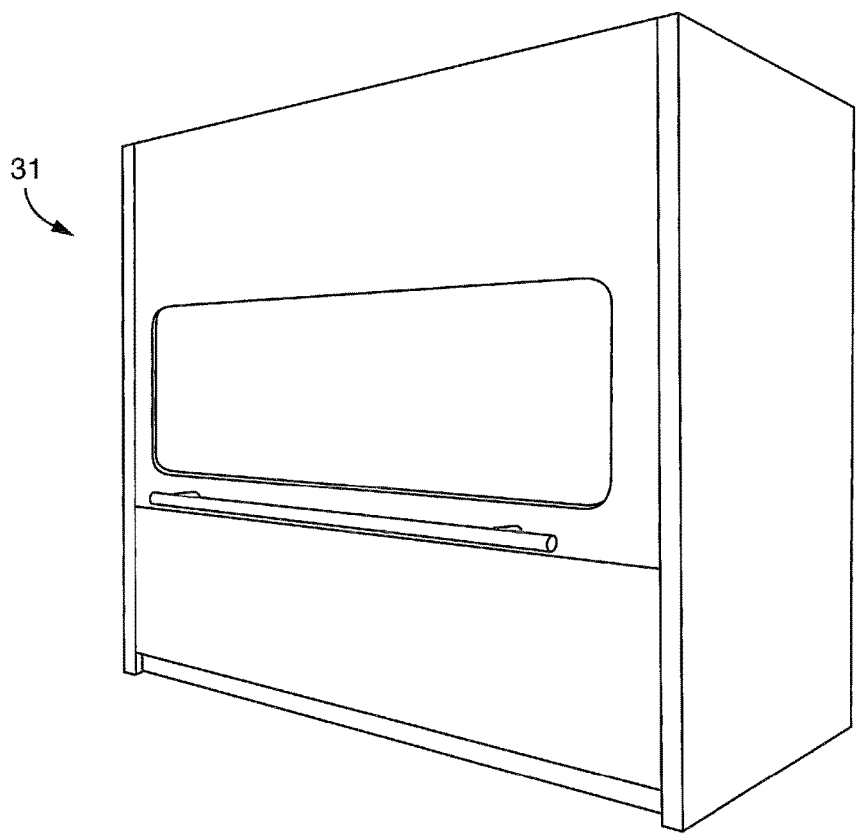
FIG. 13 is a photograph of one embodiment of an incubator (from the outside with the outer door closed) containing shelves (not shown) which can support the perfusion manifold assemblies of the present invention. The incubator may have automated liquid handling, imaging and sensing features for automatic experiments, evaluating cell viability and/or collecting experimental results. In one embodiment, the microfluidic devices are linked during incubation.

FIG. 12A is a schematic of one embodiment of a connection scheme comprising a tube connecting manifold (82) permitting four culture modules (30) (three are shown) to be connected inside a single incubator (31) using one or more hub modules (the two circles provide magnified views of a first end (83) and second end (84) of the connections). FIG. 12B is a photograph of gas hubs and vacuum hubs (collectively 85), along with the tubing (86) for the connection shown in FIG. 12A. While this connection scheme is optional, it provides a convenient way to utilize multiple culture modules with a single incubator.

DETAILED DESCRIPTION OF THE INVENTION

A. Pressure Lid

The present invention contemplates in one embodiment "perfusion manifold assemblies" or "perfusion disposables," which facilitate the culture of Organs-on-Chips within a culture instrument. While the present invention contemplates "disposable" embodiments, the element may (alternatively) be reusable (e.g. as a cost consideration).

In one embodiment, these perfusion disposables (PDs) include one or more input and one or more output reservoirs, as well as elements required for pumping. In particular, in our present embodiment perfusion disposables include one or more resistors (see FIG. 32A), which are used for pressure-driven pumping. In the pressure-driven embodiment, the instrument creates or controls fluid flow by applying a pneumatic pressure (whether positive or negative) to one or more of the reservoirs. One advantage of this approach is that the pressure-driven design can avoid liquid contact with the instrument, which offers benefits in terms of sterility and ease of use (e.g. avoiding gas bubbles in liquid lines). In some embodiments, the instrument applies pressure directly to the one or more reservoirs (with no lid). A sufficient pressure seal may be attained by integrated one or more gaskets on the perfusions disposable and/or the instrument (for example, as part of a pressure manifold). However, it is desirable that when the perfusion disposables are outside of the instrument the reservoirs are protected from contamination, for example, from environmental particles or airborne microbes. Accordingly, in the same embodiments it may be desirable to provide a lid that a user can employ to cover the reservoirs when outside of the instrument and/or to employ PD embodiments that comprise a substrate that conveys pressure but blocks contamination (for example, a suitable filter disposed on a reservoir's opening). However, such solutions typically pose drawbacks. In particular, expecting a user to place a lid requires the user to manage lids while the perfusion disposables are engaged with the instrument and ideally place the lids as soon as the PDs leave the instrument; in most circumstances, these actions adversely affect user experience. In turn, a filter disposed on a reservoir's opening typically blocks access to the said reservoir by pipettes and other typical lab tools, thereby adversely limiting their ease of use.

According to an aspect of the present invention, we disclose a "pressure lid", a lid that may be disposed on a microfluidic device or a device adapted to accept a microfluidic device (e.g. a perfusion disposable) even while the said device is engaged with an instrument, with the pressure lid adapted to permit the communication of pressure between the instrument and the said device. The present invention contemplates that in some embodiments, a pressure lid is a removable cover adapted to be disposed onto one or more reservoirs of a microfluidic device or a device adapted to accept a microfluidic device (e.g. a perfusion disposable), the pressure lid comprising at least one instrument-interface port and at least one reservoir-interface port, wherein the pressure lid is adapted to convey pressure between at least some of the instrument-facing port and at least some of the reservoir-facing ports. In some embodiments, the pressure lid comprises at least one "through hole" port—an opening that connect a first and second surface of the lid, wherein the opening on the first surface is adapted to form an instrument-facing port and the opening on the second surface is adapted to form a reservoir-facing port. In some embodiments, the though-hole port is round, rectangular, triangular, polygonal, rectilinear, curvilinear, elliptical, and/or curved. In some embodiments, however, the lid comprises a channel that links at least one instrument-facing port and at least one reservoir-facing ports, which may not be disposed directly opposite each other. Such embodiments may be useful, for example, where there is a need to adapt between locations of instrument interface and reservoir locations, for example, when it is desired for the same instrument to support the actuation of a plurality of versions of perfusion disposables.

In some embodiments, the pressure lid is adapted to form a pressure seal between said pressure lid and at least one reservoir. In some embodiments, the pressure lid is engaged with at least one reservoir forming a lid-to-reservoir pressure seal. In some embodiments, the pressure lid is adapted to form a pressure seal between said pressure lid and at least one instrument. In some embodiments, the pressure lid is engaged with at least one instrument forming a lid-to-instrument pressure seal. Any of the lid-to-reservoir seals and lid-to-instrument seals may employ any sealing methodology known in the art and can be selected for example, from the list of face seal, radial seal, tapered seal, friction fit or a combination thereof. Any of the said seals may employ one or more gaskets, O-Rings, elastic materials, pliable materials, adhesive, sealants, greases or combination thereof. It is not intended that the present invention be limited to a design that has a perfect pressure seal, as this may not be required. Rather, some amount of gas leakage can be tolerated, since the instrument may actively regulate pressure, thereby compensating for the leak. The relaxing of a requirement to obtain a perfect seal on one or both sides can simplify design and reduce costs.

In some embodiments, the pressure lid comprises a load concentrator. For example, in some embodiments, the pressure lid comprises a ridge surrounding at least one instrument-facing port. In some embodiments, the pressure lid comprises a ridge surrounding at least one reservoir-facing port. It is known in the art that such load concentrators can act to improve pressure seals by enhancing reliability or reducing the required force; designs known in the art include, for example, rectangular, semi-circular, triangular, trapezoidal and polygonal ridges. Accordingly, a load concentrator surrounding an instrument-facing port may be employed to improve a lid-to-instrument pressure seal, and a load concentrator surrounding a reservoir-facing port may be used to improve a lid-to-reservoir pressure seal.

In some embodiments, the pressure lid comprises a filter. For example, the pressure lid may comprise a membrane filter, sintered filter, fiber-based filter and/or track-etched filter. In some embodiments, the said filter is disposed within or abutting a through-hole port and/or one of its openings. In some embodiments, the said filter is disposed within or abutting a channel included in the lid and/or one of the openings of said channel.

In some embodiments, the filter is selected to improve the sterility of a reservoir and/or block particles, contaminated or microbes. In some embodiments, the filter feature an effective pore size of 0.4 um or less, 0.2 um to 2 um, 1 um to 10 um, 5 um to 20 um, 10 um to 50 um. It is known in the art that filters that feature an effective pore size of 0.4 um or less are preferable for maintaining sterility. However, a filter such as the Porex 4901 possess a 25 um effective pore size has been shown to be effective in maintaining sterility.

In some embodiments, the pressure lid comprises one or more gaskets. In some embodiments, the one or more gaskets are adapted to permit or improve a pressure seal (which may nevertheless not be a perfect seal). In some embodiments, at least one gasket is disposed on a reservoir-contact surface of the said lid. In some embodiments, at least one gasket is disposed on an instrument-contact surface of the said lid. In some embodiments, a gasket is adapted to permit or improve pressure seals with a plurality of reservoirs. In some embodiments, a gasket is adapted to permit or improve pressure seals at a plurality of instrument-facing ports. In some embodiments, the one or more of the gaskets comprise an elastomer, pliable material, O-Ring and/or a combination thereof. In some embodiments, one or more of the gaskets are formed by extrusion, casting, injection molding (including reaction-injection molding), dye cutting and/or a combination thereof. In some embodiments, at least one gasket is mechanically coupled to the lid by adhesion (e.g. using adhesive tape), clamping, screwing down, bonding, heat-staking, welding (e.g. ultrasonically, by laser), fusing (e.g. using solvent-assisted bonding), and/or a combination thereof.

For example, one of our present embodiments of the lid includes a port (5) that allows pneumatic (e.g. vacuum) control of (optional) chip stretching to be communicated through the lid (see FIGS. 2A-2E). It is not intended that the lid be limited to communicating only pneumatic pressure; it is contemplated that the lid can communicate additionally fluidic or electrical interfaces.

In one embodiment, the lid can include sensors. For example, the lid may comprise a pressure sensor to determine, for example, the pressure incident on one or more reservoirs. Further, the lid may include liquid-level sensing to determine the amount of liquid present in the reservoir or whether specific fill (or depletion) thresholds have been passed. This can be done in a variety of ways. In one embodiment, the detecting liquid optically using the difference of refractive indexes is contemplated. In this embodiment, air-filled compartments and channels disperse light, while liquid or fluid-filled channels focus light. More specifically, the refractive indexes of liquid are from 1.3 to 1.5 while that of air is only 1.0. In one embodiment, each optical sensor consists of a matched pair of an IR emitter (SEP8736, 880 nm, Honeywell) and a phototransistor (SDP8436, 880 nm, Honeywell). In this embodiment, IR is chosen over visible light for it is less susceptible to interfering light.

The ability to easily remove fluids from the various reservoirs (e.g. take sample, replenish media, add test agents, etc.) is a desired feature. An especially desired feature is to be able to use standard laboratory pipettes and syringes for such operations. However, such fluidic access (especially using a pipette) requires the accessed reservoir to be open to the environment. This, in terms, is undesirable particularly when the chip or disposable are in transit or in use outside of the instrument, as the opening can provide a means for contamination of the reservoir. A typical solution to this problem is to include a lid that can be applied to one or more of the reservoirs when they are not being accessed. However, including a simple lid can complicate the use of the technology, since the user typically would have to actively install and remove the lid, as well as maintain lids near the instrument in a sterile way.

One solution is to include a means for automatically removing and/or installing lids as part of the system (whether integrated in the culture instrument or a separate module). For example, the system can include a mechanical actuator that is capable of engaging a lid installed on a disposed perfusion disposable and removing it prior to engagement with the pressure system. This mechanical actuator can re-install the lid upon removal of the perfusion disposable. In an alternate embodiment, the system includes a means for applying a lid to a perfusion disposable prior to or upon removal, for example, with the lid originating from a magazine of stored lids.

A shortcoming of the system with the means for automatically removing and/or installing lids (discussed in the prior paragraph) is that it requires one or more mechanical actuators whose operation can be challenging in practice. Another challenge is the following: the design of the reservoirs and in particular its opening aims to satisfy the demands of liquid access (e.g. manual sample taking or replenishing using a pipette), the pressure-driven system (e.g. ensuring a good pressure seal against the instrument) and manufacturing (e.g. injection-molding of the reservoirs). In practice, these requirements can oppose each other. For example, manual access may demand a broad reservoir opening; in contrast, it may be desirable for the pressure interface to be narrower, to reduce the force on the instrument.

A better solution disclosed herein is to include a "pressure lid" (see FIGS. 2A, 2B, 2C and 2D). This pressure lid is a lid that may be installed on to the reservoirs to reduce the likelihood of contamination, and is designed to stay predominantly in place while the perfusion disposable is engaged with the instrument. In order to stay predominantly in place while engaged with the instrument, the lid preferably includes a) one or more features designed to interface with the instrument (e.g. to received positive or negative pressure), b) one or more features designed to interface with one or more reservoirs (e.g. create a pressure seal or minimize gas leakage so that pressure can be applied to the reservoir), and c) a means for pressure to be communicated from at least some of the features (a) and at least some of the features (b). The pressure lid or portions thereof may be transparent or translucent. This can allow, for example, viewing liquid levels within the reservoirs. The pressure lid may include markings that indicate the nature or name of respective reservoirs.

In one embodiment of the pressure lid, the opening in the pressure lid (e.g. on its top) may be smaller than the reservoir, to reduce the surface area open for contamination and/or reduce the area subject to a pressure seal. In another embodiment, the lid may include a filter or a plurality of filters (38) to prevent solids and particles from entering (see FIG. 2A). For example, the lid may include a 0.2 um or 0.4 um filter known to reduce entry of bacteria and other contaminants. Many materials and technologies can be used for such filters. For example, track-etched filters (e.g. PTFE, polycarbonate, PET), paper filters, porous and expanded materials (e.g. cellulose and derivatives, polypropylene, etc.), sintered materials (e.g. Porex filters) may be used since the filter need only conduct pressure and not liquids.

In one embodiment, the lid may include a means for permitting gas flow but predominantly no liquid flow. This can include, for example, hydrophobic porous membranes or filters, gas permeable membranes or filters, etc. This approach can also help reduce the likelihood of spillage.

In one embodiment, the lid may include a deformable portion that can deform to conduct pressure. For example, this can be an elastic or plastic membrane that stretches into the reservoir as positive pressure is applied. Similarly, the lid may include a plunger used to transmit pressure from the instrument to one or more reservoirs. Care must be taken to ensure that the desired pressure is applied to the inside of the reservoir, as the membrane or plunger can apply a back force. This can be done, for example, by a) ensuring that the back force is small or understood through design of the membrane, plunger or the operating pressure range, b) measuring the pressure inside the reservoir and using it to control the applied pressure, c) monitoring the resulting flow to control the applied pressure. The deformable portion offers one way for pressure to be communicated.

Either side of the pressure lid (instrument-facing or perfusion disposable-facing) as well as each of the opposing surfaces (instrument and perfusion-disposable features that interact with the pressure lid) can be designed to enable a pressure seal in a number of different ways. In one embodiment, the present invention contemplates one or more regions comprising one or more elastic or pliable materials. In one embodiment, this is done with one or more gaskets (see FIG. 2A), which can be made for example from elastomeric or pliable materials (e.g. silicone, SEBS, polypropylene, Viton, rubber, etc.). The gaskets can be shaped in a variety of ways, including cut flat sheets, o-rings (not necessarily round in shape or cross-section), etc. In one embodiment, this is done with one or more ridges that act as load concentrators (see FIG. 2C). Without wishing to be bound by theory, these act to localize the sealing force to create elevated localized sealing pressure. These ridges may potentially engage a gasket or pliable material on the opposing surface. Care must be taken to design the shape of the ridge (particularly the portion of the shape that engages the opposing surface), as this shape can have a substantial effect on the required sealing pressure. A variety of shapes are contemplated (e.g. rectangular, triangular, trapezoidal, half-circular or circular section, etc.). In one embodiment, the sealing tooth has a trapezoidal shape for improved sealing (see FIG. 2C). Alternatively, the gasket could be integrated into either the Reservoir or Lid in the form of an overmolded elastomer (e.g. silicone, SEBS, etc). This overmolded elastomer could then, itself, have an appropriate shape to act as a seal (e.g. a tooth or o-ring half-round section).

The approach need not be limited to a single design. In one embodiment, the present invention contemplates a combination of one or more regions comprising one or more elastic or pliable materials. Moreover, gasketing or ridges can be done per-reservoir, so that each is isolated in terms of applied pressure, or it can encompass two or more reservoirs, which may reduce complexity. In one embodiment (see FIG. 2D) the path encircles all chambers of the reservoir chamber-cover assembly seal, so each chamber is isolated from the other. In one embodiment (see FIG. 2D), there are two reservoirs, each with an inlet chamber (6A, 6B) and an outlet chamber (7A, 7B), and a separate (optional) vacuum chamber (8) that allows for transfer of a vacuum to the chip or other microfluidic device. In one embodiment (FIG. 2E), the reservoir chamber-cover assembly seal comprises a sealing tooth (9).

It is not intended that the present invention be limited to a design that has a perfect pressure seal, as this may not be required. Rather, some amount of gas leakage can be tolerated, since the instrument may actively regulate pressure, thereby compensating for the leak. The relaxing of a requirement to obtain a perfect seal on one or both sides can simplify design and reduce costs.

The pressure lid can be affixed or rest upon the reservoirs (whether on the perfusion disposable or directly on chip) in a variety of different ways. Embodiments can involve instances wherein the liquid or gas seal between the lid and reservoir(s) is present even outside of the instrument (e.g. the lid is held tightly in place by something other than the instrument), and wherein the seal is created by action of the instrument (e.g. the instrument presses the lid against the reservoirs during perfusion). In another embodiment, the present invention contemplates a combined approach, e.g. the lid is designed to create at least a partial seal as in the first option above, but the seal is approved or assured by action of the instrument as in the second option above. An advantage of approaches that provide at least some degree of sealing of the lid against the reservoir even outside of the instrument is that they may reduce the risk of spills and contamination (e.g. due to handling or transport).

Examples of approaches to affix or rest the pressure lid (regardless of which of the above three approaches they fall under) include a) where the lid can simply rest upon the reservoirs or perfusion disposable (this can be aided by overhanding portions of the lid, so that the lid cannot simply slide off); b) the lid can be screwed, glued or pinned into place; and c) the lid can be clipped into place. In an alternative embodiment, it could also be held down by a spring, e.g. a hinged lid with a spring that forces the lid closed.

Clip features may reside in the lid, the perfusion disposable, chip or combination thereof. Furthermore, some embodiments make use of a separate substrate that provides clipping elements (i.e. a separate piece that one brings in to clip the lid into place). An advantage of the clipping approach is that it can facilitate easy application and removal of a lid while still securing the lid in place. The clipping may be optional; for example, it may be applied when shipping or transporting the device and ignored during regular use.

In some embodiments, the lid is asymmetric or includes lock-and-key features to ensure that the lid is correctly oriented with respect to a perfusion disposable and/or an instrument.

Many of the features of the perfusion disposable (PD) could potentially be included in the "chip" itself or a different device for coupling to a chip. If the reservoirs, for example, are included in the chip, one could use a pressure lid directly on top of the chip.

While the pressure lid has been discussed above in connection with the pressurization of one or more reservoirs within a perfusion disposable or perfusion manifold assembly, it is not intended that the pressure lid be limited by use with only these embodiments. Indeed, it is contemplated that the pressure lid can be used with other microfluidic devices. The pressure lid can be movable or removably attached to other microfluidic devices to allow improved access to elements (e.g. reservoirs) within. The pressure lid can be removed from such other devices, and the other devices can be used without the lid. In one embodiment, the other microfluidic devices comprise cells on a membrane and/or in or on one or more microchannels.

B. Tray System

It is desirable to be able to remove chips and/or perfusion disposables from the instrument without having the remove the instrument itself from, for example, an incubating enclosure. It is also desirable to be able to remove groups of chips and/or perfusion disposables together. This is because the operations that are performed on the chips/disposables often need to be done in batches at a time (e.g. media replenishing, dosing with an agent, sample taking), regardless of whether the operations are performed automatically or manually. For example, it is convenient to remove groups of chips/disposables at a time if only to help transport them to a bio-safety cabinet or culture hood.

Figure 6:
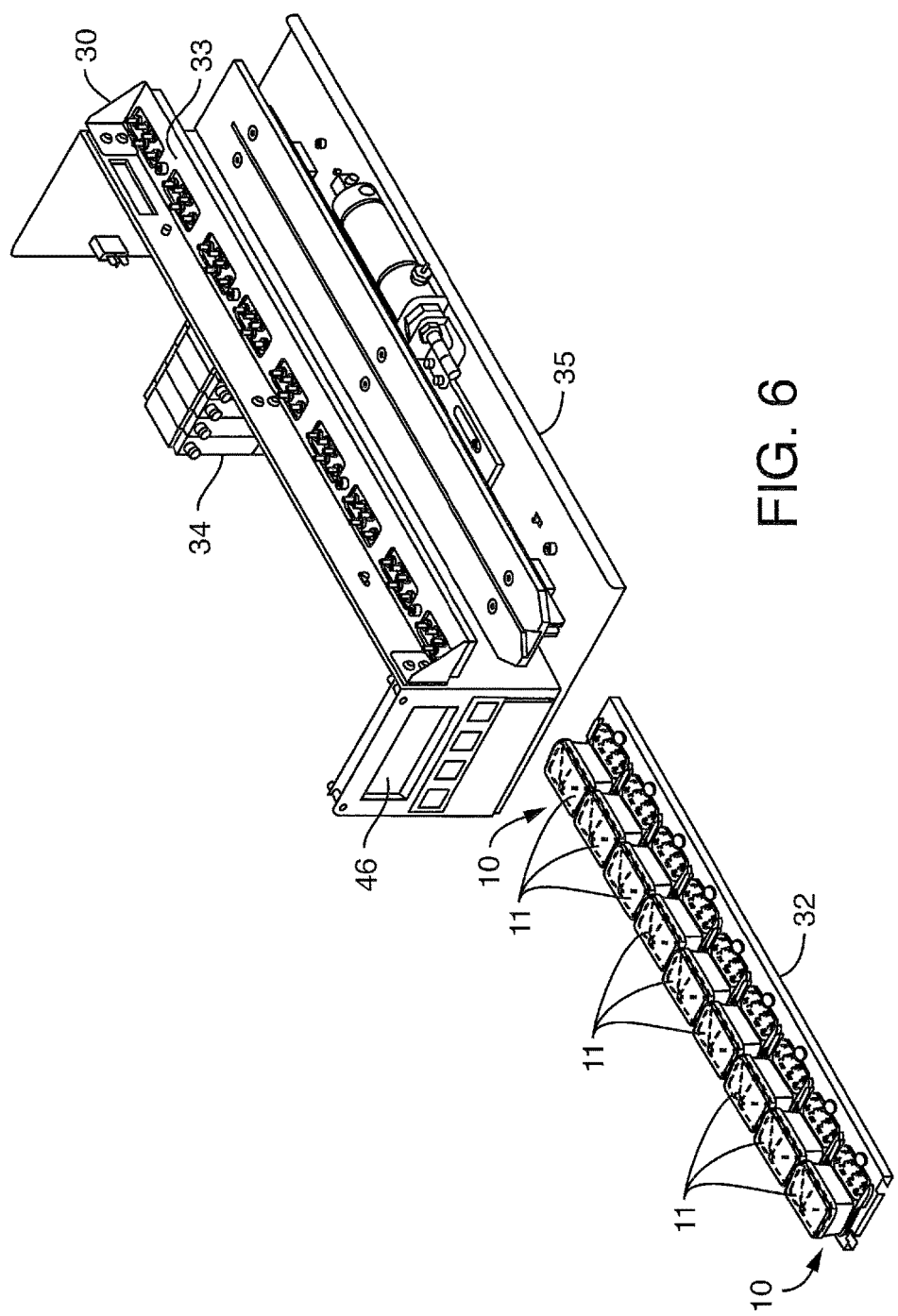
FIG. 6 shows one embodiment of a removable tray with a plurality of assemblies (with linked chips) positioned thereon, next to one embodiment of a culture module with pressure points on a mating surface that correspond to the ports on the cover of each perfusion manifold assembly held in the tray, such that they can be brought together by the tray mechanism so that pressure can be applied via the pressure controllers. The tray mechanism thereby attaches all of the perfusion manifold assemblies to pressure or flow controllers in a single action (whether lifting the tray up or coming down to meet the tray), allowing for a simultaneous linking.
Figure 7:
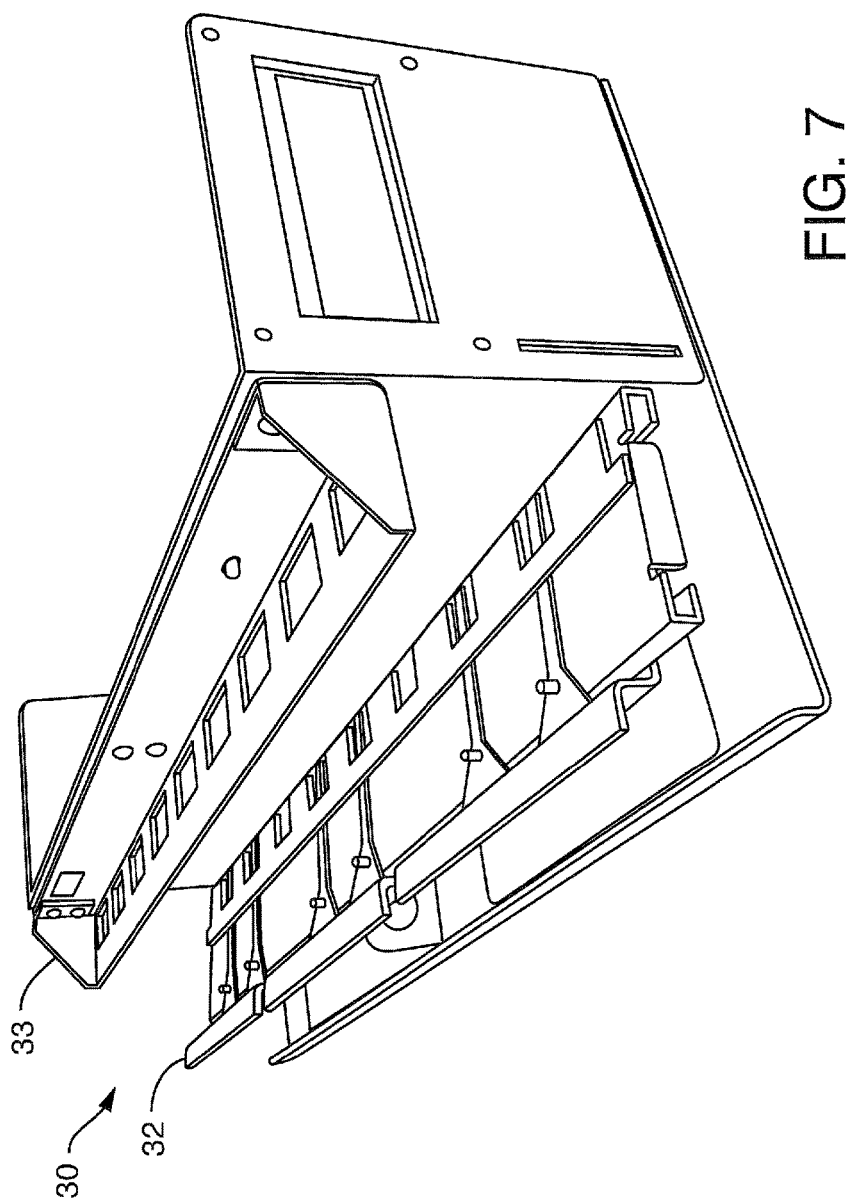
FIG. 7 is a schematic of another embodiment of a culture module from the side, showing the platform for positioning the removable tray which is moved upward into a mating surface so that pressure can be applied through the pressure controllers (not shown).

To address these needs, the present invention contemplates, in one embodiment, a system in which perfusion disposables can be inserted or removed from an instrument (or module) in groups by means of a tray system (see FIG. 6). For example, a current embodiment allows each instrument to accept two trays (or racks) of six perfusion-disposables each (8A and 8B).

In one embodiment, the tray (or rack) (32) may facilitate the alignment of the perfusion disposables (10) with the instrument (30) (e.g. aligning reservoirs or port locations with corresponding pressure or fluid interfaces included in the instrument). This can be done in a number of ways, including providing locating features for the perfusion disposables (or any additional elements that carry them) within the tray, and providing locating features for the tray within the instrument and alignment features (57) for the perfusion disposables (see FIG. 10B). Features that can be used to support such alignment include reference surfaces, pins, guides, shaped surfaces (e.g. fillets and/or chamfers), spring or elastic elements to promote registration, etc. These may be included in the tray, instrument, perfusions disposables or combinations thereof.

The tray may optionally be designed to capture leaks originating from the perfusion disposables or instrument interfaces. The tray may optionally include one or more optical windows that may facilitate microscopy or inspection. This can enable placing a tray onto a microscope or other inspection device, allow the chips to be observed without having to remove each disposable from the tray. Correspondingly, the tray may be optionally designed to minimize imaging working distance, e.g. lay flat on or fit into a microscope stage, etc. The system may optionally include a means for retaining one or more of the perfusion disposable within the tray. For example, the perfusion disposable may clip into the tray, with clip features present on the perfusion disposable, tray, an additional substrate or combinations thereof.

In some embodiments, the tray system includes one or more sub-trays (or nests) (47) that fit into a carrier tray (32) (see FIG. 8A). Sub-trays allow subsets of perfusion disposables (e.g. three) to be removed from the tray simultaneously. This can be useful, for example, where one or more operations performed on the chips/disposables benefits from a smaller number of chips that are present on the carrier tray. For example, in some instances, we prefer to place no more than three disposable on a microscope stage at one time, to minimize the time that the chips/disposables spend outside of their preferred incubation and perfusion environments. Consequently, a current embodiment includes carrier trays (32) that support two sub-trays (47) each, each sub-tray supporting three perfusion disposables (10) (see FIG. 8A).

The sub-trays may facilitate the alignment of the perfusion disposables with the instrument. This can be done in a number of ways, including by providing locating features for the perfusion disposables within the tray, by providing locating features for the sub-tray within the carrier tray, and by providing locating features for the carrier tray within the instrument. Features that can be used to support such alignment include reference surfaces, pins, guides, shaped surfaces (e.g. fillets and/or chamfers), and spring or elastic elements to promote registration, etc. These may be included in the carrier tray, sub-tray, instrument, perfusions disposables or combinations thereof. By way of an example, the present invention contemplates an embodiment wherein the perfusion disposables align to the sub-tray, which in turn aligns to the carrier tray, which in turn aligns to the instrument (see FIGS. 9A and 9B). It is not intended that all of these alignments or necessary; indeed, some steps in this chain may be skipped. For example, the sub-tray may align directly to the instrument using any of the described features, and not requiring the carrier tray for alignment purposes.

The sub-tray may optionally be designed to capture leaks originating from the perfusion disposables or instrument interfaces. The sub-tray may optionally include one or more optical windows that may facilitate microscopy or inspection. This can enable placing a sub-tray onto a microscope or other inspection device, allow the chips to be observed without having to remove each disposable from the tray. Correspondingly, the sub-tray may be optionally designed to minimize imaging working distance, e.g. lay flat on or fit into a microscope stage, etc. The system may optionally include a means for retaining one or more of the perfusion disposables within the sub-tray. For example, the perfusion disposable may clip into the sub-tray, with clip features present on the perfusion disposable, sub-tray, an additional substrate or combinations thereof. The system may optionally include a means for retaining the sub-tray within the carrier tray. For example, the sub-tray may clip into the carrier tray, with clip features present on the sub-tray, carrier tray, an additional substrate, or combinations thereof.

It may be convenient to divide some of the desired features between the carrier tray and the one or more sub-trays. For example, the sub-trays can provide an optical window and the carrier tray can be designed to capture leaks. As this example illustrates, it may be desired to include a sub-tray even if the carrier tray is designed to support only one sub-tray.

The same instrument may support different tray or sub-tray types, as well as different numbers of trays. For example, an instrument may accept two different tray types, each tray type designed for a different type of perfusion disposable. In such a case, the tray can in essence act as an adaptor that adapts the different perfusion-disposable types to the same instrument.

The present invention also contemplates in one embodiment, microscope stages, stage-inserts or adapters (e.g. that plug into the stage inserts) designed to accept one or more chips, perfusion disposables, trays or sub-trays. These can make it easy to "drop in" a number of chips for imaging, with the chips securely retained on the stage (thereby avoiding drift, for example, as the microscope stage moves).

C. Engaging Perfusion Disposables with the Instrument

In one embodiment, the present invention contemplates a pressure-driven system for the biological culture in fluidic devices, which applies pressure (whether positive or negative) to one or more fluidic elements. These fluidic elements can include, for example, chips, reservoirs, perfusion disposables, pressure lids or combinations thereof. In such system, the instrument interfaces with the respective fluidic element or elements in order to apply the pressure where desired. Such interfacing typically involves establishing a gas seal, although in some embodiments a tight seal is not required (e.g. the pressure-regulation can maintain the desired pressure despite gas leak). Without loss of generality, the following description refers to establishing a seal, but the intent is to also encompass embodiments that do not require a seal.

In the present disclosure, a system and method are contemplated for establishing a pressure interface between a biological culture instrument and one or more fluidic elements. In particular, a system is contemplated wherein, in one embodiment, the one or more fluidic elements are lifted into contact with one or more pressure manifolds included in the instrument, the said one or more pressure manifolds are lowered into contact with the said one or more fluidic elements, or a combination thereof. In some embodiments, the said raising or lowering engages multiple fluidic elements with the instrument in unison (e.g. through a single operation or single movement) (see FIGS. 9A and 9B), simultaneously linking a plurality of microfluidic devices (such as one or more of the embodiments of the perfusion manifold assembly discussed herein).

Some embodiments wherein the fluidic elements are raised include one or more platforms onto which one or more of the fluidic elements are disposed. In such embodiments, one or more of the platforms may be raised in order to affect the said raising of the one or more fluidic elements (FIG. 6). In some embodiments, the instrument or system includes a mechanical means (35) for manually achieving the said raising or lowering involved in the said establishing of a pressure interface. Such mechanical means (35) for manual actuation can include the moving of a user-accessible control surface, which may include, for example, a level, pull/push knob, rotational control, or combinations thereof.

In some embodiments, the instrument or system includes a mechanical actuator (51) in order to facilitate the raising or lowering involved in the said establishing of a pressure interface (See FIGS. 9A and 9B). Such mechanical actuator can involve, for example, one or more pneumatic components (52) (e.g. cylinders), hydraulic components (e.g. cylinders), solenoids, electrical motors, magnets (e.g. fixed magnets mechanically moved into place), or combinations thereof. In some embodiments, the mechanical actuation can be under computer control. In some embodiments, the mechanical actuation is augmented with manual control (e.g. using any of the means for mechanical control described above), for example, in order to provide a manual override. A user interface on the instrument can control this process.

Regardless of whether the actuation is manual or automatic, the system can, in some embodiments, further include one or more mechanisms for increasing the applied mechanical force. This may be desirable in order to provide sufficient force on the pressure interface in order to obtain a sufficient or sufficiently robust seal. Such mechanisms for increasing the applied mechanical force can include levers, cams, pneumatic or hydraulic amplifiers, or combinations thereof.

In some embodiments, the mechanical motion can be controlled and or constrained using various mechanical components or designs known in the art. These mechanical components or designs include, for example, rails, guide rots, pivots, cams, four-bar linkages, etc. It is important to note that the raising or lowering motion can, but need not, be linear. For example, a rotational motion (e.g. in the case of a pivot) or a compound motion (e.g. in the case of a linkage) are desirable in some embodiments.

Although the forgoing describes raising or lowering and features present on the top of bottom of various substrates, one with typical skill in the art would appreciate that the description can also be applied to lateral motions or motions along other axes (and not necessarily linear motions), and to features present on any sides or orientations. Additionally, although the forgoing implies that the one or more fluidic elements are disposed beneath the one or more pressure manifolds, one with typical skill in the art would appreciate that the said pressure manifolds may instead lie beneath the said fluidic elements (for example, the pressure interfaces may be disposed on the bottom surface of a perfusion disposable).

A current embodiment (illustrated in the attached figures) includes two mechanics, each of which permits 6 perfusion disposables to be interfaced with a pressure manifold (50) in a single motion. In this embodiment, the pressure manifolds are lowered (FIG. 9B) into contact with the perfusion disposables (or optionally in contact with pressure lids covering the perfusion disposables) using an electrically controlled pneumatic actuator. The force of the actuator is directed using a cam system, which also increases the applied force due to its mechanical advantage. The illustrated mechanism is also bi-stable, i.e. once the actuator pushes the manifold up or down it can be unpowered, while maintaining the position of the manifold. This can help with heat reduction.

D. Pressure Manifolds and Distribution Manifolds

In many applications of the pressure-driven system, it is desirable to distribute one or more pressure sources to two or more fluidic elements (including, for example, fluidic chips, perfusion disposables, reservoirs, pressure lids, or combinations thereof). For example, it may be desirable for two or more perfusion disposables to share a single set of pressure regulators in order to reduce the number of regulators in the system (e.g. in contrast with providing a different set of regulators for each perfusion disposable).

In one aspect of the present disclosure, the instrument includes one or more distribution manifolds. The said distribution manifolds includes one or more fluidic conduit (e.g. gas channels or tubes) adapted to distribute one or more pressure sources to two or more fluidic elements (e.g fluidic chips, perfusion disposables, reservoirs, pressure lids, or combination thereof). Correspondingly, the distribution manifold may include one or more pressure input ports, which may for example be adapted to communicate with one or more pressure regulators (each input port may communicate with a single or multiple regulators). The distribution manifold, in one embodiment, can also have pressure regulation components (valves, pressure sensors, pressure source) integrated into the manifold itself. Similarly, the distribution manifold may include two or more interfaces, which may for example be adapted to communicate with one or more fluidic elements. In some embodiments, the two or more interfaces include at least one region comprising an elastomeric or pliable material. Examples include gaskets, o-rings, etc. made of materials including silicone, SEBS, polypropylene, rubber, Viton, etc. Such regions comprising an elastomeric or pliable region can aid in providing or improving a fluidic seal. Such elastomeric or pliable regions can also be included in pressure manifolds that are not distribution manifolds to provide similar advantages.

In addition to distributing pressure that can be used, for example, to produce pressure-driven flow, the distribution manifold may distribute pressure used for other purposes, for example, to produce mechanical strain or compression (e.g. in actuating mechanical forces in organs-on-chips), to create gas flow within the fluidic element. Moreover, the distribution manifold may optionally distribute one or more liquids. Such liquids can include, for example, wash solutions, disinfectant solutions, working liquids (e.g. for liquid-handling or flow control purposes), tissue-culture media, test agents or compound, biological samples (e.g. blood), or combinations thereof. In some embodiments, the distribution manifold may comprise a working fluid, a membrane and/or a plunger disposed to conduct pressure. For example, a working fluid may be used to reduce the amount of gas required in order to establish a desired pressure, or to facilitate more precise volumetric control. A membrane, plunger and/or working fluid can be used to isolate fluids used in different parts of the distribution manifold (e.g. isolate 5% CO2 tissue-culture gas on the "reservoir side" of the distribution manifold from dry air on the actuation side).

In many applications, it is desirable to enable proper function of the instrument even when fewer fluidic elements are engaged than the instrument can accept. For example, it is often desirable that an instrument that includes a distribution manifold designed to interface with six perfusion disposables still support proper operation of the instrument when only four perfusion disposable are present. For example, it may be undesirable to gas escape through the interfaces intended for the missing perfusion disposables, as such gas escape may reduce gas pressure or deplete gas supplies. Such considerations are relevant even without a distribution manifold (i.e. with a non-distributing pressure manifold).

According to one aspect of the present disclosure, a pressure manifold (or specifically a distribution manifold) can include one or more valves adapted to controllably shut-off one or more of the fluidic (e.g. gas) conduits included in the manifold. A variety of valves suitable are known in the art, including for example pinch valves, screw valve, needle valve, ball valves, spring-loaded valves, poppet valves, umbrella valves, Belleville valves, etc. In some embodiments, one or more of the valves are controlled by a user. For example, a user may configure the valves to match the configuration of perfusion disposables in use. In some embodiments, one or more of the valves are controlled electronically. For example, software may configure the valves according to knowledge of experimental settings or other information available to it. In some embodiments, one or more of the valves are controlled by sensing whether the intended fluidic element is present, for example, in order to shut off a gas line if the fluidic element is missing. Such sensing can involve electrical means (e.g. contact switches, conductors closing circuits), optical means (e.g. optical gates), magnetic means (e.g. magnetic switches), or mechanical means (e.g. levers, buttons). In some embodiments, one or more of the sensing elements affects one or more of the valves by means of interposed software or electronic hardware. In some embodiments, one or more of the sensing elements affects one or more of the valves directly (e.g. by mechanical coupling or by electrically signaling to the valve). As a specific example, the presence of a perfusion disposable can act to depress a protruding feature, which in turn affects the state of a valve. In some embodiments, such configuration lends itself well, for example, to pinch valves, spring valves, poppet valves, or umbrella valves, as the depressed protruding feature can act directly on the valve to augment flow.

In some embodiments, it is desirable or convenient to include the said one or more valves at one or more of the interfaces to the fluidic elements. This may be desirable, for example, since a number of successful valve designs are known that respond to a force present at their outlets. Examples of such valves include Schrader valves, Dunlop valves, Presta valves, umbrella valves, their modifications, and related valves. As a specific example, a Schrader valve may be integrated at an interface to a pressure lid such that when the pressure lid is present, it acts to depress the central stein of the Schrader valve, thereby allowing gas flow.

Valves suitable for inclusion in the interfaces to the fluidic element as described above often have their control feature (e.g. the pin of a Schrader valve) (FIG. 11A) located in the middle of the valve. This, however, can pose a difficulty in some potential embodiments, since a corresponding feature must be provided on the fluidic element to depress such a central control feature. An alternative approach is described herein. As illustrated in FIGS. 11A and 11D, the pressure manifold (50) or distribution can manifold can include a valve (59) such as a Schrader valve (or any listed above) and further include a shuttle (61). The said shuttle includes a first surface that faces the location of a potential fluidic element, and a second surface that faces the said valve. The first surface is designed to accept contact from the fluidic element at the desired location. For example, the first surface can be designed to accept contact from the periphery of a port that may be present on, e.g., a pressure lid (11) (FIG. 11D). The second surface, in term, is design to mechanically engage the said valve's control surface, which may for example lie in the center of the valve. A further advantage of this approach is that the thickness of the shuttle can be adjusted, for example, to control at what distance from the fluidic element the valve will open.

As further illustrated in the FIGS. 11A and 11C, the interface can be optionally covered at least in part by an elastic, pliable or deformable substrate, such as a pliable membrane (e.g. silicone membrane) (60). The presence of this elastic, pliable or deformable substrate can aid in the sealing of the fluidic element against the manifold (50). The elastic, pliable or deformable substrate can, for example, be a membrane, a gasket or a suitably shaped plug, and it may comprise, for example, silicone, SEBS, Viton, polypropylene, rubber, PTFE, etc. As illustrated, the elastic, pliable or deformable substrate can be held in place by capturing it with an additional component (e.g. a cover plate (63) in this example). However, the elastic, pliable or deformable substrate can also be retained in a variety of other ways, including for example by bonding, adhesion, welding, etc.

The desired function of the embodiments illustrated in FIGS. 9B, 11A and 11D are hereby illustrated by example: a pressure lid (11) of a perfusion manifold assembly (10) possessing a ridge around its instrument interface is brought into contact with the pressure manifold (50). As the lid is moved closer to the valve, the lid's ridge begins forming a pressure seal against the manifold's silicone membrane. With the lid's advance, the shuttle gradually moves up and at some point begins depressing the central pin or poppet (65) of the Schrader valve (59). However, according to the example, the shuttle would be designed such that a sufficiently good gas seal is formed before the valve's pin is depressed enough to open the Schrader valve (59). Once the valve open (and ideally not before) gas is able to flow between the manifold (50) and pressure lid (11). It is important to note that in this example, Schrader valves sense the presence of each pressure-lid ridge independently, rather than sensing the presence of a perfusion disposable (or pressure lid) as a single unit. Such embodiments may provide a further advantage in that they may accept different configurations of pressure lids or perfusion disposables, for example, a configuration that employs only 4 of the 5 illustrated ports.

FIG. 10A illustrates one embodiment of the PD engaging face (54) of a pressure manifold (50) that is a distribution manifold and shows elastomeric regions, which act as gaskets to improve gas seal against the fluidic element. In a current embodiment, a gas seal can be formed by compressing these elastomeric regions against ridges present on the top of pressure lids (11), which are in turn disposed onto perfusion disposables (10). The illustrated distribution manifold (50) can distribute to each of six pressure lids pressure (positive or negative) used for enact pressure-driven flow as well as pressure (positive or negative) used to actuate mechanical stretch within the included organ-on-chip devices (in this example, each of these is disposed within a perfusion disposable, which is in turn covered with a pressure lid). The illustrated distribution manifold includes several Schrader-like valves (see FIG. 11D).

As the manifold engages the PDs, the valve seals engage the sealing teeth or ridges on the top of the cover (see FIG. 2C) forming a seal for transferring pressurized gas from the manifold into the reservoir chambers. The poppet (65) (FIG. 11D) acts as a backing to provide a rigid surface for the sealing tooth on the cover to compress the valve seal. This provides load transfer from the cover to the Schrader valve (59) to actuate it when a PD is in position. Simultaneously, the Schrader Valve (or similar type valve system) is actuated by the engagement to the PD Cover to all gas flow from the pressure regulator into the PD. When no PD is in the respective position, the valve prevents any gas flow.

Figure 2A:
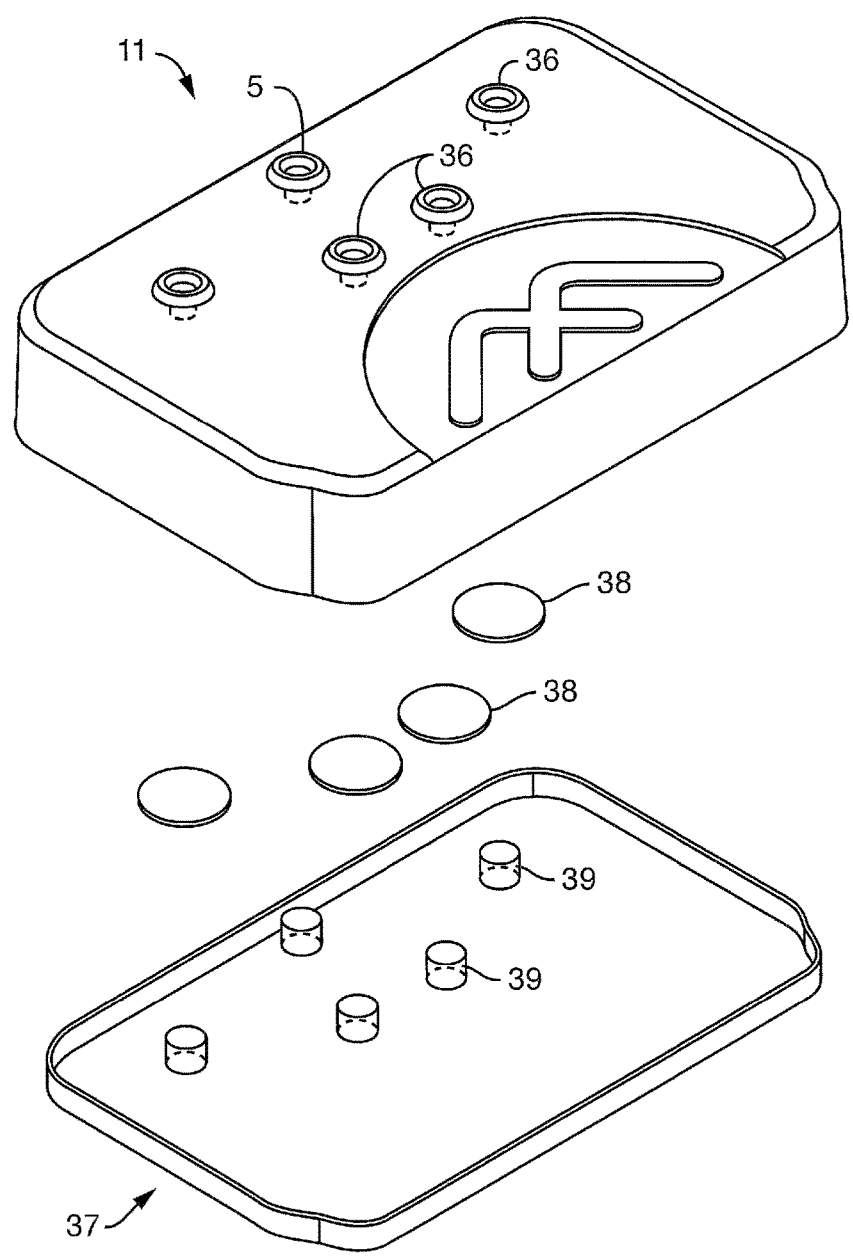
FIG. 2A is an exploded view of one embodiment of the cover assembly comprising a pressure cover or pressure lid. In the illustrated embodiment, the pressure lid comprises a plurality of ports (e.g. through-hole ports) associated with filters and corresponding holes in a gasket. The illustrated design of the holes in the gasket is intended to permit the gasket to aid in retaining the illustrated filters in position. In alternative embodiments, gasket openings may employ a shape different from openings in the lid. For example, the gasket can be shaped to follow the contour of one or more reservoirs with which it is intended to form a fluidic or pressure seal. In some embodiments, a plurality of gaskets may be employed. In some embodiments, the filters and/or gasket may be fixed using an adhesive, heat stacking, bonding (ultrasonic, solvent-assisted, laser welding), clamped, or captured by elements of the lid and/or an additional substrate. Although the illustrated pressure lid comprises through-hole ports, alternative embodiments comprise one or more channels that route at least one top-surface port to one or more bottom surface ports, which need not be directly underneath the top-surface port.
Figure 2B:
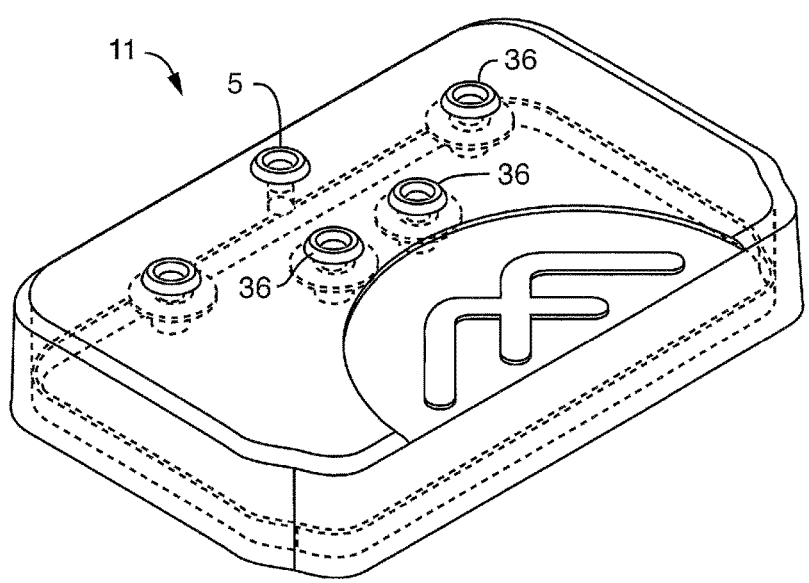
FIG. 2B shows the same embodiment of the cover assembly illustrated in FIG. 2A with the filters and gasket positioned within (and under) the cover.
Figures 1, 2C:
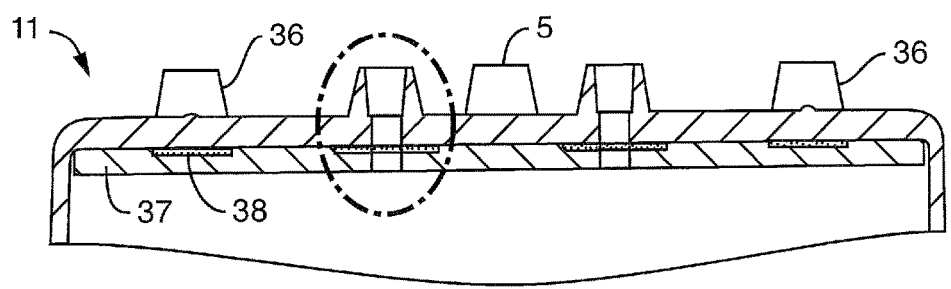
FIG. 2C-1 is a cross-section view of one embodiment of the cover assembly showing the ridges or sealing tooth that surrounds both the through-hole ports in the cover.
Figures 2, 2C:
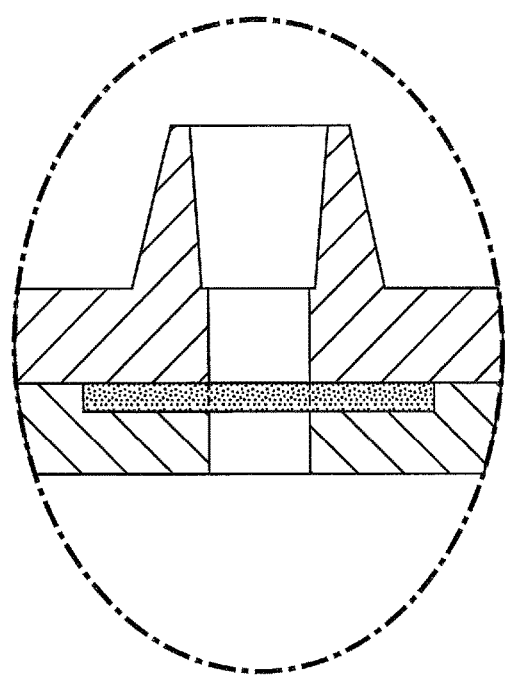
Figure 2D:
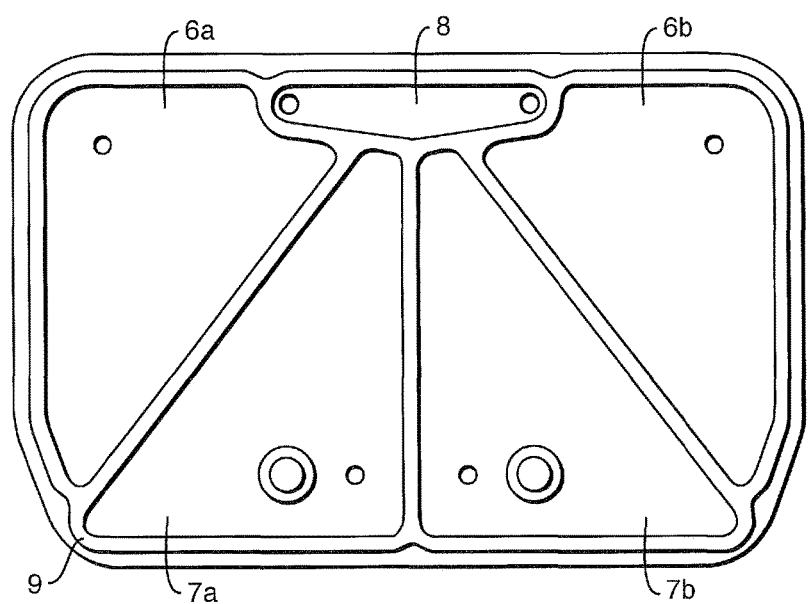
FIG. 2D is a top view of one embodiment of the reservoir chamber-cover assembly seal showing the sealing tooth, vacuum chamber and inlet and outlet chambers.
Figures 2, 2E:
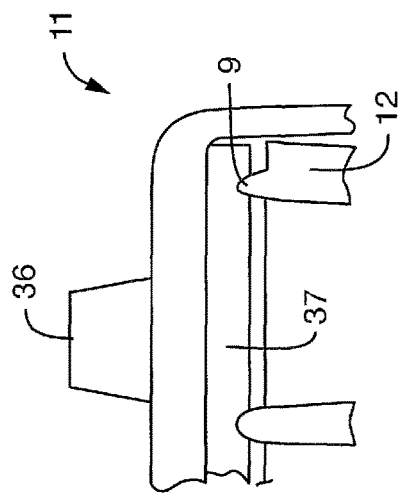
Figures 1, 2E:
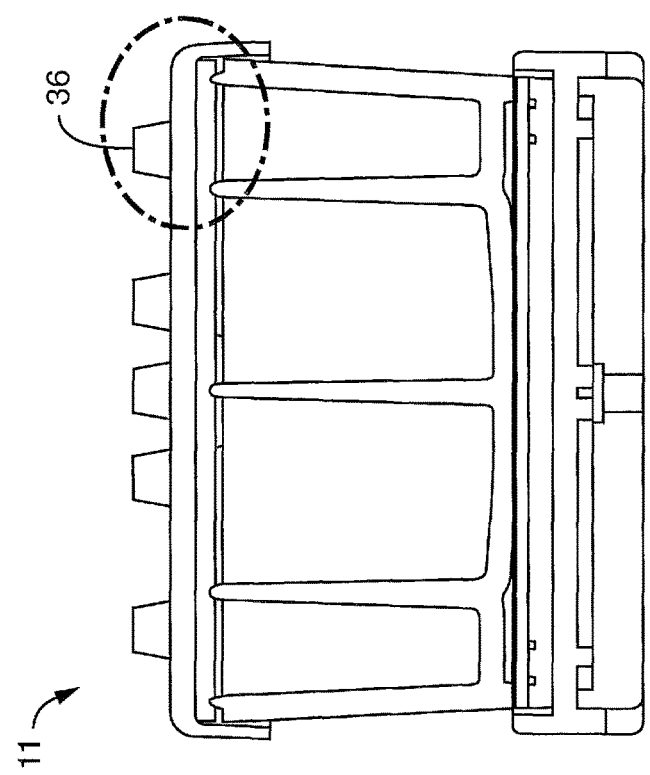

The spring shuttle (55) (FIG. 10B) provides the load to the cover assembly (11) to create the reservoir chamber-cover assembly seals (e.g. pressure lid-to-reservoir seals) (FIG. 2D). In operation, there is a deflection of the valve seal and the displacement of the poppet (65) when the PD is engaged.

Alternatively, a lid compressor (FIG. 10C) provides the load to the cover assembly to create the reservoir chamber-cover assembly seals (e.g. pressure lid-to-reservoir seals).

In one embodiment, each valve assembly has an optional spring, flexure or elastic component built in that allows for pressure to be applied to each seal independently. In one embodiment, the spring (or similar element) is an integral part of the valve function, but one can get additional function out of it by using it to apply pressure to the sealing tooth on the reservoir lid. The spring (or similar element) can work to restore the shuttle and to apply pressure against the fluidic element to provide or improve the gas seal. Independently applying this load to each sealing element on the lid results in a design that is more robust both to variations due to manufacturing tolerances, and how many PDs happen to be loaded into the instrument.

In some embodiments, one or more of the described valves are controlled by software or a user. For example, the user or software may aim to disconnect gas flow even if a fluidic element (e.g. perfusion disposable) is present at the corresponding interface. This could be desired, for example, if the user suspects or the software or sensor detects that there is excess gas flow to the fluidic element, perhaps because the element is damaged. The pressure manifold (whether a distribution manifold or not) may further include sensors, for example, pressure sensors, flow sensors, etc.

E. Controlling Pressure and Flow

In one embodiment, a flow rate of between 5 and 200 uL/hr, and more preferably between 10 and 60 uL/hr, is desired through the one or more microchannels of the device. In one embodiment, this flow rate is controlled by the applied gas pressure from the pressure manifold (described above). For example, when one applies between 0.5 and 1 kPa, this nominal pressure results, in one embodiment, in a flow rate of between 15 uL/hr and 30 uL/hr.

In addition to maintaining control over this gas pressure over time (and thereby maintain control over flow), in some embodiments, one must also address the gas pressure that may be applied by the process of engaging or disengaging the manifold against the perfusion disposable. That is to say, it is been observed, in a particular embodiment, that the step of engaging the manifold results in a pressure spike of as much as 100 kPa on the gas present within a reservoir included in the perfusion disposable. This can cause a spike in the flow rate and/or an undesired pressure on a coupled microfluidic device. In the particular case wherein the coupled microfluidic device comprises a membrane, an undesired pressure spike may deform the membrane, create trans-membrane flow and/or damage any included cells.

Without being bound by theory, the described pressure spikes can be caused because the mechanical force applied by the manifold to the pressure lid deforms one or more compliant materials included in the pressure lid or perfusion disposable (e.g. compressing any gaskets and the like). Such deformation can act to shrink the volume of gas present in the reservoir, increasing its pressure. The opposite effect leading to a negative spike in pressure may occur during manifold disengagement; one skilled in the art will appreciate that while this discussion primarily contemplates positive spikes that are typical to manifold engagement, analogous consideration may be given to negative pressure spikes that may be typical during manifold disengagement. Whether positive or negative, spikes can be particularly troublesome where the gas volume in the reservoir is low, which may occur when the volume of liquid in a reservoir is high (for example, in the preferred embodiment when more than 3 milliliters, and particularly when the volume is more than 5 milliliters). These engagement spikes may take time to dissipate, as the excess pressure must typically vent. In embodiments wherein the pressure lid includes a filter, this filter may provide the dominant resistance to the venting, dictating the dynamics of pressure-spike dissipation. In one embodiment, the present invention contemplates reducing the venting resistance in the system so as to avoid, reduce the magnitude and/or reduce the duration of such spikes. In on embodiment, the present invention contemplates selecting filters in order to mitigate the pressure spikes during cartridge insertion and removal.

In this regard, reference is made to FIG. 2. FIG. 2A is an exploded view of one embodiment of the cover assembly (11) comprising a cover or lid having a plurality of ports (e.g. through-hole ports) associated with filters (38) and corresponding holes (39) in a gasket. FIG. 2B shows the same embodiment of the cover assembly with the filters (38) and gasket positioned within (and under) the cover. In one embodiment, the filters for the outlet pressure ports are selected for low gas-flow resistance. For example, some embodiments employ 25 micron filters instead of 0.2 micron filters (used in the inlet pressure ports), in order to decrease resistance and cause the manifold-engagement related gas pressure (discussed above) to rapidly dissipate, avoiding a prolonged spike in the flow rate. In particular embodiments, filters with an average pore size of 25 um (commercially available from Porex, filter 4901) do not compromise sterility when ⅛ inch in thickness. These filters maintain sterility, despite their larger pore size (much larger than typical bacteria/spores), by creating a tortuous path through their thickness, which is significantly thicker than the previously mentioned filter membrane/sheets.

It is important to note that the design of inlet and outlet pressure ports may demand different treatment with regards to the venting resistance. For example, in embodiments wherein the perfusion disposable or microfluidic device comprise a resistor, pressure applied on the resistor side (whether the resister is placed upstream or downstream of a region of interest) typically does not act directly on the region of interest (which may, for example, include cells). This can be the case, for example, if liquid flow through the resistor generates a pressure drop. In contrast, pressure spikes on a side without the resistor (whether inlet or outlet) may act directly on the region of interest, as there may not be a sufficient pressure drop to provide some degree of insulation. In a particular example with a resistor on the inlet side of the region of interest, a pressure spike on the inlet may produce a corresponding spike in flow rate but minimal increase in the pressure experienced within the region of interest; in contrast, a pressure spike on the outlet may produce both a spike in flow rate and in experienced pressure. In some applications, for example where the microfluidic device includes a membrane, pressures in the regions of interest may be significantly more detrimental than a temporary spike in flow rate. Accordingly, in this example it may be advisable to include low-resistance filters only in the outlet ports and include more typical (higher resistance) filters in the inlet ports, as these can provide advantages in flow regulation (discussed further in the present disclosure).

Having discussed the engagement/disengagement spike issue, the issue of controlling gas pressure, particularly in low pressure ranges is now addressed. Some commercially available pressure regulators (or pressure controllers) advertise an addressable pressure range with a lower pressure limit that is greater than zero. For example the SMC ITV-0011 regulators are marketed for pressure control in the range of 1 to 100 kPa (it has been observed that their linearity is poor in the 0 to 1 kPa range). In some applications, it may be desirable to nevertheless attain flow rates that correspond to pressures below the commercially available regulator's specified or linear range. Moreover, the accuracy of commercially available pressure regulators is typically a percentage of "full range," implying that control at the low end of pressure is characterized by a larger percentage of variability. In some applications this can translate into low accuracy or fidelity in pressure control towards the lower end of the usable range. In one embodiment, either or both of these challenges are addressed by a form of "pulse width modulation" included in a method for pressure actuation.

In this regard, reference is made to FIG. 6. In one embodiment, the culture module (30) comprises a removable tray (32) for positioning the assembly-chip combinations, a pressure surface (33), and pressure controllers (34). In one embodiment, the tray (32) is positioned on the culture module (30) and the tray (32) is moved up via a tray mechanism (35) to engage the pressure surface (33) of the culture module, i.e. the cover or lid (11) of the perfusion manifold assembly engages the pressure surface of the culture module. Rather than having the pressure controllers "on" all of the time, they are switched "on" and "off" (or between two or more setpoints) in a pattern. Accordingly, the switching pattern may be selected such that the average value of pressure acting liquid in one or more reservoirs corresponds to a desired value. Such approaches are analogous to the techniques of pulse-width modulation (PWM), pulse-density modulation (PDM), delta-sigma modulation (DSM) and similar techniques that are known in the field of electrical engineering. In the case of pulse-width modulation, for example, a regular switching period is selected. Within each period the pressure regular may be turned on for a set pressure for a desired duration and turned off for the remainder of the switching period. The longer the switch is on compared to the off periods, the higher the total average pressure supplied. The term "duty cycle" describes the proportion of "on" time to switching period; a low duty cycle corresponds to low pressure, because the pressure is off for most of the time. Duty cycle is expressed in percent, 100% being fully "on." By using this type of "pulse width modulation" with the pressure controllers, it has been found that the average gas pressure can be reliably maintained below 1 kPa, using a regulator that does not offer linear control in that range. In a particular embodiment, the pressure regulator is used in its typical "linear" mode for pressure between 1 kPa and 100 kPa, and switched to pulse-width modulation using an "on pressure" of 2 kPa and an "off pressure" of 0 kPa for average-pressure setpoints between 0 kPa and 1 kPa. In other examples, pulse-width, pulse-density or delta-sigma modulation may be used for controlling the average pressure between 0.3 and 0.8 kPa.

Although the disclosed method can involve applying a pulsatile pressure pattern to the pressure lid, it has been empirically found that the filters aid in smoothing the pressure incident on the liquid with the reservoir. Without being bound by theory, the degree of smoothing increases with the resistance of the filter to gas flow and with the volume of gas within the reservoir (which typically decreases the more liquid is present). Similarly, analogy to electrical circuits indicates that smoothing increases with shorter switching periods. Accordingly, one skilled in the art may select a degree of smoothing by selecting the resistance of the gas filter, setting a lower bound on the gas volume, and selecting a switching period or modulation pattern. It is important to ensure that the pressure regulator is able to controllably regulate pressure at a sufficient rate to reproduce the designed pressure modulation pattern. In some embodiments, 0.2 um filters (Porex filter membrane) and a switching period of 10 seconds provide desired smoothing. In other embodiments, 0.4 um filters may be used.

DETAILED DESCRIPTION OF THE PREFERRED EMBODIMENTS

A. Drop-to-Drop Connections

Figure 14A:
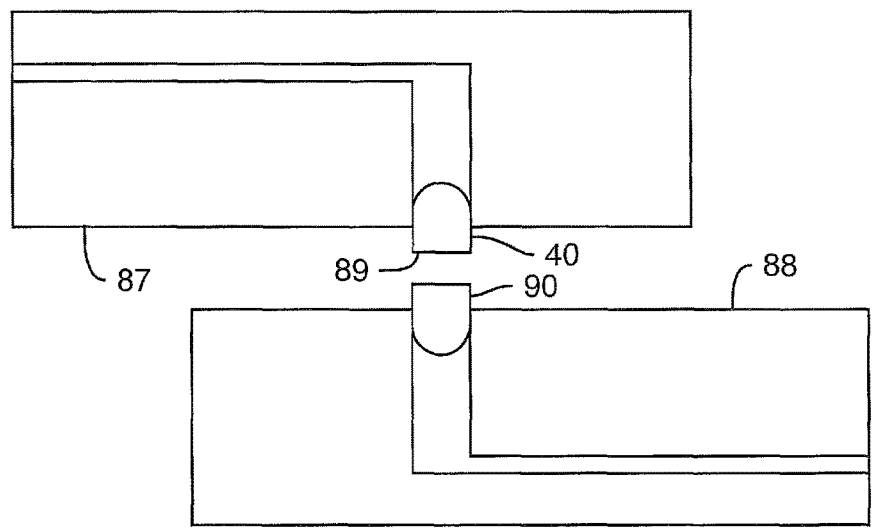
FIG. 14A shows two fluidically primed devices (the fluid is shown with a meniscus) with ports and microchannels that are not yet connected.
Figure 14B:
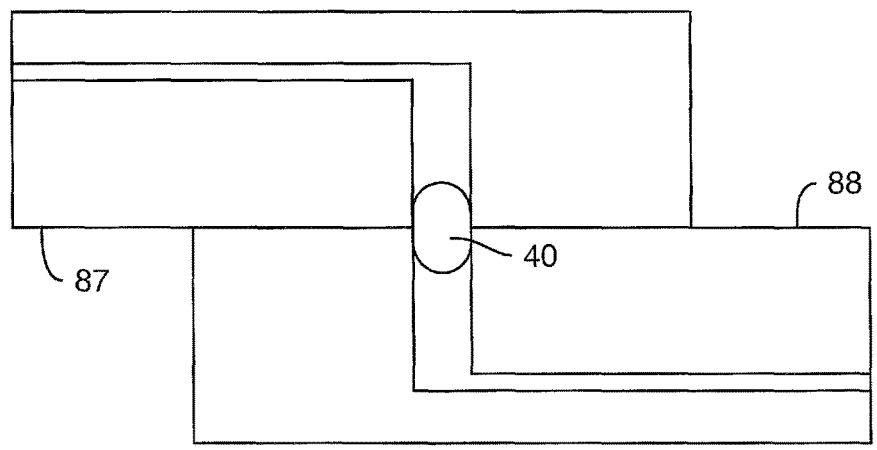
FIG. 14B shows the devices of FIG. 14A contacting in a manner that results in the introduction of air bubbles (air is shown in the middle, between each meniscus) into the ports (and ultimately, the microchannels).

A drop-to-drop connection scheme is contemplated as one embodiment for putting a microfluidic device in fluidic communication with another microfluidic device, including but not limited to, putting a microfluidic device in fluidic communication with the perfusion manifold assembly. Putting devices in fluidic communication with each other can result in the formation of bubbles (40), as shown in FIGS. 14A and 14B, where a first surface (87) comprising a first fluidic port (89) is aligned with a second surface (88) and a second fluidic port (90). In one embodiment, a drop-to-drop connection is used to reduce the chance of bubbles becoming trapped during connection. Air bubbles are particularly challenging in microfluidic geometries because they get pinned to surfaces and are hard to flush away with just fluid flow. They pose additional challenges in cell culture devices because they can damage cells through various means.

In one embodiment, droplets are formed on the surfaces of the devices in the areas around and on top of the fluidic vias or ports as shown in FIGS. 15A, 16A, 16B, 16D and 17-21. When the surfaces come near each other during a connection, the droplet surfaces join without introducing any air bubbles. In practice, maintaining alignment and stability of the droplets during manual device manipulation is challenging. Additionally, in situations where the Bond number is high liquid tends to drain from devices quickly and in an unstable manner. A number of solutions are herein described to address the problems of both maintaining a stable droplet on a device surface and guiding the drop-to-drop engagement of two primed devices in a controlled and robust manner.

Figure 16A:
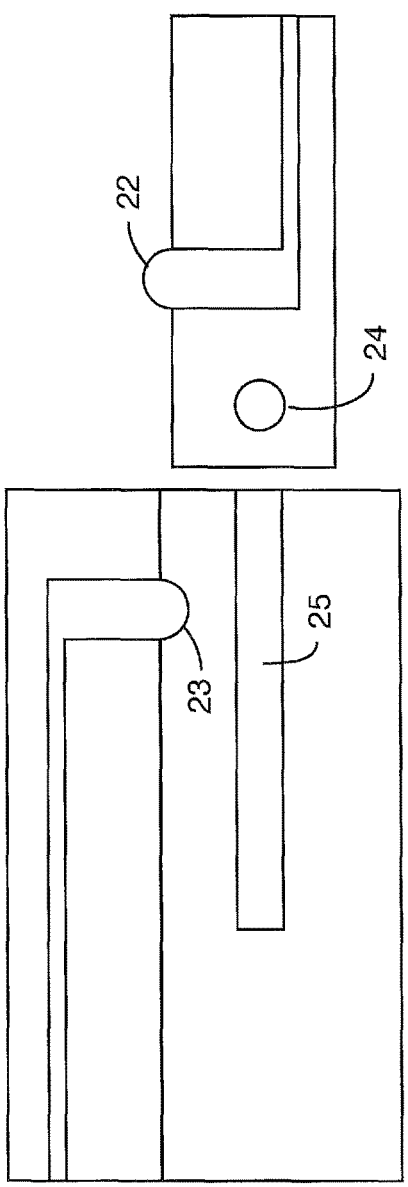
FIG. 16A shows one embodiment for bringing a microfluidic device into contact with a fluid source or another microfluidic device, wherein the microfluidic device approaches from the side.
Figure 16B:
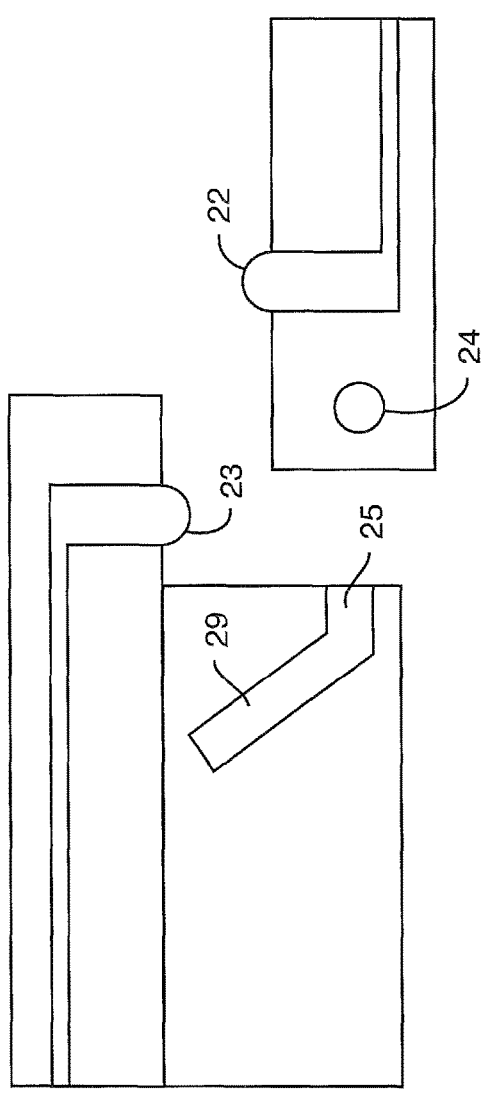
FIG. 16B shows one embodiment for bringing a microfluidic device into contact with a fluid source or another microfluidic device, wherein the microfluidic device approaches from the side and underneath, so as to cause a drop-to-drop connection establishing fluidic communication (FIG. 16C).
Figure 16C:
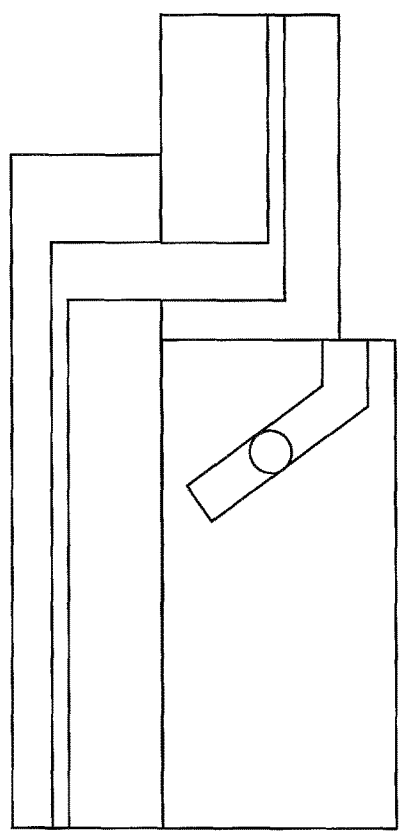
FIG. 16D shows yet another approach for brings a microfluidic device into contact with a fluid source or another microfluidic device, wherein the microfluidic device pivots.
Figure 16D:
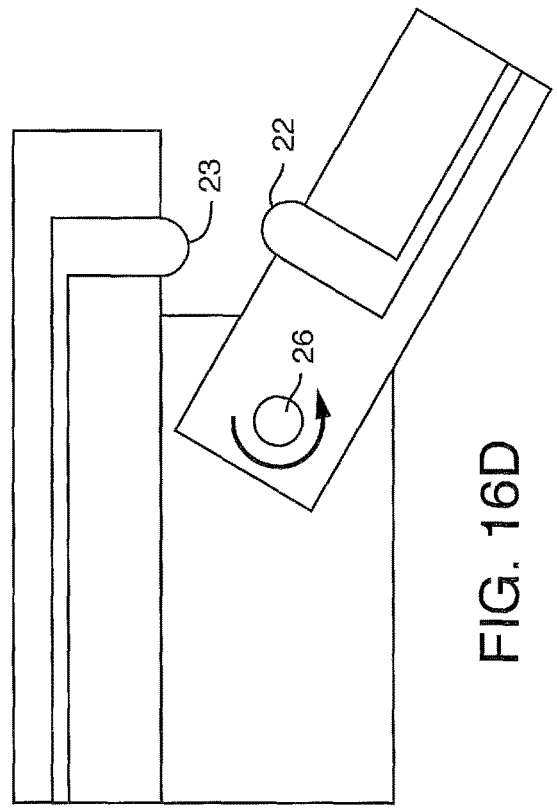

FIG. 16A shows one embodiment for bringing a microfluidic device into contact with a fluid source or another microfluidic device, wherein the microfluidic device approaches from the side so as to engage a side track with a portion configured to fit into said side track. FIG. 16B shows one embodiment for bringing a microfluidic device into contact with a fluid source or another microfluidic device, wherein the microfluidic device approaches from the side and underneath so as to engage a side track with a portion configured to fit into said side track, the side track comprising an initial linear portion and a subsequent angled portion, resulting in both a sideways and upward movement of the microfluidic device when engaging and traversing the side track, so as to cause a drop-to-drop connection establishing fluidic communication (FIG. 16C). FIG. 16D shows yet another approach for bringing a microfluidic device into contact with a fluid source or another microfluidic device, wherein the microfluidic device pivots on a hinge, joint, socket or other pivot point on the fluid source or other microfluidic device (with an arrow showing the general direction of movement).

Figure 17:
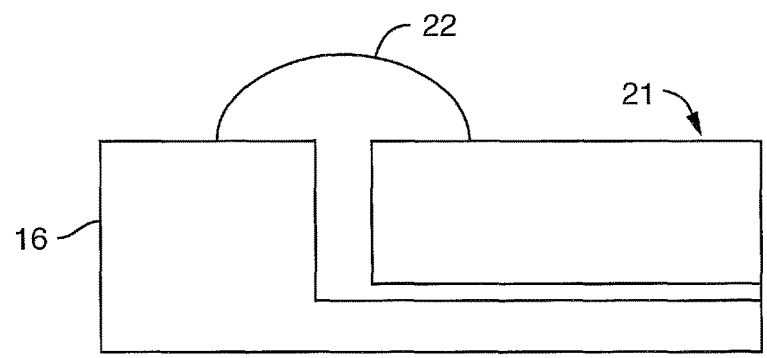
FIG. 17 is a schematic showing a confined droplet (22) on the surface (21) of a microfluidic device (16) in the via or port.

FIG. 17 is a schematic showing a confined droplet (22) on the surface (21) of a microfluidic device (16) in the via or port, wherein the droplet covers the mouth of the port and protrudes above the port, and where the port is in fluidic communication with a microchannel.

Figure 18:
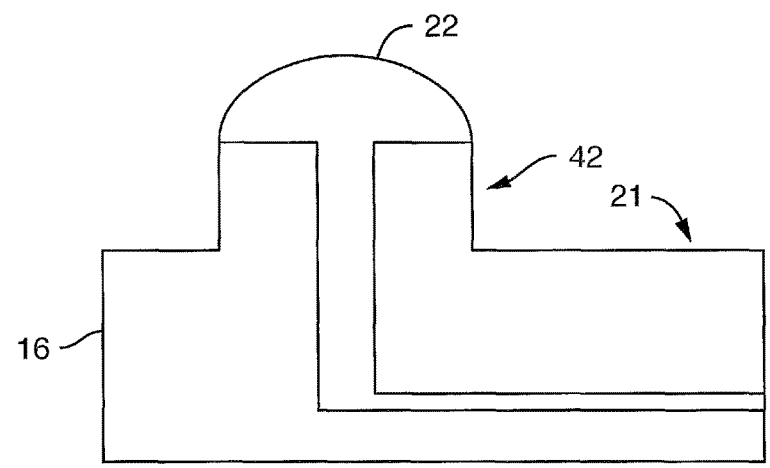
FIG. 18 is a schematic showing a confined droplet (22) above the surface (21) of a microfluidic device (16) in the area of the via or port, wherein the droplet sits on a molded-in pedestal or mount (42) and covers the mouth of the port and protrudes above the port, and where the port is in fluidic communication with a microchannel.

FIG. 18 is a schematic showing a confined droplet (22) above the surface (21) of a microfluidic device (16) in the area of the via or port, wherein the droplet sits on a molded-in pedestal or mount (42) and covers the mouth of the port and protrudes above the port, and where the port is in fluidic communication with a microchannel.

Figure 19:
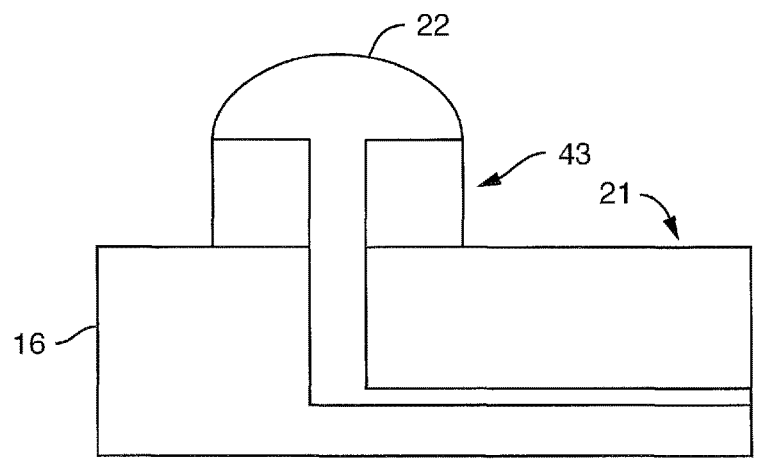
FIG. 19 is a schematic showing a confined droplet (22) above the surface (21) of a microfluidic device (16) in the area of the via or port, wherein the droplet sits on a gasket (43), covers the mouth of the port, and protrudes above the port, and where the port is in fluidic communication with a microchannel.

FIG. 19 is a schematic showing a confined droplet (22) above the surface (21) of a microfluidic device (16) in the area of the via or port, wherein the droplet sits on a gasket (43), covers the mouth of the port, and protrudes above the port, and where the port is in fluidic communication with a microchannel.

Figure 20:
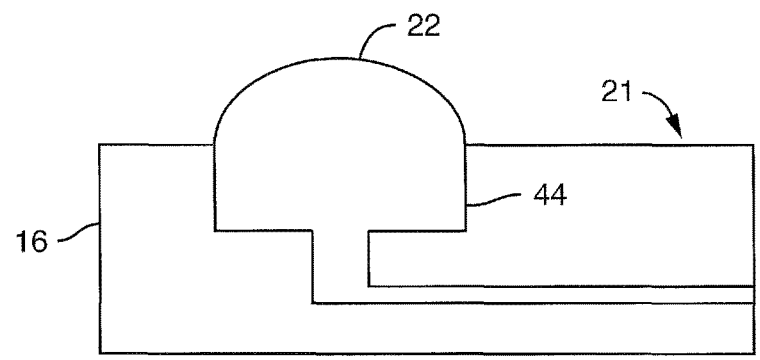
FIG. 20 is a schematic showing a confined droplet (22), a portion of the droplet positioned below the surface (21) of a microfluidic device (16) in the area of the via or port, wherein the droplet sits on a molded-in depression or recess (44) and covers the mouth of the port, with a portion protruding above the surface, and where the port is in fluidic communication with a microchannel.

FIG. 20 is a schematic showing a confined droplet (22), a portion of the droplet positioned below the surface (21) of a microfluidic device (16) in the area of the via or port, wherein the droplet sits on a molded-in depression or recess (44) and covers the mouth of the port, with a portion protruding above the surface, and where the port is in fluidic communication with a microchannel.

Figure 21:
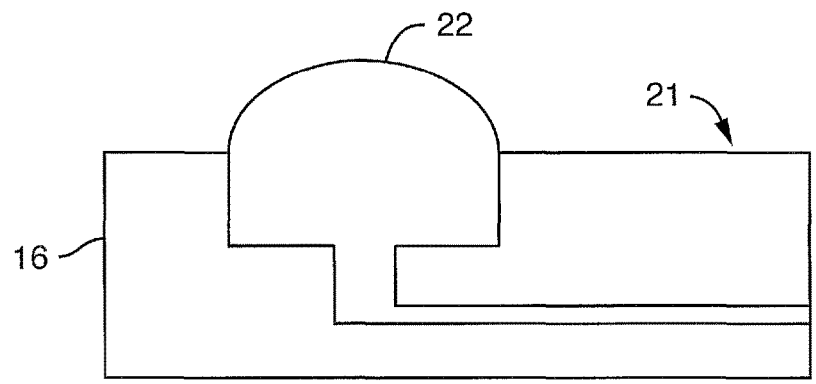
FIG. 21 is a schematic showing a confined droplet (22), a portion of the droplet positioned below the surface (21) of a microfluidic device (16) in the area of the via or port, wherein the droplet sits in a surrounding gasket and covers the mouth of the port, with a portion protruding above the gasket.

FIG. 21 is a schematic showing a confined droplet (22), a portion of the droplet positioned below the surface (21) of a microfluidic device (16) in the area of the via or port, wherein the droplet sits in a surrounding gasket and covers the mouth of the port, with a portion protruding above the gasket.

Figure 22A:
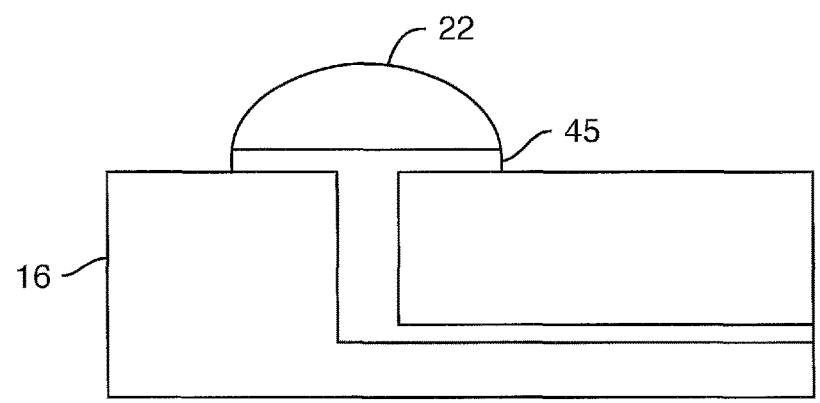
FIG. 22A employs a hydrophilic adhesive layer or sticker (45) upon which the droplet (22) spreads out to the edges of the sticker, constrained by a surrounding hydrophobic surface.
Figure 22B:
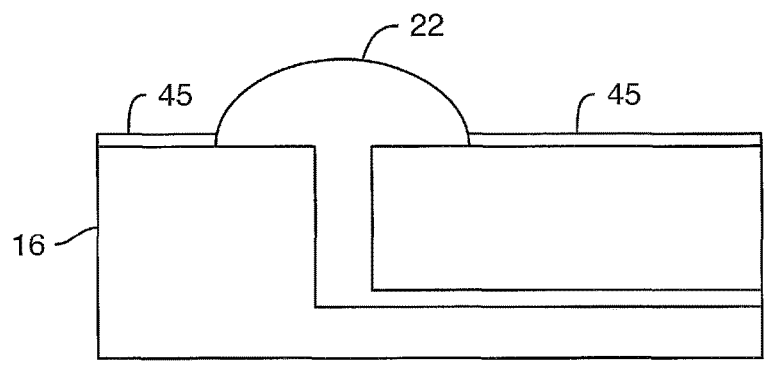
FIG. 22B shows a droplet (22) spreading out on a hydrophilic surface of the device, constrained by a surrounding hydrophobic surface.

FIG. 22 is a schematic showing a surface modification embodiment employing stickers for confining droplets on the surface of a microfluidic device (16) at a port, and where the port is in fluidic communication with a microchannel. FIG. 22A employs a hydrophilic adhesive layer or sticker (45) upon which the droplet (22) spreads out to the edges of the sticker, constrained by a surrounding hydrophobic surface. FIG. 22B shows a droplet (22) spreading out on a hydrophilic surface of the device, constrained by a surrounding hydrophobic surface (45) created by one or more adhesive layers or stickers on each side of the port, and where the port is in fluidic communication with a microchannel.

Figure 23:
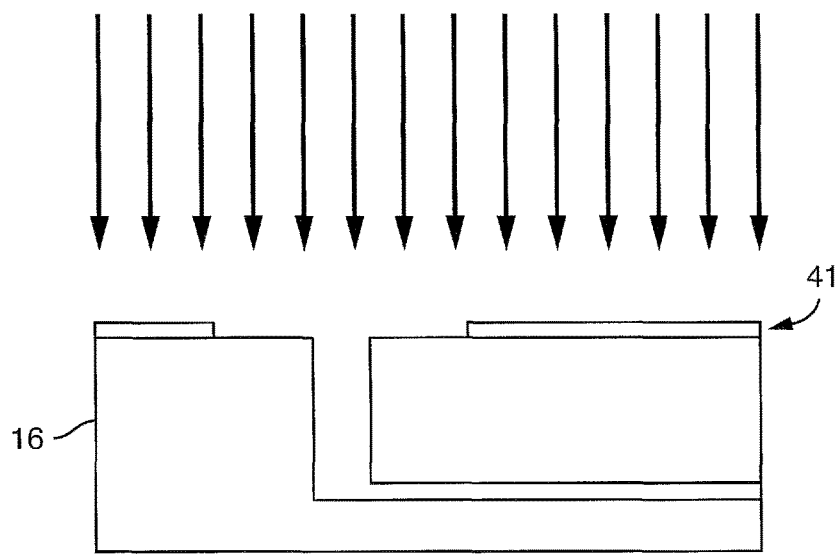
FIG. 23 is a schematic showing a surface modification embodiment employing surface treatment (indicated by downward projecting arrows) in conjunction with a mask (41).

FIG. 23 is a schematic showing a surface modification embodiment employing surface treatment (e.g. chemical vapor deposition, plasma oxidation, Corona, etc.—indicated by downward projecting arrows) in conjunction with a mask (41); in one embodiment, the microfluidic device (16) is made of a naturally hydrophobic material which becomes hydrophilic upon such surface treatment where there is no mask, but remains hydrophobic where there is a mask. After the surface treatment, the mask can be removed and the channel can be filled with fluid so as to generate a droplet protruding above the surface, but constrained by the regions that remained hydrophobic (see FIG. 17).

FIG. 24 is a schematic of one embodiment of a drop-to-drop connection scheme whereby a combination of geometric shapes and surface treatments are used to control the droplet. FIG. 24A shows an embodiment of the microfluidic device or "chip" comprising a fluid channel and ports, having an elevated region at each port (e.g. a pedestal or gasket). When other portions of the device (i.e. portions other than the pedestal or gasket) are treated (e.g. plasma treatment) to make them hydrophilic, the naturally hydrophobic pedestal or gasket can be protected with a mask (shown in FIG. 24A on top of the pedestal or gasket as element 41) during plasma treatment to keep it from becoming hydrophilic. After plasma treatment, the mask is removed (e.g. peeled off the surface of the pedestal or gasket). FIG. 24B shows the hydrophilic channel filled with fluid where the droplet radius is balanced at each end (i.e. at the port openings); the droplet (22) is constrained by the hydrophobic gasket surface. FIG. 24C shows one portion of the microfluidic device of FIG. 24B with an upward projecting droplet (22) approaching (but not yet in contact with) one portion of the mating surface of the perfusion manifold assembly, which also has a projecting droplet (in this case, the droplet (23) is projecting downward). FIG. 24D shows the same portion of the microfluidic device of FIG. 24C with the upward projecting droplet (22) of the microfluidic device making contact with (and merging with) the downwardly projecting droplet (23) of the perfusion manifold assembly. The droplets coalesce in a controlled manner when they are on hydrophilic surfaces but constrained by hydrophobic surfaces. As noted previously, embodiments where the microfluidic device approaches from above (with a downwardly projecting droplet) the perfusion manifold assembly (with an upwardly projecting droplet) are also contemplated.

Figure 25A:
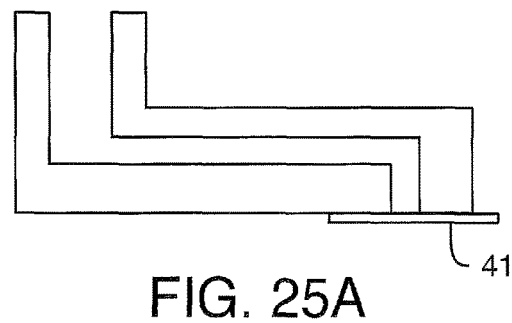
FIG. 25A shows an embodiment of the perfusion manifold assembly comprising a fluid channel and a port.
Figure 25B:
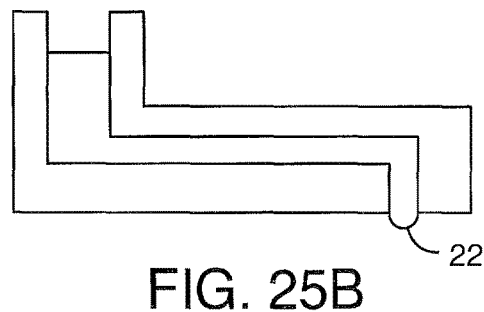
FIG. 25B shows the hydrophilic channel filled with fluid to a level (e.g. height of the column of fluid).

FIG. 25 shows an embodiment of drop-to-drop connecting using surface treatments alone (i.e. without geometric shapes such as pedestals or gaskets). FIG. 25A shows an embodiment of the perfusion manifold assembly comprising a fluid channel and a port. When other portions of the naturally hydrophobic mating surface (i.e. portions other than the region around the port) are treated (e.g. plasma treatment) to make them hydrophilic, the region around the port protected with a mask (shown in FIG. 25A as element 41 covering the port and a small region of the mating surface around the port) during plasma treatment to keep it from becoming hydrophilic. After plasma treatment, the mask is removed (e.g. peeled off the mating surface around the port). FIG. 25B shows the hydrophilic channel filled with fluid to a level (e.g. height of the column of fluid). In some embodiments, the formed droplet is able to resist the pressure (gravitational head) exerted by the fluid volume. This is advantageous, as it can enable drop-to-drop connection while minimizing the dripping of the top droplet and stabilizing its size. Without being bound by theory, the drop resists the exerted pressure of the fluid volume because that pressure is balanced out by the surface tension of the droplet; this surface tension is determined in part by the droplet radius, which in turn can be controlled using designs and methods disclosed herein; for example, when the droplet is constrained by the hydrophobic region around the port, the radius of its surface is similarly constrained.

Figure 26:
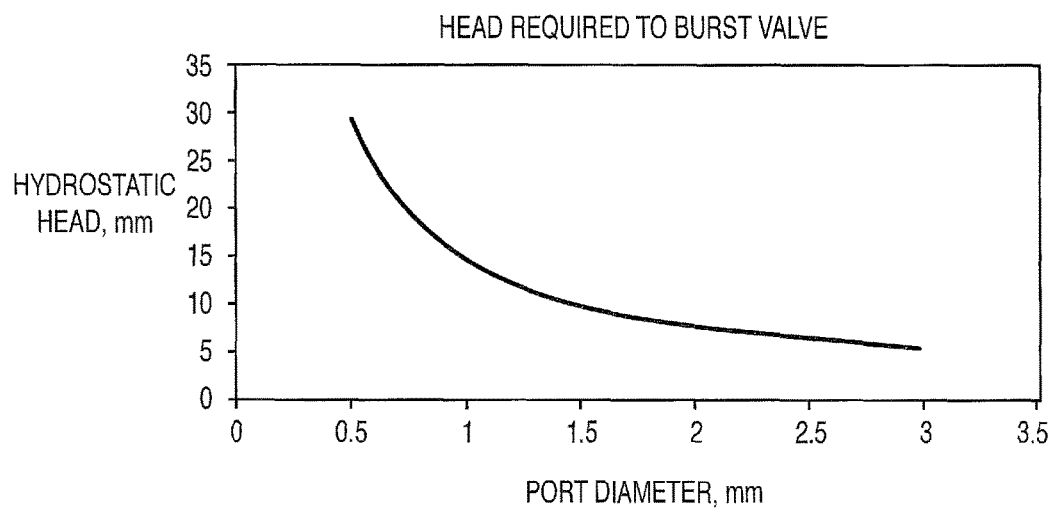
FIG. 26 is a chart showing (without being bound by theory) the relationship between the port diameter (in millimeters) and the maximum hydrostatic head (in millimeters) that the stabilized droplet can support.

FIG. 26 is a chart showing (without being bound by theory) the relationship between the port diameter (in millimeters) and the maximum hydrostatic head (in millimeters) that the stabilized droplet can support, assuming that the fluid has the same surface tension as water (the model does not include the reservoir meniscus). This shows that one can work with a variety of port diameters, selecting those that can support substantial volumes of the water column in the channel (and in general support substantial back pressures), thereby providing a significant process window and tolerance for user manipulation. In yet another embodiment, by adjusting the pressure on the fluid, a projecting or protruding droplet of a desired size is achieved.

It is not intended that the present invention be limited to a particular method for controlling the droplet size, orientation, or direction. In one embodiment, the present invention contemplates using (or making) engineered surfaces to form stable drops. Such surfaces can be inherently hydrophilic or hydrophobic, or can be treated to be hydrophilic or hydrophobic. It is not intended that the present invention be limited to any one technique. However, among the various methods of hydrophilic treatment (e.g. low-pressure oxygen plasma treatment, corona treatment, etc.), a cleaner technology is preferred to treat Poly(dimethylsiloxane) (PDMS) microfluidic devices. In one embodiment, the present invention contemplates using atmospheric RF plasma, so that hydrophilic surfaces can be created (on what is normally hydrophobic material). See Hong et al., "Hydrophilic Surface Modification of PDMS Using Atmospheric RF Plasma," *Journal of Physics: Conference Series* 34 (2006) 656-661 (Institute of Physics Publishing). In one embodiment, masks (41) are used together with such plasma treatments, as shown in FIG. 23. For example, a mask can be adhered to regions of the surface (e.g. made of PDMS or other polymer) of the microfluidic device (16) prior to plasma treatment in order to prevent such regions from becoming hydrophilic (and thereby controlling what part of the PDMS chip become hydrophilic and what portions remain hydrophobic). After plasma treatment, the mask (41) can be removed (FIG. 24) (typically by simply peeling the mask off the surface). In yet another embodiment, the present invention contemplates the use of plasma surface treatment in a fluorinated environment to increase the hydrophobicity of the surface. See Avram et al., "Plasma Surface Modification for Selective Hydrophobic Control," *Romanian J. Information Science and Technology*, Vol. 11, Number 4, 2008, 409-422.

Alternatively, such surfaces can have geometric features or shapes that cause the droplet to form or behave in a desired manner. For example, a mating surface might have a projection, platform or pedestal (42) with a geometry that allows for a droplet of particular dimensions, as shown in FIG. 18. A surface might also be topped with a structure surrounding the port from which the droplet projects, such as a gasket (43) or other mechanical seal, as shown in FIG. 19, which fills the space between the two mating surfaces (i.e. one surface from the microfluidic device and one from the perfusion assembly), to prevent leakage while under compression.

Alternatively (FIG. 20), a portion of the droplet can be positioned in a depression or recess (44), such that a portion of the droplet is below the mating surface (21) of the microfluidic device, as shown in FIG. 20 and FIG. 21. In still another embodiment, adhesive patches or stickers (45) can be placed on the surface to create hydrophilic or hydrophobic regions on the mating surface of the microfluidic device, as shown in FIGS. 22A and 22B.

In yet another embodiment, a combination of geometric features and surface treatments can be applied. For example, a hydrophobic pedestal or gasket might be used (or made) to permit smaller droplet sizes. Most elastomeric polymers used to make gaskets are hydrophobic. Such gaskets are commercially available, e.g. from Stockwell Elastomerics, Inc. (Philadelphia Pa., USA). On the other hand, M&P Sealing machines high-quality products made from materials such as Polytetrafluoroethylene ("PTFE"), Perfluorolkoxy ("PFA"), or fluorinated Ethylene ("FEP"), including soft hydrophobic gaskets (Orange, Tex., USA). These are also contemplated in some embodiments. When other portions of the device (i.e. portions other than the pedestal or gasket) are treated (e.g. plasma treatment) to make them hydrophilic, a naturally hydrophobic pedestal or gasket can be protected with a mask during plasma treatment to keep it from becoming hydrophilic.

In one embodiment, the walls of the port (or at least a portion thereof leading up to the mating surface of the microfluidic device) are hydrophilic or made hydrophilic. In one embodiment, the walls of the corresponding port (or at least a portion thereof leading up to the mating surface of the perfusion assembly) are hydrophilic or made hydrophilic. In one embodiment, both the walls of the port of the microfluidic device and the corresponding port of the perfusion assembly (or portions thereof) are hydrophilic or made hydrophilic.

In one embodiment, the present invention contemplates that the surface is designed to retain a droplet that resists the weight of liquid in the reservoir (as shown in FIG. 25). This is especially important in practice, since it allows the droplets that go on the top device (i.e. where a first device approaches a second device from above) to be easily created. This embodiment allows one to simply put a measured amount of liquid into the reservoir (e.g. 100 uL, 75 uL, 50 uL or some other amount), leading that liquid to flow to the port, form a droplet and stop on its own. Importantly, it is not intended that this embodiment be limited to any particular amount of liquid; indeed, one does not need a precisely measured amount of liquid. It is sufficient to aim for a certain amount, as long as that amount is below a certain threshold (where the weight of the water overwhelms the droplet's surface tension and breaks through) in order to form a droplet by this method. It might be more or less convex depending on how much liquid is pushing down on it, but the spatial extent of the droplet should be the same.

It is not intended that the present invention be limited to only one manner for drop-to-drop connecting of microfluidic devices. In one embodiment, a first microfluidic device, such as an organ on a chip microfluidic device comprising cells that mimic one or more functions of cells in an organ in the body (i.e. mimic one or more functions of cells in an organ in the body such as cell-cell interaction, cytokine expression, etc.), has a droplet projecting upward, while the corresponding droplet on a second microfluidic device projects downward, as shown in FIG. 15A. In another embodiment, the first microfluidic device, such as an organ on a chip microfluidic device comprising cells that mimic cells in an organ in the body or at least one function of an organ, has a droplet projecting downward, while the corresponding droplet on the second microfluidic device projects upward.

Gravity alone, aside from momentum arguments, also plays a role in stable droplet formation. For example, a chip that is laid flat on a table does not experience significant forces due to gravity. If that device is tipped, as part of the engagement procedure for example, fluid will flow from the higher to lower point. Therefore, orientation of the device might be considered another way to aide in the confinement of droplets, including which device has vias pointing upwards vs downwards.

An additional aspect of controlling droplet volume is the fluidic resistance of the device channels. If a device has small channels, for example, the fluidic resistance might be high enough to maintain a nearly constant droplet volume over time despite there being forces driving fluid flow out of the device (e.g. gravity or capillary force). This is true even in the case of high Bond number. Tuning fluidic resistance might be utilized as a singular method to "confine droplets" or in combination with other methods like controlling liquid pinning geometry or controlling the wetting properties of the surfaces; fluidic resistance would be used to control droplet volume, while controlling the wetting properties of the surface would help control droplet placement.

B. Microfluidic Devices

It is not intended that the present invention be limited by the nature of the microfluidic device. However, preferred microfluidic devices are described in U.S. Pat. No. 8,647,861, hereby incorporated by reference, and they are microfluidic "organ-on-chip" devices comprising living cells in microchannels, e.g. cells on membranes in microchannels exposed to culture fluid at a flow rate. The surfaces of the microchannels and/or the membrane can be coated with cell adhesive molecules to support the attachment of cells and promote their organization into tissues. Where a membrane is used, tissues can form on either the upper surface, the lower surface or both. In one embodiment, different cells are living on the upper and lower surfaces, thereby creating one or more tissue-tissue interfaces separated by the membrane. The membrane may be porous, flexible, elastic, or a combination thereof with pores large enough to only permit exchange of gases and small chemicals, or large enough to permit migration and transchannel passage of large proteins, as well as whole living cells. In one embodiment, the membrane can selectively expand and retract in response to pressure or mechanical forces, thereby further physiologically simulating the mechanical force of a living tissue-tissue interface.

Figure 33A:
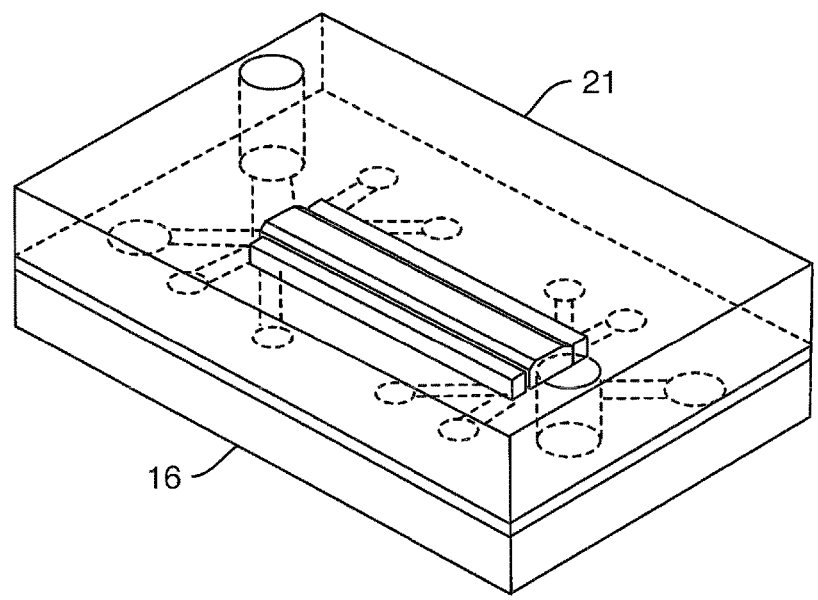
FIG. 33 shows a schematic of an illustrative microfluidic device or "organ-on-chip" device. The assembled device is schematically shown in FIG. 33A.
FIG. 33B shows an exploded view of the device of FIG. 33A.
Figure 33B:
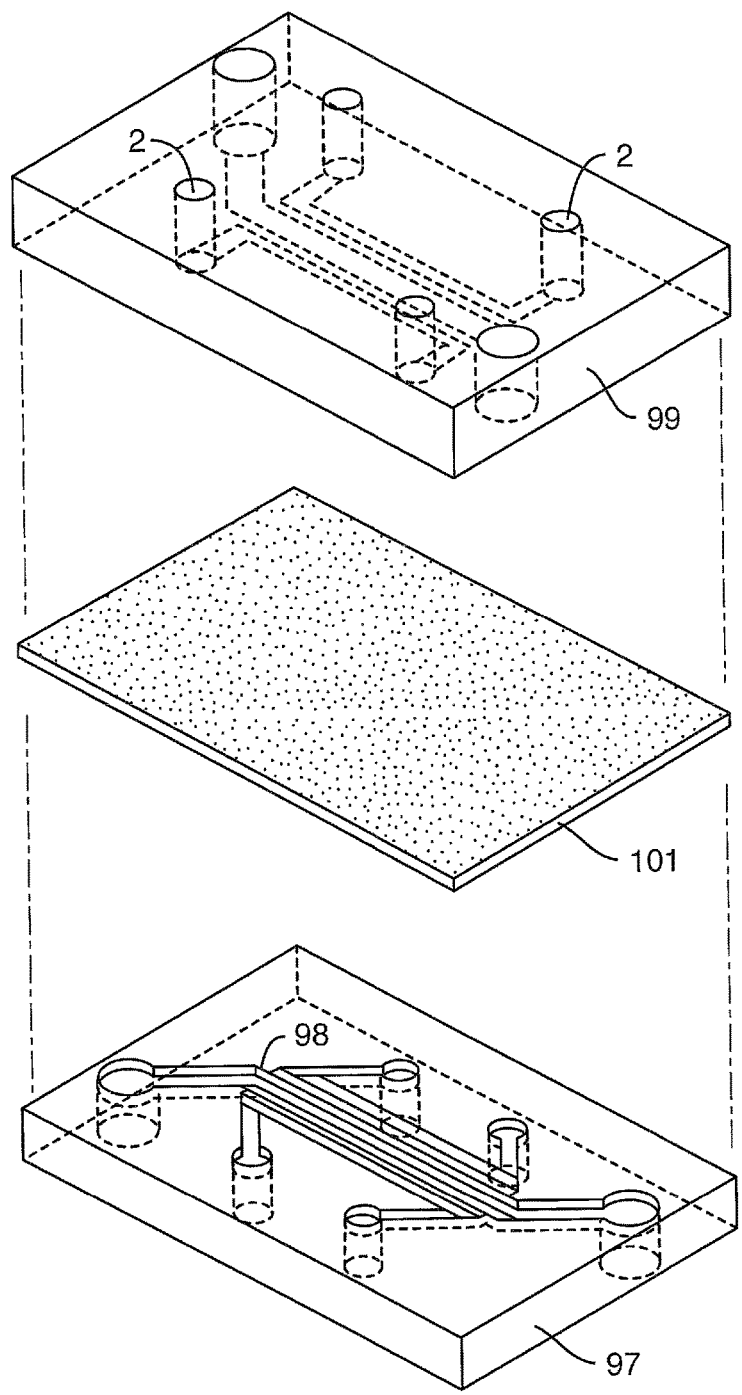

FIG. 33 shows a schematic of an illustrative microfluidic device or "organ-on-chip" device. The assembled device is schematically shown in FIG. 33A, which includes a plurality of ports. FIG. 33B shows an exploded view of the device of FIG. 33A, showing a bottom piece (97) having channels (98) in a parallel configuration, and a top piece (99) with a plurality of ports (2), with a tissue-tissue interface simulation region comprising a membrane (101) between the top (99) and bottom (97) pieces, where cell behavior and/or passage of gases, chemicals, molecules, particulates and cells are monitored. In an embodiment, an inlet fluid port and an outlet fluid port are in communication with the first central microchannel such that fluid can dynamically travel from the inlet fluid port to the outlet fluid port via the first central microchannel, independently of the second central microchannel. It is also contemplated that the fluid passing between the inlet and outlet fluid ports may be shared between the central microchannels. In either embodiment, characteristics of the fluid flow, such as flow rate and the like, passing through the first central microchannel is controllable independently of fluid flow characteristics through the second central microchannel and vice versa.

Figure 34:
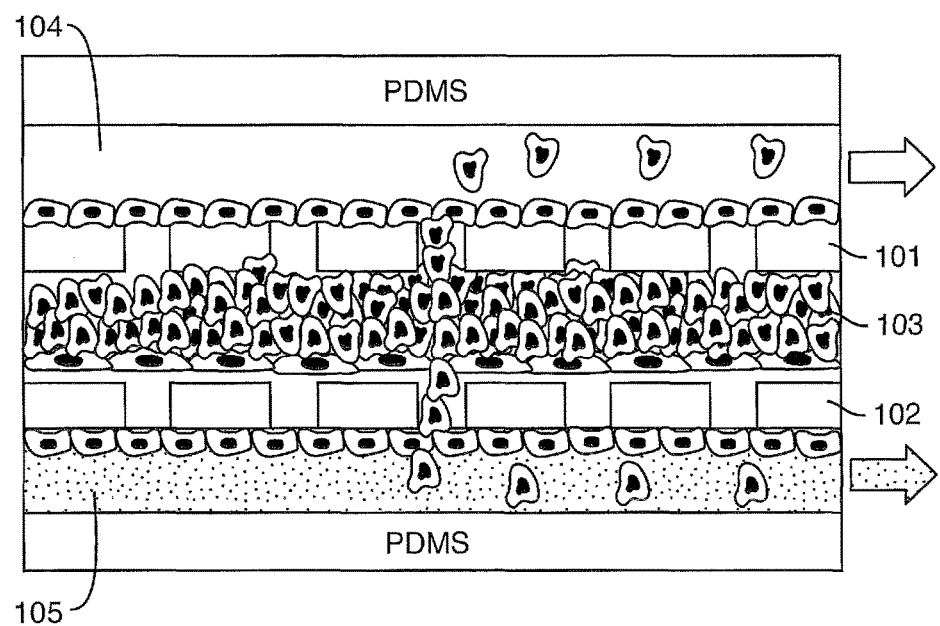
FIG. 34 is a schematic showing an embodiment with two membranes.

FIG. 34 is a schematic showing an embodiment with two membranes (101 and 102) with cells (103) inside the device in a first channel, but also in contact with fluid channels (104 and 105) with arrows showing the direction of flow. This three channel device allows one to follow the migration or movement of cells, e.g. lymphoid cells, vascular cells, nerve cells, etc. In one embodiment, membrane 101 is coated with a lymphatic endothelium on its upper surface and with stromal cells on its lower surface, and stromal cells are also coated on the upper surface of the second porous membrane 102 and a vascular endothelium on its bottom surface. The movement of these vascular and stromal cells can be monitored. Alternatively, a third type of cell can be placed in the middle (103) and the migration through the membranes can be monitored (e.g. by imaging or by detection of cells in the channels or channel fluid). The membranes may be porous or have grooves to allow cells to pass through the membranes.

In one embodiment this three channel device is used to determine cell behavior of cancer cells. Tumor cells are placed, for example, in the central microchannel surrounded on top and bottom by layers of stromal cells on the surfaces of the upper and lower membranes. Fluid such as cell culture medium or blood enters the vascular channel. Fluid such as cell culture medium or lymph enters the lymphatic channel. This configuration allows researchers to mimic and study tumor growth and invasion into blood and lymphatic vessels during cancer metastasis. The membranes may be porous or have grooves to allow cells to pass through the membranes.

C. Seeding Devices with Cells

Figure 35A:
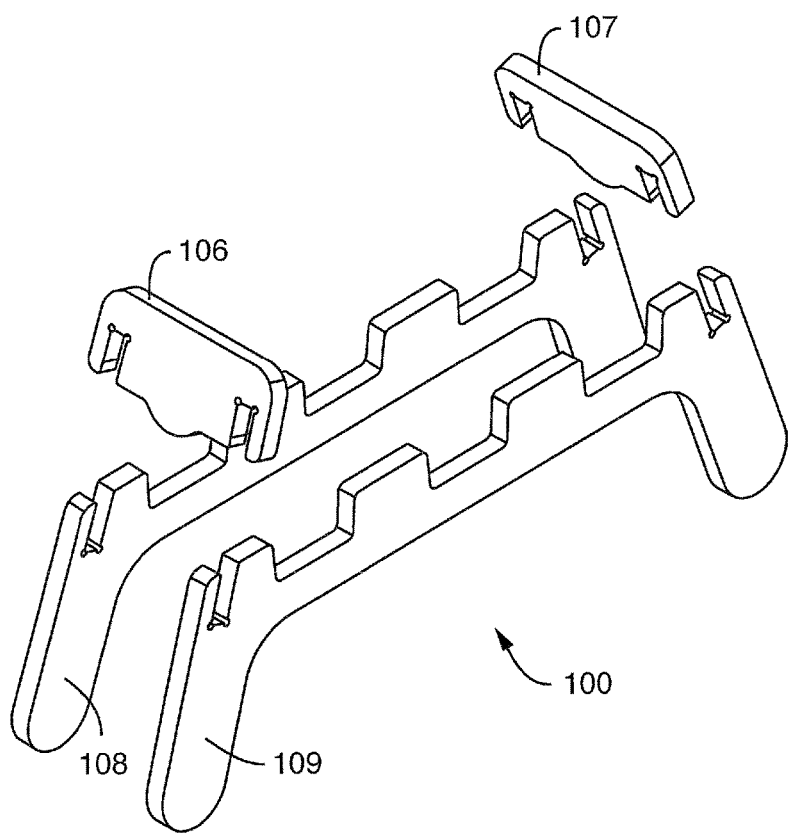
FIG. 35A shows first and second end caps (106 and 107) and first and second side panels (108 and 109) as the components of one embodiment of an unassembled culture stand or holder (100).
Figure 35B:
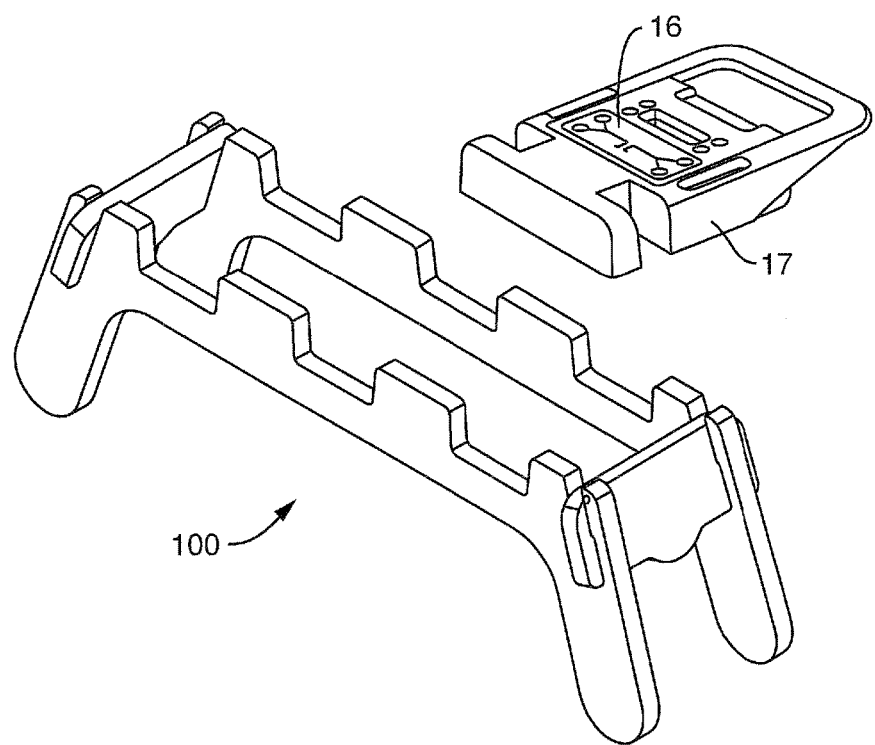
FIG. 35B shows the chip (16) and carrier (17) within a seeding guide, the seeding guide approaching (but not engaging) the stand (100).
Figure 35C:
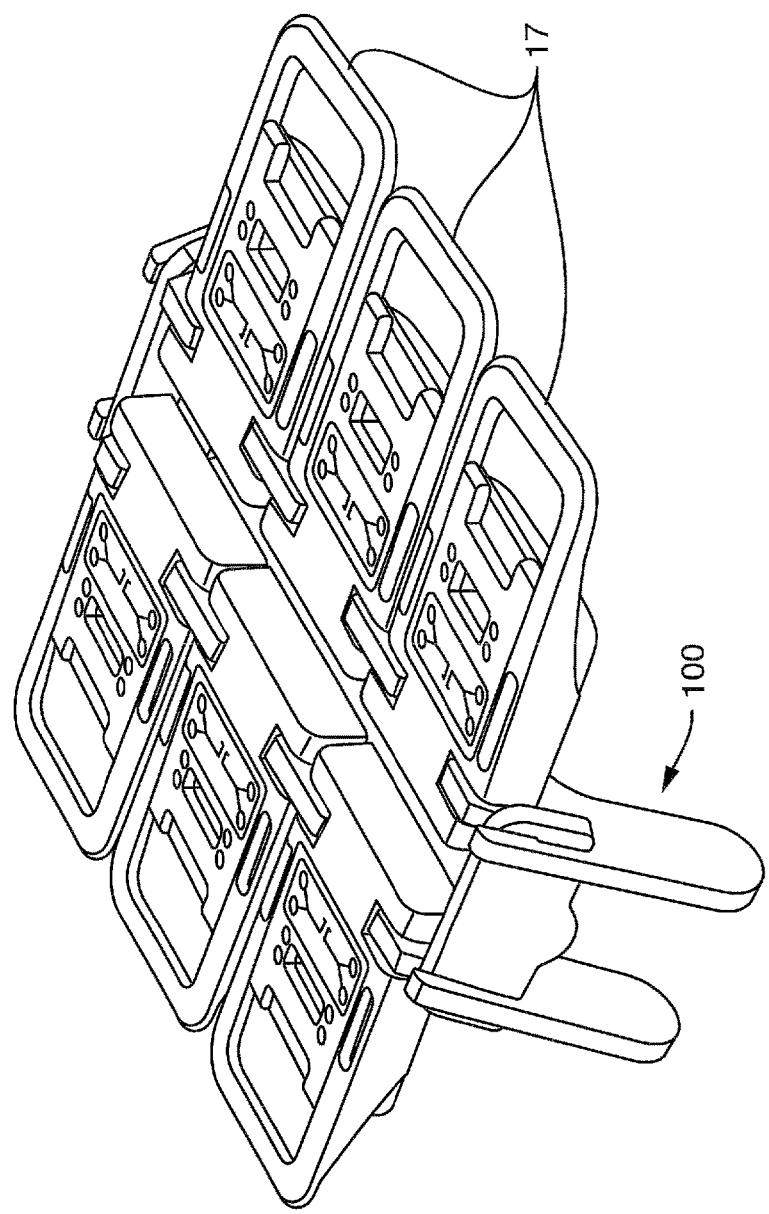
FIG. 35C shows six seeding guides comprising carriers (17) (with chips) mounted on the stand (100).
Figure 36A:
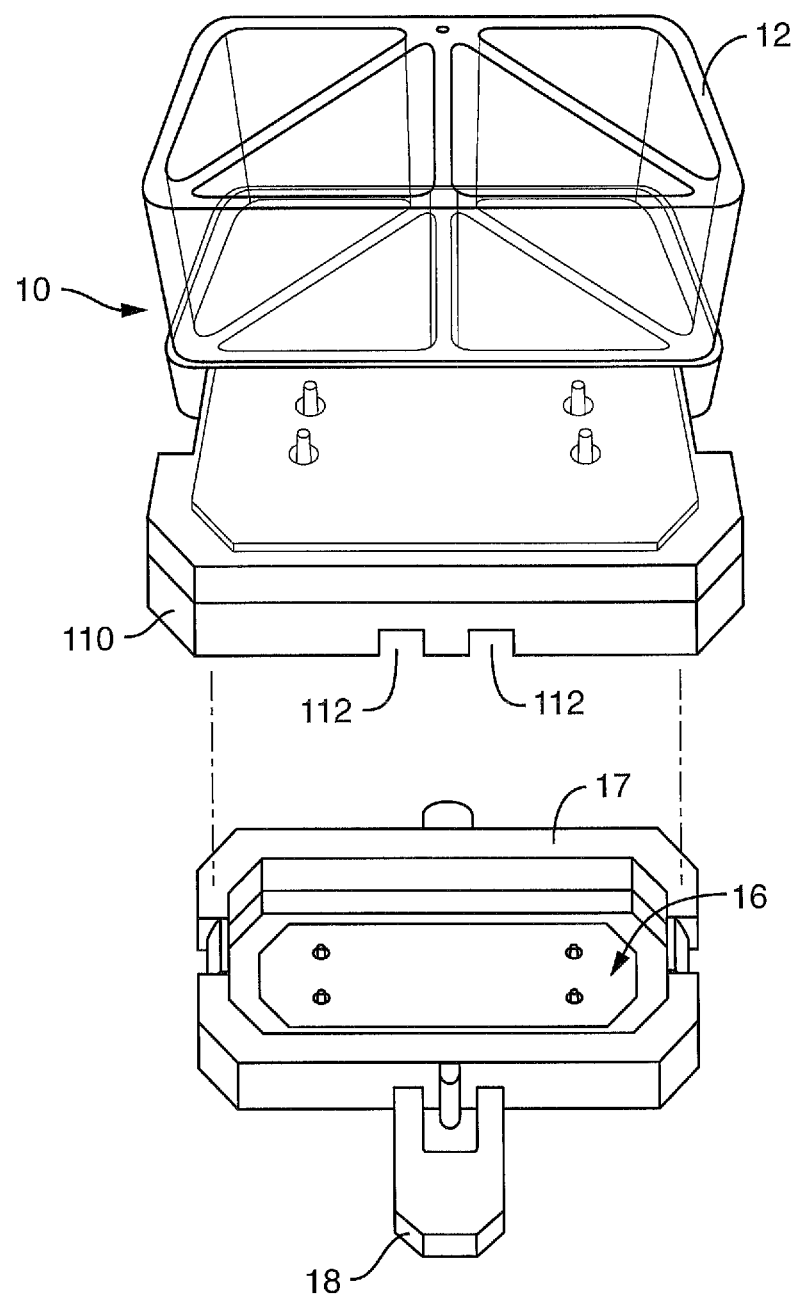
FIGS. 36A-C are photographs of a perfusion manifold assembly embodiment that lacks a skirt (or other projection) with side tracks for engaging a chip (or other microfluidic device) in a carrier). Instead, the base (110) of the assembly (10) is configured to accept the carrier (17) from underneath in a Lego™ block type connection (instead of from the side), i.e. the base (110) has a cavity (111) and openings (112) dimensioned to accept the carrier (17), while the carrier's handle or tab (18) is configured to fit in the openings (112).
Figure 36B:
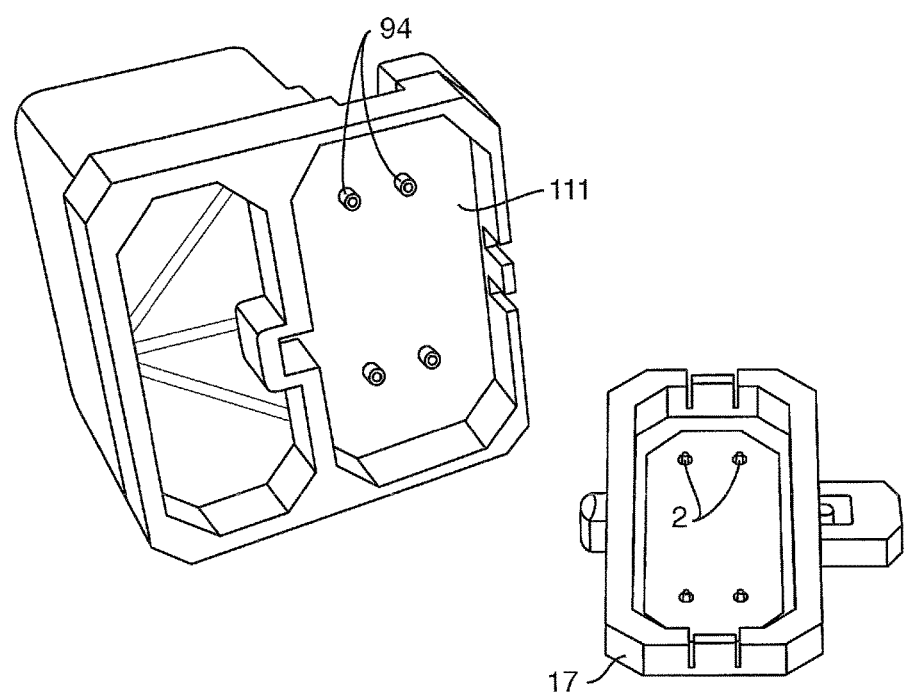
Figure 36C:
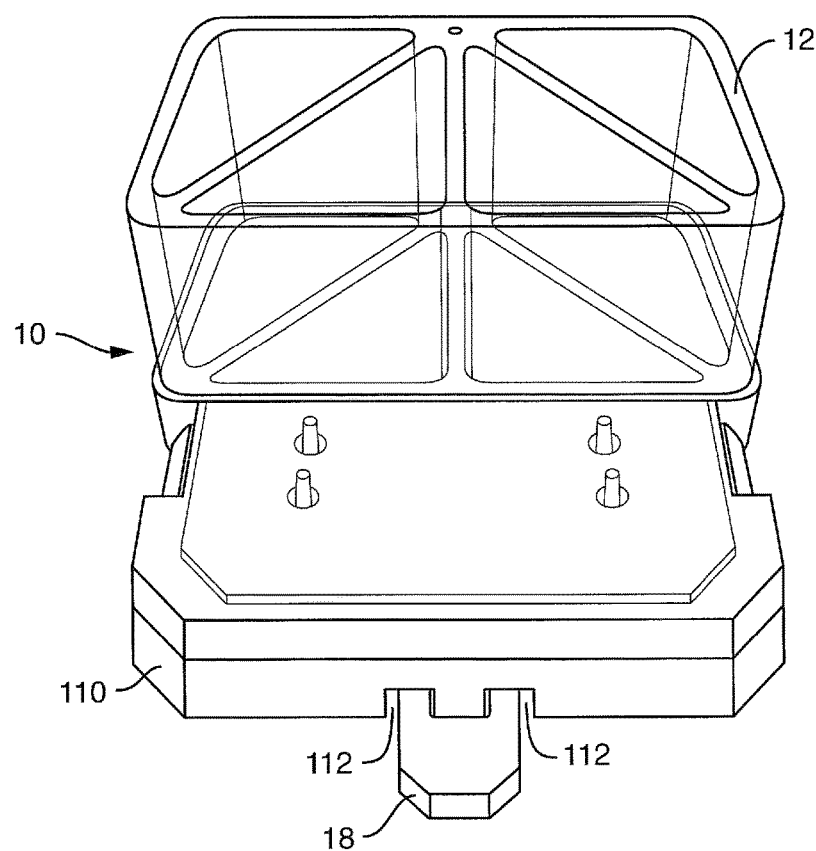

In many of the embodiments described above, the microfluidic chip or other device comprises cells. In some embodiments, cells are seeded directly into the chip. However, in other embodiments, the chip is contained in a carrier, which in turn is mounted on a stand to facilitate cell seeding. FIGS. 35A-C show one embodiment of a "seeding guide" and stand. In one embodiment, the seeding guide engages the carrier which contains the microfluidic chip, and holds the chip right side up (e.g. for top channel seeding) and upside down (e.g. for bottom channel seeding) in the various stages of seeding and/or coating (e.g. ECM coating), so as to improve aseptic technique. FIG. 35A shows how one embodiment of a stand (100) is assembled, i.e. by engaging two end caps (106, 107) with side panels (108, 109). FIG. 35B shows a chip (16) and a carrier (17) engaged by the seeding guide, the seeding guide approaching the stand (100). FIG. 35C shows six carriers (17) with chips, each engaged with a seeding guide, each seeding guide mounted on the stand (100). The seeding guide is adapted to accept a chip carrier (e.g. in a manner similar to how the skirt engages the chip carrier); after coating and/or seeding the same chip carrier can be (after disengaging from the seeding guide) linked to a perfusion manifold assembly. The seeding guide is designed to allow the chip to be held (whether right side up or upside down) such that its ports do not contact the tabletop or any other surface. This is in order to avoid the contamination of the chip through such contact. Additionally, the seeding guide or holder facilitates access to the chip through pipettes and/or needles and may optionally assist their insertion into chip ports using guide features.

In one embodiment, the present invention contemplates a method of seeding, comprising a) providing i) a chip at least partially contained in a carrier, ii) cells, iii) a seeding guide and iv) a stand with portions configured to accept at least one seeding guide in a stable mounted position; b) engaging said seeding guide with said carrier to create an engaged seeding guide, c) mounting said engaged seeding guide on said stand, and d) seeding said cells into said chip (e.g. with pipette tips) while said seeding guide (along with the carrier and chip) is in a stable mounted position. In one embodiment, the microfluidic device or chip comprises a top channel, a bottom channel, and a membrane separating at least a portion of said top and bottom channels. In one embodiment, the microfluidic device or chip, after the seeding of step c) comprises cells on the membrane and/or in (or on) one or more of the channels (e.g. the top channel is seeded). In one embodiment of this method, a plurality of seeding guide are mounted on the stand, permitting a plurality of chips to be seeded with cells. The guide has a number of functions, including a) keeping the surface of a chip sterile during handling, b) guiding pipette tips properly into ports during seeding, c) clearly labeling the channels of the chip (e.g. differentiating between the top and bottom channels), and d) permitting the shipping of the chips with liquid in the channels (as well as shipping of chips with cells already seeded or functionalized with ECM). The stand also has a number of functions, including a) keeping the chip level to allow cells to distribute evenly across the membrane, b) allowing the guide to be flipped upside down for seeding of the bottom channel, and c) enabling users to carry and store many seeded chips at one time. Thus, in one embodiment, after the seeding of step c), the method continues with the steps of flipping the chip upside down and seeding the bottom channel.

EXPERIMENTAL

Example 1

Conditions for bonding the capping layer (FIG. 2, element 13) to the backplane (14) were examined. Extruded SEBS sheets were bonded to a hot embossed plate. The SEBS sheets were designed to act as the capping layer to the channels that are formed in the COP via the hot embossing process and as a fluid and gas gasketing to mating parts. The testing showed that the 1 mm thick SEBS was better as a fluid seal between the reservoirs and the backplane. The hot embossed plates were fabricated from Zeonor 1420R. The SEBS materials used were:
  A. Thickness: 1 mm, Material: Kraton G1643, Mfg Process: extrusion
  B. Thickness: 0.2 mm, Material: Kraton G1643+5% Polypropylene, Mfg Process: extrusion An oven process was used in comparison to a laminator. The laminator produced marginal to not adequate bonding. However, the oven process revealed the following:

| Material Thickness | 0.2 mm SEBS | 1 mm SEBS |
| --- | --- | --- |
| Bonding Temp (C.) | 80 | 80 |
| Bonding Time | 1 hr-24 hr | |
| Clamping Pressure | None | 0.5 kg Applied through a silicone coated acrylic plate Necessary for conformal lamination/good bond production |
| Bond Quality | 1 hr: good bond 24 hr: excellent bond | Good bond |
| Anisotropic Effects | None noticeable | Yes. Requires clamping pressure to be held for ~30 min during cooling |

In some embodiments, the fluidic layer is sealed with a film. This film may be polymeric, metallic, biological or a combination thereof (e.g. A laminate of multiple materials). Examples of materials include polypropylene, SEBS, COP, PET, PMMA, aluminum, etc. Specifically, the film may be elastomeric. The film may be affixed to the fluidic layer by means of an adhesive agent, thermal lamination, laser welding, clamping, and other methods known in the art. The film may further be used to affix and potentially fluidically interconnect additional components to the fluidic layer. For example, the film may be used to adhere one or more reservoirs to the fluidic layer. In an example embodiment, the film is a thermal lamination film that includes EVA or EMA. In the example embodiment, the film may be first laminated against the fluidic layer using a thermal treatment and then, using a second thermal treatment, adheres one or more reservoirs to the fluidic layer. In a different embodiment, the film includes SEBS, which is known to be bondable to a variety of materials including polystyrene, COP, polypropylene, etc., either using a thermal treatment or with the help of one or more solvents. In this example, the SEBS film may be laminated to a fluidic layer (using thermal treatment or with the help of solvent) and using a second treatment, bond one or more reservoirs to the fluidic layers. There are multiple potential advantages to using a film that is elastomeric, deformable, or pliable, or film that reflows during the bonding process. These advantages include, for example: potentially conforming to the fluidic layer or other bonded component (e.g. reservoirs), thereby relaxing manufacturing tolerance (e.g. on the flatness or planarity of the manufactured parts), potentially simplifying the required parallelism or alignment during bonding (e.g. because the said film may deform to absorb errors in parallelism), and acting as a gasket to create a fluidic seal, for example, between the fluidic backplane and reservoirs. SEBS is especially advantageous as a bonding film, since it can bond under moderate temperatures (typically under 100 C) while not significantly reflowing. Reflowing may be undesirable as it poses a risk of filling in and blocking fluidic channels. By not significantly reflowing, SEBS can better maintain the dimensions and structure of fluidic channels and other features in the fluidic layer compared to materials that reflow (e.g. traditional thermal lamination films). Film thickness can range from 10 um to 5 mm in different embodiments. The film may include various fluidic ports or channels. The film need not be flat and can take on a variety of three-dimensional shapes.

Example 2

In this example, one embodiment of a protocol for chip activation is discussed. The example assumes that all work is done under a hood using aseptic techniques and all working spaces are sterile (or made sterile).
Part I: Preparing the Chip
A. Spray the exterior of the chip package with 70% Ethanol and wipe it prior to bring it inside hood.
B. Open package inside hood and take chip in chip carrier out (keep these together).
C. Place chip in chip carrier within large sterile dish
i. Only handle the chip carriers by their wings. Always use tweezer to handle chip, The surface of chip is connected with cell culture area. Avoid touching the surface of the chip with hands and keep the chip unit flat
D. Allow vial of Emulate Reagent 1 (ER1) powder (containing a cross-linker) to fully equilibrate to ambient temperature before opening to prevent condensation inside the storage container—ER1 is moisture and light sensitive
E. Turn the light in the biosafety hood off
F. Reconstitute the powder with Reagent 2
i. Add 1 ml of Emulate Reagent 2 (ER2) (containing a buffer) directly into the ER1 storage container and invert 3 times to mix thoroughly
ii. Cover the ER1 solution with tin foil to prevent light degradation
G. Wash chip
i. Orient the chip horizontally within the hood
ii. Pipette up 100 ul of ER2 solution using tip
iii. Place the pipette in a completely vertical position and insert into the bottom channel—If it is hard to find the port, navigate touching the surface near the port
iv. After finding the port, inject the tip into the port (make tight connection)
v. Wash 100 ul of ER2 solution and keep the pipette plunger depressed (if you see outlet fluid coming out, washing is done successfully, if you see fluid coming out from the same port of injection, tip is not injected properly, repeat step iv)
vi. To take out the tip, gently press the chip body using sterile tweezer and tip out, keep the pipette plunger depressed
vii. Aspirate outlet flow
viii. Repeat the same procedure for top channel washing
ix. After washing, empty top channel first and bottom channel with aspirator
H. Inject ER1 Solution to both channels
i. Pipette up 30 ul of ER1 solution using tip
ii. Navigate the port of inlet of bottom channel using pipette tip on top of the chip surface near the port
iii. After finding the port, inject the tip into the port (make tight connection)
iv. Inject 30 ul of ER1 solution and keep the pipette plunger depressed (if you see outlet fluid coming out, injection is done successfully, if you see fluid coming out from the same port of injection, tip is not injected properly, repeat step ii)
v. To take out the tip, gently press the chip body using sterile tweezer and tip out, keep the pipette plunger depressed
vi. Aspirate excessive fluid from the surface of chip (avoid to contact the port)
vii. Repeat the same procedure for the top channel using 50 ul of ER1 solution
viii. Avoid introduction of bubbles. Inspect channels under microscope to be sure no bubbles are present, if bubbles are present, inject with ER1 solution again
I. Place chips directly under UV lamps, ensure UV light unit is in hood, light turns on, and adjust setting with button on back to "constant"
J. Treat UV light for 20 min
K. After UV treatment, gently aspirate ER1 from channels via same ports until channels are free of solution
L. Wash with 100 ul of ER2 solution to both channels and then with 200 ul of dPBS
Part II: Coating
A. Prepare ECM as directed by manufacturer. It is recommended to aliquot ECM and freeze if manufacturer instructed. Avoid multiple freeze-thaw cycles
B. Calculate total volume of ECM solution
* Minimum volume for Channels
i. Top: 50 ul
ii. Bottom: 20 ul
iii. ECM Diluent: User defined per ECM, prepare on ice.
if using Matrigel, see Matrigel protocol (make sure matrigel protocol has "slushy ice, no touching, any warming will destroy matrigel)
C. Aspirate dPBS from channels
D. Load channels with ECM solution
i. Pipette up 30 ul of cold ECM solution using tip
ii. Navigate the port of inlet of bottom channel using pipette tip on top of the chip surface near the port
iii. After finding the port, inject the tip vertically into the port (make tight connection)
iv. Inject 30 ul of ECM solution and keep the pipette plunger depressed (if you see outlet fluid coming out, injection is done successfully, if you see fluid coming out from the same port of injection, tip is not injected properly, repeat step ii)
v. To take out the tip, gently press the chip body using sterile tweezer and tip out
vi. Aspirate excessive fluid from the surface of chip (avoid to contact the port)
vii. Repeat the same procedure for the top channel using 50 ul of ECM solution E. Incubate at 4° C. overnight or for 2 hour at 37° C.
F. Seal the dish containing coated chips using parafilm.

Example 3

This example provides one embodiment of a protocol for seeding cells inside the chip in the top channel (which is oriented horizontally, unless otherwise indicated). The example assumes aseptic techniques and a sterile environment.

It should be noted that, although some cells require very specific seeding conditions, in general an optimal seeding density is achieved when the cells are in a planar monolayer spaced closely. From this spacing, most primary cells will attach and spread into a confluent monolayer.

Reference is made below to "gravity washing." This involves a) placing a (bolus) drop of media (100 uL) over a port on one side of the channel, making sure not to introduce any air bubbles within the port itself, and b) allowing this to flow through the chip, constantly aspirating media excess from the outlet port.

A. Transfer the chips into the hood
B. Place them inside of a sterile dish (eg 15 mm culture dish)
C. Gently wash chips
i. Pipette up 200 ul of cell culture medium using tip
ii. Navigate the port of inlet of bottom channel using pipette tip on top of the chip surface near the port
iii. After finding the port, inject the tip vertically into the port (make tight connection)
iv. Wash 200 ul of medium and keep the pipette plunger depressed (if you see outlet fluid coming out, washing is done successfully, if you see fluid coming out from the same port of injection, tip is not injected properly, repeat step iv)
v. To take out the tip, gently press the chip body using sterile tweezer and tip out, keep the pipette plunger depressed
vi. Aspirate outlet fluid
vii. Repeat the same procedure for top channel washing
viii. Repeat washing step for both channels one more time
ix. Add medium drop in inlet and outlet ports (100 ul each)
D. Cover dish, and place to the incubator until cells are ready
E. Prepare cell suspension and count cell number
F. Seeding density is specific to the top and bottom channels, cell type, and to the user's defined needs
i. Top channel: e.g. Caco2 cells: 2.5 million cells/ml
ii. Bottom channel: e.g. HUVEC: confluent
G. After counting cells, adjust cell suspension to appropriate density
H. For top channel seeding, bring dish containing chips in the hood and aspirate excess medium on the surface of chip (only handle the chip carriers by their wings; keep the chip carrier flat—do not pick it up! This will ensure an even distribution of cells across the chip culture membrane)
I. Agitate cell suspension gently before seeding each chip
J. Pipette 50 μL of the cell suspension and seed into the top channel (top channel is the lower right hand port when the chip is in the horizontal position) (use one chip first)
i. Place the pipette in a completely vertical position and insert into the top channel (vertical is a gentler introduction into the chip and ensures a more even cell distribution)
ii. Inject 50 ul of cell suspension and keep the pipette plunger depressed (if you see outlet fluid coming out, injection is done successfully, if you see fluid coming out from the same port of injection, tip is not injected properly, repeat step ii)
iii. To take pipette tip out, gently press the chip body using sterile tweezer except cell culture area and tip out, keep the plunger depressed.
iv. Immediately aspirate outlet fluid from chip surface using seeded tip (avoid to contact the port)
v. Use the pipette to immediately remove outflow from chip surface using seeded tip
* Remove the outflow so that both inlet and outlet are even with surface of chip to prevent hydrostatic pressure flow
K. Cover the dish and transfer to the microscope to check density
L. After seeding, place the chips it in the incubator until cells have attached
i. Place a small reservoir (15 ml or 50 ml conical tube cap) with PBS inside of the dish to provide humidity to cells
ii. Range of attachment time is 1-3 hours depends on cell type
M. After cells have attached, gravity wash the chips with warm medium by gently washing media through the channels.
N. Return chips to incubator until ready to move on to next step Example 4

This example provides one embodiment of a protocol for seeding cells inside the chip in the bottom channel (which is oriented horizontally, unless otherwise indicated). The example assumes aseptic techniques and a sterile environment.

It should be noted that, although some cells require very specific seeding conditions, in general an optimal seeding density is achieved when the cells are in a planar monolayer spaced closely. From this spacing, most primary cells will attach and spread into a confluent monolayer.

Reference is made below to "gravity washing." This involves a) placing a (bolus) drop of media (100 uL) over a port on one side of the channel, making sure not to introduce any air bubbles within the port itself, and b) allowing this to flow through the chip, constantly aspirating media excess from the outlet port.

A. Bring dish containing chips in the hood and aspirate excess medium on the surface of chip (only handle the chip carriers by their wings; keep the chip carrier flat—do not pick it up! This will ensure an even distribution of cells across the chip culture membrane)
B. Agitate cell suspension gently before seeding each chip
C. Pipette 20 μL of the cell suspension and seed into the bottom channel (the bottom channel is the upper right hand port when the chip is in the horizontal position) (use one chip first)
i. Inject 20 ul of cell suspension and keep the pipette plunger depressed (if you see outlet fluid coming out, injection is done successfully, if you see fluid coming out from the same port of injection, tip is not injected properly, repeat step ii)
ii. To take pipette tip out, gently press the chip body using sterile tweezer except cell culture area and tip out, keep the plunger depressed.
iii. Immediately aspirate outlet fluid from chip surface using seeded tip (avoid to contact the port)
iv. Remove the outflow so that both inlet and outlet are even with surface of chip to prevent hydrostatic pressure flow
D. Cover the dish and transfer to the microscope to check density
E. After seeding, flip the chip inside of dish and place the chips it in the incubator until cells have attached underneath the membrane
i. Range of attachment time is 1-3 hours depends on cell type
ii. Place a small reservoir (15 ml or 50 ml conical tube cap) with PBS inside of the dish to provide humidity to cells F. After cells have attached, flip chips back, gravity wash the chips with warm medium by gently injecting media through the channels.

G. Return chips to incubator until ready to move on to next step (cells can be cultured in the chip under static conditions until ready to connect to the perfusion manifold for flow conditions)

i. Aspirate old medium from the chip surface ii. Gravity rinse the chips with warm medium by gently injecting media through the channels every day: 200 ul each for top and bottom channel, drop the medium in inlet port iii. Place a small reservoir (15 ml or 50 ml conical tube cap) with PBS inside of the dish to provide humidity to cells Example 5

In this example, one embodiment of a protocol for preparing the perfusion disposable or "pod" is provided. This assumes aseptic techniques and a sterile environment.

A. Warm media to 37° C. ahead of time

B. Transfer warmed media into the biohood

C. Aliquot required amount +5% into 50 mL conical tubes

D. Sanitize and transfer one steriflip vacuum filter into hood for each tube of media i. Take steriflip out of packaging and connect to 50 mL tube of media ii. Connect to vacuum inside of hood and invert iii. Use a timer to vacuum degas for a minimum of 15 min E. Prepare correct number of PODs (based on # of viable chips)

F. Sanitize the Emulate nests and trays with ethanol and transfer them into the hood G. Sanitize one packaged Pod for each of the viable Chips with ethanol and transfer into the hood (always hold only edges of POD with thumb and long finger; keep lid of POD on and flat using index finger while simultaneously holding POD)

H. Remove the reservoir lid and add media. This should create droplets suitable for drop-to-drop engagement of the POD and the Chip.

i. Input Reservoir: Fill 1-3 ml (1 ml minimum)

ii. Output Reservoir: 300 ul

I. Transfer Seeded Chips from the incubator and bring to hood i. Remove the pipette tips with a gentle twisting motion and dispose of them ii. Use a 200 μL pipette to add 10-50 μL of media over each port (avoid creating a bubble inside the port). This should create droplets suitable for drop-to-drop engagement of the POD and the Chip.

J. Connect Chip+Carrier to POD. This connection process should result in drop-to-drop engagement of the POD and the Chip using the droplets formed in Steps H and I.

i. In one hand, hold a chip carrier with the index finger and thumb pinching the carrier, with the thumb on the locking mechanism ii. With the other hand grasp the Pod with the thumb and long finger around the reservoir and place the index finger on the top of the lid to secure it iii. Orient the Pod so that you are looking "into" it, along the tracks inside it iv. Continuing to pinch the carrier, align the feet of the carrier with the tracks within the Pod v. Slide the chip carrier into the Pod vi. Use your thumb against the chip carrier to gently depress the locking mechanism until it slides into place, capturing the chip within the Pod vii. Confirm that each reservoir lid is correctly on each Pod

The invention claimed is:

1. A method of perfusing cells, comprising:
A) providing a) a perfusion manifold assembly comprising i) one or more fluid reservoirs, ii) a fluidic backplane positioned under, and in fluidic communication with, said fluid reservoirs, said fluidic backplane comprising fluid channels that terminate at fluid outlet ports, and iii) a skirt having a guide mechanism; and b) a microfluidic device positioned in a carrier, said carrier configured for detachably engaging said guide mechanism of said skirt, said microfluidic device comprising i) living cells, and ii) microchannels in fluidic communication with ii) one or more inlet ports on a iii) mating surface;
B) positioning said carrier such that it engages said guide mechanism of said skirt; and
C) moving said carrier until said one or more fluid inlet ports of said microfluidic device are positioned against said one or more fluid outlet ports of said perfusion manifold assembly under conditions such that said microfluidic device is linked and fluid flows from said fluid reservoirs of said perfusion manifold assembly through said one or more fluid outlet ports into said one or more fluid inlet ports and into said microchannels of said microfluidic device, thereby perfusing said cells.

2. The method of claim 1, wherein said one or more inlet ports on said mating surface of said microfluidic device comprise droplets protruding above said mating surface and one or more outlet ports comprise protruding droplets, such that said moving of step C) causes a droplet-to-droplet connection when one or more fluid inlet ports of said microfluidic device are positioned against said one or more fluid outlet ports of said perfusion manifold assembly.

3. The method of claim 2, wherein said droplet-to-droplet connection does not permit air to enter said one or more fluid inlet ports.

4. The method of claim 2, wherein the mating surface proximate to said droplets is hydrophobic.

5. The method of claim 1, further comprising the step of D) activating a locking mechanism for restricting movement of the carrier.

6. The method of claim 1, wherein said fluidic backplane comprises a fluid resistor.

7. The method of claim 1, wherein said guide mechanism comprises one or more side tracks.

8. The method of claim 7, wherein said carrier comprises one or more outer edges, said outer edges configured for detachably engaging said one or more side tracks of said skirt.

9. The method of claim 8, wherein said moving of step C) comprises sliding said carrier along said side tracks until said inlet and outlet ports are positioned against each other.

10. The method of claim 1, further comprising the step of placing said perfusion manifold assembly with said linked microfluidic device in an incubator.

11. The method of claim 1, further comprising the step of placing said perfusion manifold assembly with said linked microfluidic device in or on a culture module.

12. The method of claim 11, wherein said fluid reservoirs of said perfusion manifold assembly are covered with a cover assembly comprising a cover having a plurality of ports.

13. The method of claim 12, wherein said ports are through-hole ports.

14. The method of claim 12, wherein said ports are associated with filters and corresponding holes in a gasket.

15. The method of claim 12, wherein said culture module comprises a mating surface with pressure points that correspond to the ports on the cover, such that the step of placing of said perfusion manifold assembly with said linked microfluidic device in or on said culture module results in contact of said ports with said pressure points.

16. The method of claim 12, wherein said culture module comprises a mating surface with pressure points that correspond to the ports on the cover, such that after the step of placing of said perfusion manifold assembly with said linked microfluidic device in or on said culture module, the pressure points of the mating surface of the culture module are brought into contact with said ports of the cover assembly.

17. The method of claim 16, wherein said culture module comprises pressure controllers.

18. The method of claim 17, wherein said pressure controllers apply pressure to said fluid reservoirs via said pressure points corresponding to said ports on said cover.

19. The method of claim 11, wherein said culture module comprises a plurality of perfusion manifold assemblies.

20. The method of claim 11, wherein said culture module comprises integrated valves.

21. The method of claim 20, wherein said valves comprise Schrader valves.

22. A method of perfusing cells, comprising:
A) providing a) a perfusion manifold assembly comprising i) one or more fluid reservoirs, ii) a fluidic backplane positioned under, and in fluidic communication with, said fluid reservoirs, said fluidic backplane comprising fluid channels that terminate at fluid outlet ports, and b) a microfluidic device positioned in a carrier, said carrier configured for detachably engaging said perfusion manifold, said microfluidic device comprising i) living cells, and ii) microchannels in fluidic communication with ii) one or more inlet ports on a iii) mating surface;
B) positioning said carrier such that it engages said perfusion manifold; and
C) moving said carrier until said one or more fluid inlet ports of said microfluidic device are positioned against said one or more fluid outlet ports of said perfusion manifold assembly under conditions such that said microfluidic device is linked and fluid flows from said fluid reservoirs of said perfusion manifold assembly through said one or more fluid outlet ports into said one or more fluid inlet ports and into said microchannels of said microfluidic device, thereby perfusing said cells.

23. The method of claim 22, wherein said one or more inlet ports on said mating surface of said microfluidic device comprise droplets protruding above said mating surface and one or more outlet ports comprise protruding droplets, such that said moving of step C) causes a droplet-to-droplet connection when one or more fluid inlet ports of said microfluidic device are positioned against said one or more fluid outlet ports of said perfusion manifold assembly.

24. The method of claim 23, wherein said droplet-to-droplet connection does not permit air to enter said one or more fluid inlet ports.

25. The method of claim 23, wherein the mating surface proximate to said droplets is hydrophobic.

26. The method of claim 23, further comprising the step of D) activating a locking mechanism for restricting movement of the carrier.

27. The method of claim 22, wherein said fluidic backplane comprises a fluid resistor.

28. The method of claim 22, wherein said perfusion manifold comprises a guide mechanism comprising one or more side tracks.

29. The method of claim 28, wherein said carrier comprises one or more outer edges, said outer edges configured for detachably engaging said one or more side tracks of said guide mechanism.

30. The method of claim 29, wherein said moving of step C) comprises sliding said carrier along said side tracks until said inlet and outlet ports are positioned against each other.

31. The method of claim 22, further comprising the step of placing said perfusion manifold assembly with said linked microfluidic device in an incubator.

32. The method of claim 22, further comprising the step of placing said perfusion manifold assembly with said linked microfluidic device in or on a culture module.

33. The method of claim 32, wherein said fluid reservoirs of said perfusion manifold assembly are covered with a cover assembly comprising a cover having a plurality of ports.

34. The method of claim 33, wherein said ports are through-hole ports.

35. The method of claim 33, wherein said ports are associated with filters and corresponding holes in a gasket.

36. The method of claim 33, wherein said culture module comprises a mating surface with pressure points that correspond to the ports on the cover, such that the step of placing of said perfusion manifold assembly with said linked microfluidic device in or on said culture module results in contact of said ports with said pressure points.

37. The method of claim 33, wherein said culture module comprises a mating surface with pressure points that correspond to the ports on the cover, such that after the step of placing of said perfusion manifold assembly with said linked microfluidic device in or on said culture module, the pressure points of the mating surface of the culture module are brought into contact with said ports of the cover assembly.

38. The method of claim 37, wherein said culture module comprises pressure controllers.

39. The method of claim 38, wherein said pressure controllers apply pressure to said fluid reservoirs via said pressure points corresponding to said ports on said cover.

40. The method of claim 32, wherein said culture module comprises a plurality of perfusion manifold assemblies.

41. The method of claim 32, wherein said culture module comprises integrated valves.

42. The method of claim 41, wherein said valves comprise Schrader valves.

* * * * *